US012733662B2

(12) United States Patent
Aher et al.

(10) Patent No.: US 12,733,662 B2
(45) Date of Patent: Sep. 15, 2026

(54) MILLET AND FOOD PRODUCTS WITH REDUCED LIPASE ACTIVITY, GENES AND IMPLEMENTATION THEREOF

(71) Applicants: PIONEER HI-BRED INTERNATIONAL, INC., Johnston, IA (US); INTERNATIONAL CROPS RESEARCH INSTITUTE FOR THE SEMI-ARID TROPICS, Hyderabad (IN)

(72) Inventors: Rasika Rajendra Aher, Hyderabad (IN); Pooja Bhatnagar-Mathur, Hyderabad (IN); John D. Everard, Grimes, IA (US); Kayla S. Flyckt, Ankeny, IA (US); William James Gordon-Kamm, Urbandale, IA (US); Sudhakar Reddy Palakolanu, Hyderabad (IN); Kiran K. Sharma, Hyderabad (IN); Laura L. Wayne, Des Moines, IA (US)

( * ) Notice: Subject to any disclaimer, the term of this patent is extended or adjusted under 35 U.S.C. 154(b) by 38 days.

(21) Appl. No.: 18/682,689

(22) PCT Filed: Aug. 10, 2022

(86) PCT No.: PCT/US2022/074765
§ 371 (c)(1),
(2) Date: Feb. 9, 2024

(87) PCT Pub. No.: WO2023/019172
PCT Pub. Date: Feb. 16, 2023

(65) Prior Publication Data
US 2024/0349763 A1 Oct. 24, 2024

(30) Foreign Application Priority Data
Aug. 11, 2021 (IN) ............................ 202141036329

(51) Int. Cl.
*A23L 7/104* (2016.01)
*C12N 9/20* (2006.01)

(52) U.S. Cl.
CPC ................ *A23L 7/104* (2016.08); *C12N 9/20* (2013.01); *C12Y 301/01003* (2013.01)

(58) Field of Classification Search
None
See application file for complete search history.

(56) References Cited

U.S. PATENT DOCUMENTS

2011/0167514 A1* 7/2011 Brover ...................... A23L 7/10
800/290
2019/0185871 A1* 6/2019 Zhou ...................... C11C 3/003

OTHER PUBLICATIONS

Lazar, E., Vicenzi, E., Van Obberghen-Schilling, E., Wolff, B., Dalton, S., Watanabe, S., & Sporn, M. B. (1989). Transforming growth factor α: An aromatic side chain at position 38 is essential for biological activity. Molecular and cellular biology, 9(2), 860-864. (Year: 1989).*

(Continued)

*Primary Examiner* — Amjad Abraham
*Assistant Examiner* — Dequantarius Javon Speed

(57) ABSTRACT

Provided are millet and food products made from millet having reduced lipase activity. Also provided are nucleic acid sequences, constructs, expression cadettes, markers, primers probes, methods, gene editing tools, and materials useful in producing millet with reduced lipase activity as well as millet food products with reduced rancidity.

4 Claims, 3 Drawing Sheets
Specification includes a Sequence Listing.

(56) References Cited

OTHER PUBLICATIONS

Nonaka, T., Kametani, F., Arai, T., Akiyama, H., & Hasegawa, M. (2009). Truncation and pathogenic mutations facilitate the formation of intracellular aggregates of TDP-43. Human molecular genetics, 18(18), 3353-3364. (Year: 2009).*

GeneSeq Accession ID No. BAH99574. Bover et al. US-20110167514-A1, Jul. 7, 2021. (Year: 2021).*

Aher R.R., et al., "Loss-of-function of Triacylglycerol Lipases are Associated with Low Flour Rancidity in Pearl Millet [*Pennisetum glaucum* (L.) R. Br.]," Frontiers in Plant Science, 2022, vol. 13, No. 962667, 13 Pages.

International Preliminary Report on Patentability for International Application No. PCT/US2022/074765, mailed Feb. 22, 2024, 12 Pages.

Narayanan A., et al., "Storage Stability of Bio Fortified Pearl Millet Flour," International Journal of Agriculture Innovations and Research, 2017, vol. 5, No. 5, pp. 709-713.

* cited by examiner

SEQUENCE LISTING

```
Sequence total quantity: 113
SEQ ID NO: 1            moltype = DNA  length = 1200
FEATURE                 Location/Qualifiers
misc_feature            1..1200
                        note = depicts the nucleotide sequence of PgTAGLip1 gene
                         coding region(cDNA)
source                  1..1200
                        mol_type = other DNA
                        organism = synthetic construct
SEQUENCE: 1
atggataggc ggagacgcgc ggtcaaagcg gcggcggtta tggtgctctt gctgctgtcc  60
atcgatcctg ctggaggagc aaggagagat tggggtttcc attccccctc ttctgtcggt  120
tttactgagt ccaacacaga acccgatgtc aggagcagtg ggaagagttt tgcttttaac  180
tatactctgg ccaaggctat tgtggaatat gcatcagctg tatatatgac agacctaacg  240
gctctataca catggacatg ctcaagatgt aatgacttga ctcgagggtt tgaggtgaca  300
tgtataattg ttgatgtcca aaattgcttg caggtgtctg ttagcctttc cattatattg  360
ttccatcaat ttcattcaat gaaaaaaaat aagcatctgg tgattgtcca tccaatgtgg  420
caggcattcg ttggtgttga tcacaatctc aatgctatca ttgttgcaat aaggggaact  480
caagagaaca gcatacagaa ctggattaag gacttgatat ggaagcaagt taatcttaat  540
tatcccaaca tgcccaatgc taaggtccac attgggtttt actcttctta caataataca  600
cttttacgtc cagccatcac gaatgctgtt cgcaaggcta ggaagttgca tggagattgt  660
gacataattg ttacagggca ctcgatggga ggagcgattg cttctttctg tgcgcttgat  720
cttgccatca gctttggaag tgataatgtt catctgatga cttttggtca accacgtgtt  780
ggcaatgctg cttttgcctc ctattttgcc aaatatgtgc caaacacaat cagaatgaca  840
catcaacgtg atattgtgcc tcatttgccc ccttatttct tcttcctccc acagctgacg  900
taccgacact ttcccaggga ggtgtgggag catgatgttg atggcaagac aacctttcaa  960
gtctgcgatg gcagtggtga agacccaaat tgtagcagga gcgtgtttgt gctgttctgg  1020
agtgctactg accatttgac ctacatggga gttaagatac aggccgacga ctggagcacc  1080
tgcagaatcg tcatggggca aagtgttgag caactccaga ggagtcttgc cagcagcatt  1140
actacgtcag gactctctat cgacgtcatc attgcagaca atagcgtcca ggtcgtttga  1200

SEQ ID NO: 2            moltype = AA  length = 399
FEATURE                 Location/Qualifiers
REGION                  1..399
                        note = depicts the amino acid sequence of PgTAGLIP1
source                  1..399
                        mol_type = protein
                        organism = synthetic construct
SEQUENCE: 2
MDRRRRAVKA AAVMVLLLLS IDPAGGARRD WGFHSPSSVG FTESNTEPDV RSSGKSFAFN  60
YTLAKAIVEY ASAVYMTDLT ALYTWTCSRC NDLTRGFEVT CIIVDVQNCL QVSVSLSIIL  120
FHQFHSMKKN KHLVIVHPMW QAFVGVDHNL NAIIVAIRGT QENSIQNWIK DLIWKQVNLN  180
YPNMPNAKVH IGFYSSYNNT LLRPAITNAV RKARKLHGDC DIIVTGHSMG GAIASFCALD  240
LAISFGSDNV HLMTFGQPRV GNAAFASYFA KYVPNTIRMT HQRDIVPHLP PYFFFLPQLT  300
YRHFPREVWE HDVDGKTTFQ VCDGSGEDPN CSRSVFVLFW SATDHLTYMG VKIQADDWST  360
CRIVMGQSVE QLQRSLASSI TTSGLSIDVI IADNSVQVV                        399

SEQ ID NO: 3            moltype = DNA  length = 1068
FEATURE                 Location/Qualifiers
misc_feature            1..1068
                        note = depicts the nucleotide sequence of PgTAGLip2 gene
                         coding region(cDNA)
source                  1..1068
                        mol_type = other DNA
                        organism = synthetic construct
SEQUENCE: 3
atggctgcga agggcgcgac ggcggcgctg ctgctccttg cggcgctcct ggtctccgct  60
cctcctaccg ccgcggcggc ggcggagcag aaaggagtac tcacgatgaa gccttctgat  120
ggcggttatg cttataaccg tactcttgct cacattcttg tcgaatatgc gtccgctgtg  180
tatacatctg acttaacatc acttttcaca tggacctgtc caaggtgcaa agatcacaca  240
aagggctttg aggtgattga ggtcattgtg gatgtggcga actgtttaca ggcatttgtt  300
ggagttgctc ctgatccaca atccataatc attgcattta gagggactca acagcacagt  360
gtctcaaatt ggattgaaga tctcttctgg aagcagctcg atgtgactta tccaggcatg  420
cctgatgcaa tggttcatca tggattttat actgcatatt ataatacaac gctgcgattt  480
gagatcttga aatctattaa atgggcgagg aaaacatatg gaaaactacc cataaatgtt  540
gtgggtcact ccatgggagg ggctttagct tcattttgtg cccttgatct ttctgttaag  600
tttggctcac aggaagttga gctcatgact tttggacaac ctcggatagg caatcctgct  660
tttgctgcgt actttgctgc tcaagtccca agaacaatcc gtgtgaccca tcagaatgat  720
attgtgccac atttaccacc atactattat tacctaggtg aatggacata tcaccacttt  780
gctagagagg tttggcttca tgtgatcata gacggaaatg ttattaccag aaatgagaca  840
atctgtgatg attccgggga ggacccaacc tgcagcaggt cagtctatgg aataagtgtg  900
gcagatcatc ttgagtacta tggcgtcaca atgcattctg attcaagggg atcttgtcaa  960
tttgtaatgg gttccgccaa ctcagtatac agctacattc gtgaagttga tggaaccatc  1020
atcttgtcaa aatatgcgca agaatcacat atcctagaat ccatatga              1068
```

-continued

```
SEQ ID NO: 4            moltype = AA  length = 355
FEATURE                 Location/Qualifiers
REGION                  1..355
                        note = depicts the amino acid sequence of PgTAGLIP2
source                  1..355
                        mol_type = protein
                        organism = synthetic construct
SEQUENCE: 4
MAAKGATAAL LLLAALLVSA PPTAAAAAEQ KGVLTMKPSD GGYAYNRTLA HILVEYASAV  60
YTSDLTSLFT WTCPRCKDHT KGFEVIEVIV DVANCLQAFV GVAPDPQSII IAFRGTQQHS  120
VSNWIEDLFW KQLDVTYPGM PDAMVHHGFY TAYYNTTLRF EILKSIKWAR KTYGKLPINV  180
VGHSMGGALA SFCALDLSVK FGSQEVELMT FGQPRIGNPA FAAYFAAQVP RTIRVTHQND  240
IVPHLPPYYY YLGEWTYHHF AREVWLHVII DGNVITRNET ICDDSGEDPT CSRSVYGISV  300
ADHLEYYGVT MHSDSRGSCQ FVMGSANSVY SYIREVDGTI ILSKYAQESH ILESI       355

SEQ ID NO: 5            moltype = DNA  length = 1061
FEATURE                 Location/Qualifiers
misc_feature            1..1061
                        note = depicts the nucleotide sequence of PgTAGLip1 mutant
                         (cDNA) having1061 bp
source                  1..1061
                        mol_type = other DNA
                        organism = synthetic construct
SEQUENCE: 5
atggataggc ggagacgcgc ggtcaaagcg gcgacggtta tggtgctctt gctgctgtcc  60
atcgatcctg ctggaggagc aaggagagat tggggtttcc attccccctc ttctgtcggt  120
tttactgagt ccaacacaga acccgatgtc aggagcagtg ggaagagttt tgcttttaac  180
tatactctgg ccaaggctat tgtggaatat gcatcagctg tatatatgac agacctaacg  240
gctctataca catggacatg ctcaagatgt aatgacttga ctcgagggtt tgaggtgaca  300
tgtataattg ttgatgtcca aaattgcttg caggcattcg ttggtgttga tcacaatctc  360
aatgctatca ttgttgcaat aaggggaact caagagaaca gcatacagaa ctggattaag  420
gacttgatat ggaagcaagt taatcttaat tatcccaaca tgcccaatgc taagccatca  480
cgaatgctgt tcgcaaggct aggaagttgc atggagattg tgacataatt gttacagggc  540
actcgatggg aggagcgatt gcttctttct gtgcgcttga tcttgccatc agctttggaa  600
gtgataatgt tcatctgatg acttttggtc aaccacgtgt tggcaatgct gcttttgcct  660
cctattttgc caaatatgtg ccaaacacaa tcagaatgac acatcaacgt gatattgtgc  720
ctcatttgcc cccttatttc ttcttcctcc cacagctgac gtaccgacac tttcccaggg  780
aggtgtggga gcatgatgtt gatggcaaga caacctttca agtctgcgat ggcagtggtg  840
aagacccaaa ttgtagcagg agcgtgtttg tgctgttctg gagtgctact gaccatttga  900
cctacatggg agttaagata caggccgacg actggagcac ctgcagaatc gtcatggggc  960
aaagtgttga gcaactccag aggagtcttg ccagcagcat tactacgtca ggactctcta  1020
tcgacgtcat cattgcagac aatagcgtcc aggtcgtttg a                    1061

SEQ ID NO: 6            moltype = DNA  length = 528
FEATURE                 Location/Qualifiers
misc_feature            1..528
                        note = depicts the nucleotide sequence of PgTAGLip1 mutant
                         (cDNA) having528 bp
source                  1..528
                        mol_type = other DNA
                        organism = synthetic construct
SEQUENCE: 6
atggataggc ggagacgcgc ggtcaaagcg gcgacggtta tggtgctctt gctgctgtcc  60
atcgatcctg ctggaggagc aaggagagat tggggtttcc attccccctc ttctgtcggt  120
tttactgagt ccaacacaga acccgatgtc aggagcagtg ggaagagttt tgcttttaac  180
tatactctgg ccaaggctat tgtggaatat gcatcagctg tatatatgac agacctaacg  240
gctctataca catggacatg ctcaagatgt aatgacttga ctcgagggtt tgaggtgaca  300
tgtataattg ttgatgtcca aaattgcttg caggcattcg ttggtgttga tcacaatctc  360
aatgctatca ttgttgcaat aaggggaact caagagaaca gcatacagaa ctggattaag  420
gacttgatat ggaagcaagt taatcttaat tatcccaaca tgcccaatgc taagccatca  480
cgaatgctgt tcgcaaggct aggaagttgc atggagattg tgacataa              528

SEQ ID NO: 7            moltype = AA  length = 175
FEATURE                 Location/Qualifiers
REGION                  1..175
                        note = depicts the amino acid sequence of the PgTAGLIP1
                         mutant variant
source                  1..175
                        mol_type = protein
                        organism = synthetic construct
SEQUENCE: 7
MDRRRRAVKA ATVMVLLLLS IDPAGGARRD WGFHSPSSVG FTESNTEPDV RSSGKSFAFN  60
YTLAKAIVEY ASAVYMTDLT ALYTWTCSRC NDLTRGFEVT CIIVDVQNCL QAFVGVDHNL  120
NAIIVAIRGT QENSIQNWIK DLIWKQVNLN YPNMPNAKPS RMLFARLGSC MEIVT       175

SEQ ID NO: 8            moltype = DNA  length = 1072
FEATURE                 Location/Qualifiers
misc_feature            1..1072
                        note = depicts the nucleotide sequence of a mutant of
```

```
                         PgTAGLip2
source                  1..1072
                        mol_type = other DNA
                        organism = synthetic construct
SEQUENCE: 8
atggctgcga agggcgcgac ggcggcgctg ctgctgctcc tcctcgcggc gctcctggtc  60
tccgctcctc ccaccgccgc ggcggcggcg gagcagaaag gagtactcac gatgaagcct  120
tctgatggcg gttatgctta taaccgtact cttgctcaca ttcttgtcga atatgcgtcc  180
gctgtgtata catctgactt aacatcactt ttcacatgga cctgtccaag gtgcaaagat  240
cacacaaagg gctttgaggt gattgaggtc attgtggatg tggcgaactg tttacaggca  300
tttgttggag ttgctcctga tccacaatcc ataatcattg catttagagg gactcaacag  360
cacagtgtct caaattggat tgaagatctc ttctggaagc agctcgatgt gacttatcca  420
ggcatgcctg atgcaatggt tcatcatgga ttttatactg catattataa tacaacgctg  480
cgatttgaga tcttgaaatc tattaaatgg gcgaggaaaa catatggaaa actacccata  540
aatgttgtgg gtcactccat gggaggggct ttagcttcat tttgtgccct tgatctttct  600
gttaagtttg gctcacagga agttgagctc atgacttttg gacaacctcg gataggcaat  660
cctgtttttg ctgtgtactt tgctgctcaa gtcccaagaa caatccgtgt gacccatcag  720
aatgatattg tgccacattt accaccatac tattattacc taggtgaatg gacatatcac  780
cactttgcta gagaggtttg gcttcatgtg atcatagacg gaaatgttat taccagaaat  840
gagacaatct gtgatgattc cggggaggac ccaacctgca gcaggtcagt ctatggaata  900
agtgtggcag atcatcttga gtactatggc gtcacaatgc attctgattc agggatcttg  960
tcaatttgta atgggttccg ccaactcagt atacagctac attcgtgaag ttgatggaac  1020
catcatcttg tcaaaatatg cgcaagaatc acatatccta gaatccatat ga          1072

SEQ ID NO: 9            moltype = AA  length = 335
FEATURE                 Location/Qualifiers
REGION                  1..335
                        note = depicts the amino acid sequence of a mutant of
                         PgTAGLIP2
source                  1..335
                        mol_type = protein
                        organism = synthetic construct
SEQUENCE: 9
MAAKGATAAL LLLLAALLV SAPPTAAAAA EQKGVLTMKP SDGGYAYNRT LAHILVEYAS  60
AVYTSDLTSL FTWTCPRCKD HTKGFEVIEV IVDVANCLQA FVGVAPDPQS IIIAFRGTQQ  120
HSVSNWIEDL FWKQLDVTYP GMPDAMVHHG FYTAYYNTTL RFEILKSIKW ARKTYGKLPI  180
NVVGHSMGGA LASFCALDLS VKFGSQEVEL MTFGQPRIGN PVFAVYFAAQ VPRTIRVTHQ  240
NDIVPHLPPY YYYLGEWTYH HFAREVWLHV IIDGNVITRN ETICDDSGED PTCSRSVYGI  300
SVADHLEYYG VTMHSDSGIL SICNGFRQLS IQLHS                            335

SEQ ID NO: 10           moltype = DNA  length = 1077
FEATURE                 Location/Qualifiers
misc_feature            1..1077
                        note = depicts the nucleotide sequence of a mutant of
                         PgTAGLip2
source                  1..1077
                        mol_type = other DNA
                        organism = synthetic construct
SEQUENCE: 10
atggctgcga agggcgcgac ggcggcgctg ctgctgctcc tcgcggcgct cctggtctcc  60
gctcctccca ccgccgcggc ggcgggtgcg gcggagcaga aaggagtact cacgatgaag  120
ccttctgatg gcggttatgc ttataaccgt actcttgctc acattcttgt cgaatatgct  180
tccgctgtgt atacatctga cttaacatca cttttcacat ggacctgtcc aaggtgcaaa  240
gatcacacaa agggctttga ggtgattgag gtcattgtgg atgtggcgaa ctgtttacag  300
gcatttgttg gagttgctcc tgatccacaa tccataatca ttgcatttag agggactcaa  360
cagcacagtg tctcaaattg gattgaagat ctcttctgga agcagctcga tgtgacttat  420
ccaggcatgc ctgatgcaat ggttcatcat ggattttata ctgcatatta taatacaacg  480
ctgcgatttg agatcttgaa atctattaaa tgggcgagga aaacatatgg aaaactaccc  540
ataaatgttg tgggtcactc catgggaggc gctttagctt cattctgtgc ccttgatctt  600
tctgttaagt ttggctcaca ggaagttgag ctcatgactt ttggacaacc tcggataggc  660
aatcctgctt ttgctgcgta ctttgctgct caagtcccaa gaacaatccg tgtgacccat  720
cagaatgata ttgtgccaca tttaccaccg tactattatt acctaggtga atggacatat  780
caccactttg ctagagaggt ttagcttcat gtgatcatag acggaaatgt tattaccaga  840
aatgagacaa tctgtgatga ttccggggag gacccaacct gcagcaggtc agtctatgga  900
ataagtgtgg cagatcatct ggagtactat ggtgtcacaa tgcattctga ttcaagggga  960
tcttgtcaat ttgtaatggg ttccgccaac tcagtataca gctacattcg tgaagttgat  1020
ggaaccatca tcttgtcaaa atatgcgcaa gaatcacata tcctagaatc catatga     1077

SEQ ID NO: 11           moltype = AA  length = 267
FEATURE                 Location/Qualifiers
REGION                  1..267
                        note = depicts the amino acid sequence of a mutant of
                         PgTAGLIP2
source                  1..267
                        mol_type = protein
                        organism = synthetic construct
SEQUENCE: 11
MAAKGATAAL LLLLAALLVS APPTAAAAGA AEQKGVLTMK PSDGGYAYNR TLAHILVEYA  60
SAVYTSDLTS LFTWTCPRCK DHTKGFEVIE VIVDVANCLQ AFVGVAPDPQ SIIIAFRGTQ  120
```

```
QHSVSNWIED LFWKQLDVTY PGMPDAMVHH GFYTAYYNTT LRFEILKSIK WARKTYGKLP  180
INVVGHSMGG ALASFCALDL SVKFGSQEVE LMTFGQPRIG NPAFAAYFAA QVPRTIRVTH  240
QNDIVPHLPP YYYYLGEWTY HHFAREV                                     267

SEQ ID NO: 12           moltype = DNA  length = 1325
FEATURE                 Location/Qualifiers
misc_feature            1..1325
                        note = depicts the nucleotide sequence having 84bp
                         insertion at 89nucleotide position of PgTAGLip1
source                  1..1325
                        mol_type = other DNA
                        organism = synthetic construct
SEQUENCE: 12
atggataggc ggagacgcgc ggtcaaagcg gcgacggtta tggtgctctt gctgctgtcc  60
atcgatcctg ctggaggagc aaggagaggt acttcgattt tcgtcccacg cgagtgaaat  120
tctttcggaa gcccatcgaa acgggctctg attagtggtt tcttgctaac agattggggt  180
ttccattccc cctcttctgt cggttttact gagtccaaca cagaacccga tgtcaggagc  240
agtgggaaga gttttgcttt taactatact ctggccaagg ctattgtgga atatgcatca  300
gctgtatata tgacagacct aacggctcta tacacatgga catgctcaag atgtaatgac  360
ttgactcgag tatgatatct gggaatatgg tgtctagcac tagtttattg taatttgttt  420
cagtttaagc acatcgaaga tgcgcttttc actgacttta ttgtgggccc cttttcacaa  480
aacaggggtt tgaggtgaca tgtataattg ttgatgtcca aaattgcttg caggtgtctg  540
ttagcctttc cattatattg ttccatcaat ttcattcaat gaaaaaacaa ataagcatct  600
ggtgattgtc catccaatgt ggcaggcatt cgttggtgtt gatcacaatc tcaatgctat  660
cattgttgca ataaggggaa ctcaagagaa cagcatacag aactggatta aggacttgat  720
atggaagcaa gttaatctta attatcccaa catgcccaat gctaaggtcc acattgggtt  780
ttactcttct tacaataata cacttttacg tccagccatc acgaatgctg ttcgcaaggc  840
taggaagttg catggagatt gtgacataat tgttacaggg cactcgatgg gaggagcgat  900
tgcttctttc tgtgcgcttg atcttgccat cagctttgga agtgataatg ttcatctgat  960
gacttttggt caaccacgtg ttggcaatgc tgcttttgcc tcctattttg ccaaatatgt  1020
gccaaacaca atcagaatga cacatcaacg tgatattgtg cctcatttgc cccccttattt  1080
cttcttcctc ccacagctga cgtaccgaca ctttcccagg gaggagcgtg tttgtgctgt  1140
tctggagtgc tactgaccat ttgacctaca tgggagttaa gatacaggcc gacgactgga  1200
gcacctgcag aatcgtcatg ggcaaagtg ttgagcaact ccagaggagt cttgccagca  1260
gcattactac gtcaggactc tctatcgacg tcatcattgc agacaatagc gtccaggtcg  1320
tttga                                                             1325

SEQ ID NO: 13           moltype = AA  length = 38
FEATURE                 Location/Qualifiers
REGION                  1..38
                        note = depicts the amino acid sequence having an insertion
                         at 30th aminoacid position of PgTAGLIP1
source                  1..38
                        mol_type = protein
                        organism = synthetic construct
SEQUENCE: 13
MDRRRRAVKA ATVMVLLLLS IDPAGGARRG TSIFVPRE                          38

SEQ ID NO: 14           moltype = DNA  length = 1093
FEATURE                 Location/Qualifiers
misc_feature            1..1093
                        note = depicts the nucleotide sequence having deletion of
                         17bpnucleotides (269-285) in PgTAGLip1 gene
source                  1..1093
                        mol_type = other DNA
                        organism = synthetic construct
SEQUENCE: 14
atggataggc ggagacgcgc ggtcaaagcg gcggcggtta tggtgctctt gctgctgtcc  60
atcgatcctg ctggaggagc aaggagagat tggggtttcc attccccctc ttctgtcggt  120
tttactgagt ccaacacaga acccgatgtc aggagcagtg ggaagagttt tgcttttaac  180
tatactctgg ccaaggctat tgtggaatat gcatcagctg tatatatgac agacctaacg  240
gctctataca catggacatg ctcaagatgg gtttgaggtg acatgtataa ttgttgatgt  300
ccaaaattgc ttgcaggcat tcgttggtgt tgatcacaat ctcaatgcta tcattgttgc  360
aataagggga actcaagaga acagcataca gaactggatt aaggacttga tatggaagca  420
agttaatctt aattatccca acatgcccaa tgctaaggtc cacattgggt tttactcttc  480
ttacaataat acacttttac gtccagccat cacgaatgct gttcgcaagg ctaggaagtt  540
gcatggagat tgtgacataa ttgttacagg gcactcgatg ggaggagcga ttgcttcttt  600
ctgtgcgctt gatcttgcca tcagctttgg aagtgataat gttcatctga tgacttttgg  660
tcaaccacgt gttggcaatg ctgcttttgc ctcctatttt gccaaatatg tgccaaacac  720
aatcagaatg acacatcaac gtgatattgt gcctcatttg ccccccttatt tcttcttcct  780
cccacagctg acgtaccgac actttcccag ggaggtgtgg gagcatgatg ttgatggcaa  840
gacaaccttt caagtctgcg atggcagtgg tgaagaccca aattgtagca ggagcgtgtt  900
tgtgctgttc tggagtgcta ctgaccattt gacctacatg ggagttaaga tacaggccga  960
cgactggagc acctgcagaa tcgtcatggg gcaaagtgtt gagcaactcc agaggagtct  1020
tgccagcagc attactacgt caggactctc tatcgacgtc atcattgcag acaatagcgt  1080
ccaggtcgtt tga                                                    1093

SEQ ID NO: 15           moltype = AA  length = 91
FEATURE                 Location/Qualifiers
```

-continued

```
REGION                  1..91
                        note = depicts the amino acid sequence having deletion of 6
                         amino acids(CNDLTR) at 90-95 position of PgTAGLIP1
source                  1..91
                        mol_type = protein
                        organism = synthetic construct
SEQUENCE: 15
MDRRRRAVKA ATVMVLLLLS IDPAGGARRD WGFHSPSSVG FTESNTEPDV RSSGKSFAFN  60
YTLAKAIVEY ASAVYMTDLT ALYTWTCSRW V                                91

SEQ ID NO: 16           moltype = DNA  length = 1417
FEATURE                 Location/Qualifiers
misc_feature            1..1417
                        note = depicts the nucleotide sequence having 116 bp
                         insertion at 287nucleotide position of PgTAGLip1.
source                  1..1417
                        mol_type = other DNA
                        organism = synthetic construct
SEQUENCE: 16
atggataggc ggagacgcgc ggtcaaagcg gcgacggtta tggtgctctt gctgctgtcc  60
atcgatcctg ctggaggagc aaggagagat tggggtttcc attccccctc ttctgtcggt  120
tttactgagt ccaacacaga acccgatgtc aggagcagtg ggaagagttt tgcttttaac  180
tatactctgg ccaaggctat tgtggaatat gcatcagctg tatatatgac agacctaacg  240
gctctataca catggacatg ctcaagatgt aatgacttga ctcgagtatg atatctggga  300
atatggtgtc tagcactagt ttattgtaat ttgtttcagt ttaagcacat cgaagatgcg  360
cttttcactg actttattgt gggccccttt tcacaaaaca ggggtttgag gtgacatgta  420
taattgttga tgtccaaaat tgcttgcagg tgtctgttag cctttccatt atattgttcc  480
atcaatttca ttcaatgaaa aaacaaataa gcatctggtg attgtccatc caatgtggca  540
ggcattcgtt ggtgttgatc acaatctcaa tgctatcatt gttgcaataa ggggaactca  600
agagaacagg ttctgaaata attggcaaaa cttctactga tttttttttaa aaaaaaaatc  660
ttggagctgc aatctcgtga tgccccactt cttaaattta ctgatcagca tacagaactg  720
gattaaggac ttgatatgga agcaagttaa tcttaattat cccaacatgc ccaatgctaa  780
ggtccacatt gggttttact cttcttacaa taatacactt ttacgtccag ccatcacgaa  840
tgctgttcgc aaggctagga agttgcatgg agattgtgac ataattgtta cagggcactc  900
gatgggagga gcgattgctt ctttctgtgc gcttgatctt gccatcagct ttggaagtga  960
taatgttcat ctgatgactt ttggtcaacc acgtgttggc aatgctgctt ttgcctccta  1020
ttttgccaaa tatgtgccaa acacaatcag aatgacacat caacatgata ttgtgcctca  1080
tttgcccct tatttcttct tcctcccaca gctgacgtac cgacactttc ccagggaggt  1140
gtgggagcat gatgttgatg gcaagacaac ctttcaagtc tgcgatggca gtggtgaaga  1200
cccaaattgt agcaggagcg tgtttgtgct gttctggagt gctactgacc atttgaccta  1260
catgggagtt aagatacagg ccgacgactg gagcacctgc agaatcgtca tggggcaaag  1320
tgttgagcaa ctccagagga gtcttgccag cagcattact acgtcaggac tctctatcga  1380
cgtcatcatt gcagacaata gcgtccaggt cgtttga                           1417

SEQ ID NO: 17           moltype = AA  length = 96
FEATURE                 Location/Qualifiers
REGION                  1..96
                        note = depicts the amino acid sequence having an insertion
                         of 96position (V*) of PgTAGLIP1.
source                  1..96
                        mol_type = protein
                        organism = synthetic construct
SEQUENCE: 17
MDRRRRAVKA ATVMVLLLLS IDPAGGARRD WGFHSPSSVG FTESNTEPDV RSSGKSFAFN  60
YTLAKAIVEY ASAVYMTDLT ALYTWTCSRC NDLTRV                           96

SEQ ID NO: 18           moltype = DNA  length = 1045
FEATURE                 Location/Qualifiers
misc_feature            1..1045
                        note = depicts the nucleotide sequence having 155bp
                         deletion (269-423)in PgTAGLip1 gene
source                  1..1045
                        mol_type = other DNA
                        organism = synthetic construct
SEQUENCE: 18
atggataggc ggagacgcgc ggtcaaagcg gcgacggtta tggtgctctt gctgctgtcc  60
atcgatcctg ctggaggagc aaggagagat tggggtttcc attccccctc ttctgtcggt  120
tttactgagt ccaacacaga acccgatgtc aggagcagtg ggaagagttt tgcttttaac  180
tatactctgg ccaaggctat tgtggaatat gcatcagctg tatatatgac agacctaacg  240
gctctataca catggacatg ctcaagatgc attcgttggt gttgatcaca atctcaatgc  300
tatcattgtt gcaataaggg gaactcaaga gaacagcata cagaactgga ttaaggactt  360
gatatggaag caagttaatc ttaattatcc caacatgccc aatgctaagg tccacattgg  420
gttttactct tcttacaata atacactttt acgtccagcc atcacgaatg ctgttcgcaa  480
ggctaggaag ttgcatggag attgtgacat aattgttaca gggcactcga tgggaggagc  540
gattgcttct ttctgtgcgc ttgatcttgc catcagcttt ggaagtgata atgttcatct  600
gatgactttt ggtcaaccac gtgttggcaa tgctgctttt gcctcctatt ttgccaaata  660
tgtgccaaac acaatcagaa tgacacatca acgtgatatt gtgcctcatt tgccccctta  720
tttcttcttc ctcccacagc tgacgtaccg acactttccc agggaggtgt gggagcatga  780
tgttgatggc aagacaacct ttcaagtctg cgatggcagt ggtgaagacc caaattgtag  840
```

```
caggagcgtg tttgtgctgt tctggagtgc tactgaccat ttgacctaca tgggagttaa  900
gatacaggcc gacgactgga gcacctgcag aatcgtcatg gggcaaagtg ttgagcaact  960
ccagaggagt cttgccagca gcattactac gtcaggactc tctatcgacg tcatcattgc  1020
agacaatagc gtccaggtcg tttga                                        1045

SEQ ID NO: 19          moltype = AA  length = 94
FEATURE                Location/Qualifiers
REGION                 1..94
                       note = depicts the amino acid sequence having a deletion of
                        51 aminoacids (91-141 bp) in PgTAGLIP1
source                 1..94
                       mol_type = protein
                       organism = synthetic construct
SEQUENCE: 19
MDRRRRAVKA ATVMVLLLLS IDPAGGARRD WGFHSPSSVG FTESNTEPDV RSSGKSFAFN  60
YTLAKAIVEY ASAVYMTDLT ALYTWTCSRC IRWC                              94

SEQ ID NO: 20          moltype = DNA  length = 1003
FEATURE                Location/Qualifiers
misc_feature           1..1003
                       note = depicts the nucleotide sequence having 90bp
                        nucleotide deletion(331-420) in PgTAGLip1 gene
source                 1..1003
                       mol_type = other DNA
                       organism = synthetic construct
SEQUENCE: 20
atggataggc ggagacgcgc ggtcaaagcg gcgacggtta tggtgctctt gctgctgtcc  60
atcgatcctg ctggaggagc aaggagagat tggggtttcc attccccctc ttctgtcggt  120
tttactgagt ccaacacaga acccgatgtc aggagcagtg ggaagagttt tgcttttaac  180
tatactctgg ccaaggctat tgtggaatat gcatcagctg tatatatgac agacctaacg  240
gctctataca catggacatg ctcaagacgt aatgacttga ctcgagggtt tgaggtgaca  300
tgtataattg ttgatgtcca aaattgcttg caggcattcg ttggtgttga tcacaatctc  360
aatgctatca ttgttgcaat aaggggaact caagagaaca gcatacagaa ctggattaag  420
gacttgatat ggaagcaagt taatcttaat tatcccaaca tgcccaatgc taagccatca  480
cgaatgctgt tcgcaaggct aggaagttgc atggagattg tgacataatt gttacagggc  540
actcgatggg aggagcgatt gcttctttct gtgcgcttga tcttgccatc agctttggaa  600
gtgataatgt tcatctgatg acttttggtc aaccacgtgt tggcaatgct gcttttgcct  660
cctattttgc caaatatgtg ccaaacacaa tcagaatgac acatcaacgt gatattgtgc  720
ctcatttgcc cccttatttc ttcttcctcc cacagctgac gtaccgacac tttcccaggg  780
aggtgtggga gcatgatgtt gatggcaaga caacctttca agtctgcgat ggcagtggtg  840
aagacccaaa ttgtagcaga tacaggccga cgactggagc acctgcagaa tcgtcatggg  900
gcaaagtgtt gagcaactcc agaggagtct tgccagcagc attactacgt caggactctc  960
tatcgacgtc atcattgcag acaatagcgt ccaggtcgtt tga                   1003

SEQ ID NO: 21          moltype = AA  length = 175
FEATURE                Location/Qualifiers
REGION                 1..175
                       note = depicts the amino acid sequence having deletion of
                        30 amino acids(111-140) in PgTAGLIP1
source                 1..175
                       mol_type = protein
                       organism = synthetic construct
SEQUENCE: 21
MDRRRRAVKA ATVMVLLLLS IDPAGGARRD WGFHSPSSVG FTESNTEPDV RSSGKSFAFN  60
YTLAKAIVEY ASAVYMTDLT ALYTWTCSRR NDLTRGFEVT CIIVDVQNCL QAFVGVDHNL  120
NAIIVAIRGT QENSIQNWIK DLIWKQVNLN YPNMPNAKPS RMLFARLGSC MEIVT       175

SEQ ID NO: 22          moltype = DNA  length = 1231
FEATURE                Location/Qualifiers
misc_feature           1..1231
                       note = depicts the nucleotide sequence having 7bp
                        nucleotide deletion(490-496) in PgTAGLip1 gene
source                 1..1231
                       mol_type = other DNA
                       organism = synthetic construct
SEQUENCE: 22
atggataggc ggagacgcgc ggtcaaagcg gcgacggtta tggtgctctt gctgctgtcc  60
atcgatcctg ctggaggagc aaggagagat tggggtttcc attccccctc ttctgtcggt  120
tttactgagt ccaacacaga acccgatgtc aggagcagtg ggaagagttt tgcttttaac  180
tatactctgg ccaaggctat tgtggaatat gcatcagctg tatatatgac agacctaacg  240
gctctataca catggacatg ctcaagatgt aatgacttga ctcgagggtt tgaggtgaca  300
tgtataattg ttgatgtcca aaattgcttg caggcattcg ttggtgttga tcacaatctc  360
aatgctatca ttgttgcaat aaggggaact caagagaaca gaactggatt aaggacttga  420
tatggaagca agttaatctt aattatccca acatgcccaa tgctaaggtc cacattgggt  480
tttactcttc ttacaataat acacttttac gtccagccat cacgaatgct gttcgcaagg  540
ctaggaagtt gcatggagat tgtgacataa ttgttacagg gcactcgatg ggaggagcga  600
ttgcttcttt ctgtgcgctt gatcttgccg taagtgactc ctaaatacca agtatatatt  660
tattgccata aggtttcatt tttactgcac aagggattat caccggtggg catggatttt  720
attttcattc tctctgaatt gtctccttcg tttgcagatc agctttggaa gtgataatgt  780
```

```
tcatctgatg acttttggtc aaccacgtgt tggcaatgct gcttttgcct cctattttgc  840
caaatatgtg ccaaacacaa tcagaatgac acatcaacgt gatattgtgc ctcatttgcc  900
cccttatttc ttcttcctcc cacagctgac gtaccgacac tttcccaggg aggtgtggga  960
gcatgatgtt gatggcaaga caacctttca agtctgcgat ggcagtggtg aagacccaaa  1020
ttgtagcagg agcgtgtttg tgctgttctg gagtgctact gaccatttga cctacatggg  1080
agttaagata caggccgacg actggagcac ctgcagaatc gtcatggggc aaagtgttga  1140
gcaactccag aggagtcttg ccagcagcat tactacgtca ggactctcta tcgacgtcat  1200
cattgcagac aatagcgtcc aggtcgtttg a                                 1231

SEQ ID NO: 23          moltype = AA  length = 139
FEATURE                Location/Qualifiers
REGION                 1..139
                       note = depicts the amino acid sequence having deletion of
                        two aminoacids (Serine and Isoleucine) at 164-165th
                        position of PgTAGLIP1.
source                 1..139
                       mol_type = protein
                       organism = synthetic construct
SEQUENCE: 23
MDRRRRAVKA ATVMVLLLLS IDPAGGARRD WGFHSPSSVG FTESNTEPDV RSSGKSFAFN  60
YTLAKAIVEY ASAVYMTDLT ALYTWTCSRC NDLTRGFEVT CIIVDVQNCL QAFVGVDHNL  120
NAIIVAIRGT QENRTGLRT                                               139

SEQ ID NO: 24          moltype = DNA  length = 1003
FEATURE                Location/Qualifiers
misc_feature           1..1003
                       note = depicts the nucleotide sequence having deletion of
                        49b nucleotide(563-611) in PgTAGlip1 gene
source                 1..1003
                       mol_type = other DNA
                       organism = synthetic construct
SEQUENCE: 24
atggataggc ggagacgcgc ggtcaaagcg gcgacggtta tggtgctctt gctgctgtcc  60
atcgatcctg ctggaggagc aaggagagat tggggtttcc attccccctc ttctgtcggt  120
tttactgagt ccaacacaga acccgatgtc aggagcagtg ggaagagttt tgcttttaac  180
tatactctgg ccaaggctat tgtggaatat gcatcagctg tatatatgac agacctaacg  240
gctctataca catggacatg ctcaagacgt aatgacttga ctcgagggtt tgaggtgaca  300
tgtataattg ttgatgtcca aaattgcttg caggcattcg ttggtgttga tcacaatctc  360
aatgctatca ttgttgcaat aaggggaact caagagaaca gcatacagaa ctggattaag  420
gacttgatat ggaagcaagt taatcttaat tatcccaaca tgcccaatgc taagccatca  480
cgaatgctgt tcgcaaggct aggaagttgc atggagattg tgacataatt gttacagggc  540
actcgatggg aggagcgatt gcttctttct gtgcgcttga tcttgccatc agctttggaa  600
gtgataatgt tcatctgatg acttttggtc aaccacgtgt tggcaatgct gcttttgcct  660
cctattttgc caaatatgtg ccaaacacaa tcagaatgac acatcaacgt gatattgtgc  720
ctcatttgcc cccttatttc ttcttcctcc cacagctgac gtaccgacac tttcccaggg  780
aggtgtggga gcatgatgtt gatggcaaga caacctttca agtctgcgat ggcagtggtg  840
aagacccaaa ttgtagcaga tacaggccga cgactggagc acctgcagaa tcgtcatggg  900
gcaaagtgtt gagcaactcc agaggagtct tgccagcagc attactacgt caggactctc  960
tatcgacgtc atcattgcag acaatagcgt ccaggtcgtt tga                    1003

SEQ ID NO: 25          moltype = AA  length = 175
FEATURE                Location/Qualifiers
REGION                 1..175
                       note = depicts the amino acid sequence having deletion of
                        16 amino acids(189-224) in PgTAGLIP1
source                 1..175
                       mol_type = protein
                       organism = synthetic construct
SEQUENCE: 25
MDRRRRAVKA ATVMVLLLLS IDPAGGARRD WGFHSPSSVG FTESNTEPDV RSSGKSFAFN  60
YTLAKAIVEY ASAVYMTDLT ALYTWTCSRR NDLTRGFEVT CIIVDVQNCL QAFVGVDHNL  120
NAIIVAIRGT QENSIQNWIK DLIWKQVNLN YPNMPNAKPS RMLFARLGSC MEIVT       175

SEQ ID NO: 26          moltype = DNA  length = 1074
FEATURE                Location/Qualifiers
misc_feature           1..1074
                       note = depicts the nucleotide sequence having 6 bp
                        insertion at 33bp inPgTAGLip2 gene
source                 1..1074
                       mol_type = other DNA
                       organism = synthetic construct
SEQUENCE: 26
atggctgcga agggcgcgac ggcggcgctg ctgctgctcc tcctcgcggc gctcctggtc  60
tccgctcctc ccaccgccgc ggcggcggcg gagcagaaag gagtactcac gatgaagcct  120
tctgatggcg gttatgctta taaccgtact cttgctcaca ttcttgtcga atatgcgtcc  180
gctgtgtata catctgactt aacatcactt ttcacatgga cctgtccaag gtgcaaagat  240
cacacaaagg gctttgaggt gattgaggtc attgtggatg tggcgaactg tttacaggca  300
tttgttggag ttgctcctga tccacaatcc ataatcattg catttagagg gactcaacag  360
cacagtgtct caaattggat tgaagatctc ttctggaagc agctcgatgt gacttatcca  420
```

```
ggcatgcctg atgcaatggt tcatcatgga ttttatactg catattataa tacaacgctg  480
cgatttgaga tcttgaaatc tattaaatgg gcgaggaaaa catatggaaa actacccata  540
aatgttgtgg gtcactccat gggaggggct ttagcttcat tttgtgccct tgatctttct  600
gttaagtttg gctcacagga agttgagctc atgacttttg gacaacctcg gataggcaat  660
cctgcttttg ctgtgtactt tgctgctcaa gtcccaagaa caatccgtgt gacccatcag  720
aatgatattg tgccacattt accaccatac tattattacc taggtgaatg gacatatcac  780
cactttgcta gagaggtttg gcttcatgtg atcatagacg gaaatgttat taccagaaat  840
gagacaatct gtgatgattc cggggaggac ccaacctgca gcaggtcagt ctatggaata  900
agtgtggcag atcatcttga gtactatggc gtcacaatgc attctgattc aaggggatct  960
tgtcaatttg taatgggttc cgccaactca gtatacagct acattcgtga agttgatgga  1020
accatcatct tgtcaaaata tgcgcaagaa tcacatatcc tagaatccat atga        1074

SEQ ID NO: 27          moltype = AA  length = 357
FEATURE                Location/Qualifiers
REGION                 1..357
                       note = depicts the amino acid sequence having insertion of
                        2 amino acidsat 11th position in PgTAGLIP2
source                 1..357
                       mol_type = protein
                       organism = synthetic construct
SEQUENCE: 27
MAAKGATAAL LLLLLAALLV SAPPTAAAAA EQKGVLTMKP SDGGYAYNRT LAHILVEYAS  60
AVYTSDLTSL FTWTCPRCKD HTKGFEVIEV IVDVANCLQA FVGVAPDPQS IIIAFRGTQQ  120
HSVSNWIEDL FWKQLDVTYP GMPDAMVHHG FYTAYYNTTL RFEILKSIKW ARKTYGKLPI  180
NVVGHSMGGA LASFCALDLS VKFGSQEVEL MTFGQPRIGN PAFAVYFAAQ VPRTIRVTHQ  240
NDIVPHLPPY YYYLGEWTYH HFAREVWLHV IIDGNVITRN ETICDDSGED PTCSRSVYGI  300
SVADHLEYYG VTMHSDSRGS CQFVMGSANS VYSYIREVDG TIILSKYAQE SHILESI     357

SEQ ID NO: 28          moltype = DNA  length = 1074
FEATURE                Location/Qualifiers
misc_feature           1..1074
                       note = depicts the nucleotide sequence having 3bp insertion
                        at 32bpPgTAGLip2 gene
source                 1..1074
                       mol_type = other DNA
                       organism = synthetic construct
SEQUENCE: 28
atggctgcga agggcgcgac ggcggcgctg ctgctgctcc tcctcgcggc gctcctggtc  60
tccgctcctc ccaccgccgc ggcggcggcg gagcagaaag gagtactcac gatgaagcct  120
tctgatggcg gttatgctta taaccgtact cttgctcaca ttcttgtcga atatgcgtcc  180
gctgtgtata catctgactt aacatcactt ttcacatgga cctgtccaag gtgcaaagat  240
cacacaaagg gctttgaggt gattgaggtc attgtggatg tggcgaactg tttacaggca  300
tttgttggag ttgctcctga tccacaatcc ataatcattg catttagagg gactcaacag  360
cacagtgtct caaattggat tgaagatctc ttctggaagc agctcgatgt gacttatcca  420
ggcatgcctg atgcaatggt tcatcatgga ttttatactg catattataa tacaacgctg  480
cgatttgaga tcttgaaatc tattaaatgg gcgaggaaaa catatggaaa actacccata  540
aatgttgtgg gtcactccat gggaggggct ttagcttcat tttgtgccct tgatctttct  600
gttaagtttg gctcacagga agttgagctc atgacttttg gacaacctcg gataggcaat  660
cctgcttttg ctgtgtactt tgctgctcaa gtcccaagaa caatccgtgt gacccatcag  720
aatgatattg tgccacattt accaccatac tattattacc taggtgaatg gacatatcac  780
cactttgcta gagaggtttg gcttcatgtg atcatagacg gaaatgttat taccagaaat  840
gagacaatct gtgatgattc cggggaggac ccaacctgca gcaggtcagt ctatggaata  900
agtgtggcag atcatcttga gtactatggc gtcacaatgc attctgattc aaggggatct  960
tgtcaatttg taatgggttc cgccaactca gtatacagct acattcgtga agttgatgga  1020
accatcatct tgtcaaaata tgcgcaagaa tcacatatcc tagaatccat atga        1074

SEQ ID NO: 29          moltype = AA  length = 159
FEATURE                Location/Qualifiers
REGION                 1..159
                       note = depicts the amino acid sequence having an insertion
                        of one aminoacid at 12th position in PgTAGLIP2
source                 1..159
                       mol_type = protein
                       organism = synthetic construct
SEQUENCE: 29
MAAKGATAAL LLLLLAALLV SAPPTAAAAA EQKGVLTMKP SDGGYAYNRT LAHILVEYAS  60
AVYTSDLTSL FTWTCPRCKD HTKGFEVIEV IVDVANCLQA FVGVAPDPQS IIIAFRGTQQ  120
HSVSNWIEDL FWKQLDVTYP GMPDAMVHHG FYTAYYNTT                         159

SEQ ID NO: 30          moltype = DNA  length = 1074
FEATURE                Location/Qualifiers
misc_feature           1..1074
                       note = depicts the nucleotide sequence having an insertion
                        of 6nucleotide at 80th position in PgTAGLip2 gene
source                 1..1074
                       mol_type = other DNA
                       organism = synthetic construct
SEQUENCE: 30
atggctgcga agggcgcgac ggcggcgctg ctgctgctcc tcctcgcggc gctcctggtc  60
```

```
tccgctcctc ccaccgccgc ggcggcggcg gagcagaaag gagtactcac gatgaagcct  120
tctgatggcg gttatgctta taaccgtact cttgctcaca ttcttgtcga atatgcgtcc  180
gctgtgtata catctgactt aacatcactt ttcacatgga cctgtccaag gtgcaaagat  240
cacacaaagg gctttgaggt gattgaggtc attgtggatg tggcgaactg tttacaggca  300
tttgttggag ttgctcctga tccacaatcc ataatcattg catttagagg gactcaacag  360
cacagtgtct caaattggat tgaagatctc ttctggaagc agctcgatgt gacttatcca  420
ggcatgcctg atgcaatggt tcatcatgga ttttatactg catattataa tacaacgctg  480
cgatttgaga tcttgaaatc tattaaatgg gcgaggaaaa catatggaaa actacccata  540
aatgttgtgg gtcactccat gggaggggct ttagcttcat tttgtgccct tgatcttttct  600
gttaagtttg gctcacagga agttgagctc atgacttttg gacaacctcg gataggcaat  660
cctgcttttg ctgtgtactt tgctgctcaa gtcccaagaa caatccgtgt gacccatcag  720
aatgatattg tgccacattt accaccatac tattattacc taggtgaatg gacatatcac  780
cactttgcta gagaggtttg gcttcatgtg atcatagacg gaaatgttat taccagaaat  840
gagacaatct gtgatgattc cggggaggac ccaacctgca gcaggtcagt ctatggaata  900
agtgtggcag atcatcttga gtactatggc gtcacaatgc attctgattc aaggggatct  960
tgtcaatttg taatgggttc cgccaactca gtatacagct acattcgtga agttgatgga  1020
accatcatct tgtcaaaata tgcgcaagaa tcacatatcc tagaatccat atga        1074

SEQ ID NO: 31          moltype = AA  length = 357
FEATURE                Location/Qualifiers
REGION                 1..357
                       note = depicts the amino acid sequence having an insertion
                        of 2aminoacids at 28th position in PgTAGLIP 2
source                 1..357
                       mol_type = protein
                       organism = synthetic construct
SEQUENCE: 31
MAAKGATAAL LLLLLAALLV SAPPTAAAAA EQKGVLTMKP SDGGYAYNRT LAHILVEYAS  60
AVYTSDLTSL FTWTCPRCKD HTKGFEVIEV IVDVANCLQA FVGVAPDPQS IIIAFRGTQQ  120
HSVSNWIEDL FWKQLDVTYP GMPDAMVHHG FYTAYYNTTL RFEILKSIKW ARKTYGKLPI  180
NVVGHSMGGA LASFCALDLS VKFGSQEVEL MTFGQPRIGN PAFAVYFAAQ VPRTIRVTHQ  240
NDIVPHLPPY YYYLGEWTYH HFAREVWLHV IIDGNVITRN ETICDDSGED PTCSRSVYGI  300
SVADHLEYYG VTMHSDSRGS CQFVMGSANS VYSYIREVDG TIILSKYAQE SHILESI     357

SEQ ID NO: 32          moltype = DNA  length = 23
FEATURE                Location/Qualifiers
misc_feature           1..23
                       note = depicts the nucleotide sequence of primer
                        PgTAGLip1_F1
source                 1..23
                       mol_type = other DNA
                       organism = synthetic construct
SEQUENCE: 32
atggataggc ggagacgcgc ggt                                          23

SEQ ID NO: 33          moltype = DNA  length = 24
FEATURE                Location/Qualifiers
misc_feature           1..24
                       note = depicts the nucleotide sequence of primer
                        PgTAGLip1_R1
source                 1..24
                       mol_type = other DNA
                       organism = synthetic construct
SEQUENCE: 33
tcaaacgacc tggacgctat tgtc                                         24

SEQ ID NO: 34          moltype = DNA  length = 20
FEATURE                Location/Qualifiers
misc_feature           1..20
                       note = depicts the nucleotide sequence of primer
                        PgTAGLip1_R2
source                 1..20
                       mol_type = other DNA
                       organism = synthetic construct
SEQUENCE: 34
ttatgtcaca atctccatgc                                              20

SEQ ID NO: 35          moltype = DNA  length = 20
FEATURE                Location/Qualifiers
misc_feature           1..20
                       note = depicts the nucleotide sequence of primer
                        PgTAGLip1_R3
source                 1..20
                       mol_type = other DNA
                       organism = synthetic construct
SEQUENCE: 35
tcaaacccat cttgagcatg                                              20

SEQ ID NO: 36          moltype = DNA  length = 20
```

```
FEATURE                 Location/Qualifiers
misc_feature            1..20
                        note = depicts the nucleotide sequence of primer
                         PgTAGLip1_qF1
source                  1..20
                        mol_type = other DNA
                        organism = synthetic construct
SEQUENCE: 36
gcgtgtttgt gctgttctgg                                               20

SEQ ID NO: 37           moltype = DNA  length = 20
FEATURE                 Location/Qualifiers
misc_feature            1..20
                        note = depicts the nucleotide sequence of primer
                         PgTAGLip1_qR1
source                  1..20
                        mol_type = other DNA
                        organism = synthetic construct
SEQUENCE: 37
ttgccccatg acgattctgc                                               20

SEQ ID NO: 38           moltype = DNA  length = 20
FEATURE                 Location/Qualifiers
misc_feature            1..20
                        note = depicts the nucleotide sequence of primer
                         PgTAGLip1_qF2
source                  1..20
                        mol_type = other DNA
                        organism = synthetic construct
SEQUENCE: 38
tatggtgctc ttgctgctgt                                               20

SEQ ID NO: 39           moltype = DNA  length = 20
FEATURE                 Location/Qualifiers
misc_feature            1..20
                        note = depicts the nucleotide sequence of primer
                         PgTAGLip1_qR2
source                  1..20
                        mol_type = other DNA
                        organism = synthetic construct
SEQUENCE: 39
tcgggttctg tgttggactc                                               20

SEQ ID NO: 40           moltype = DNA  length = 21
FEATURE                 Location/Qualifiers
misc_feature            1..21
                        note = depicts the nucleotide sequence of primer
                         PgTAGLip1_qF3
source                  1..21
                        mol_type = other DNA
                        organism = synthetic construct
SEQUENCE: 40
tgttgcaata aggggaactc a                                             21

SEQ ID NO: 41           moltype = DNA  length = 20
FEATURE                 Location/Qualifiers
misc_feature            1..20
                        note = depicts the nucleotide sequence of primer
                         PgTAGLip1_qR3
source                  1..20
                        mol_type = other DNA
                        organism = synthetic construct
SEQUENCE: 41
gaccttagca ttgggcatgt                                               20

SEQ ID NO: 42           moltype = DNA  length = 22
FEATURE                 Location/Qualifiers
misc_feature            1..22
                        note = depicts the nucleotide sequence of primer PgEif4a_qF4
source                  1..22
                        mol_type = other DNA
                        organism = synthetic construct
SEQUENCE: 42
atcgtgagct ttacatccat cg                                            22

SEQ ID NO: 43           moltype = DNA  length = 22
FEATURE                 Location/Qualifiers
misc_feature            1..22
                        note = depicts the nucleotide sequence of primer PgEif4a_qR4
```

```
source                  1..22
                        mol_type = other DNA
                        organism = synthetic construct
SEQUENCE: 43
tatccctcag gatacggatg tc                                            22

SEQ ID NO: 44           moltype = DNA  length = 21
FEATURE                 Location/Qualifiers
misc_feature            1..21
                        note = depicts the nucleotide sequence of primer
                         PgTAGLip1_RNAi_SF
source                  1..21
                        mol_type = other DNA
                        organism = synthetic construct
SEQUENCE: 44
acatggacat gctcaagatg t                                             21

SEQ ID NO: 45           moltype = DNA  length = 21
FEATURE                 Location/Qualifiers
misc_feature            1..21
                        note = depicts the nucleotide sequence of primer
                         PgTAGLip1_RNAi_SR
source                  1..21
                        mol_type = other DNA
                        organism = synthetic construct
SEQUENCE: 45
attatcactt ccaaagctga t                                             21

SEQ ID NO: 46           moltype = DNA  length = 20
FEATURE                 Location/Qualifiers
misc_feature            1..20
                        note = depicts the nucleotide sequence of primer
                         PgTAGLip1_RNAi_ASF
source                  1..20
                        mol_type = other DNA
                        organism = synthetic construct
SEQUENCE: 46
attatcactt ccaaagctga                                               20

SEQ ID NO: 47           moltype = DNA  length = 21
FEATURE                 Location/Qualifiers
misc_feature            1..21
                        note = depicts the nucleotide sequence of primer
                         PgTAGLip1_RNAi_ASR
source                  1..21
                        mol_type = other DNA
                        organism = synthetic construct
SEQUENCE: 47
acatggacat gctcaagatg t                                             21

SEQ ID NO: 48           moltype = DNA  length = 20
FEATURE                 Location/Qualifiers
misc_feature            1..20
                        note = depicts the nucleotide sequence of primer
                         PgTAGLip2_F1
source                  1..20
                        mol_type = other DNA
                        organism = synthetic construct
SEQUENCE: 48
atggctgcga agggcgcgac                                               20

SEQ ID NO: 49           moltype = DNA  length = 21
FEATURE                 Location/Qualifiers
misc_feature            1..21
                        note = depicts the nucleotide sequence of primer
                         PgTAGLip2_R1
source                  1..21
                        mol_type = other DNA
                        organism = synthetic construct
SEQUENCE: 49
tcatatggat tctaggatat g                                             21

SEQ ID NO: 50           moltype = DNA  length = 20
FEATURE                 Location/Qualifiers
misc_feature            1..20
                        note = depicts the nucleotide sequence of primer
                         PgTAGLip2_R2
source                  1..20
                        mol_type = other DNA
```

```
                        organism = synthetic construct
SEQUENCE: 50
ttatgtcaca atctccatgc                                                20

SEQ ID NO: 51           moltype = DNA  length = 20
FEATURE                 Location/Qualifiers
misc_feature            1..20
                        note = depicts the nucleotide sequence of primer
                         PgTAGLip2_R3
source                  1..20
                        mol_type = other DNA
                        organism = synthetic construct
SEQUENCE: 51
tcaaacccat cttgagcatg                                                20

SEQ ID NO: 52           moltype = DNA  length = 20
FEATURE                 Location/Qualifiers
misc_feature            1..20
                        note = depicts the nucleotide sequence of primer
                         PgTAGLip2_qF1
source                  1..20
                        mol_type = other DNA
                        organism = synthetic construct
SEQUENCE: 52
ggctgcgaag ggcgcgacgg                                                20

SEQ ID NO: 53           moltype = DNA  length = 20
FEATURE                 Location/Qualifiers
misc_feature            1..20
                        note = depicts the nucleotide sequence of primer
                         PgTAGLip2_qR1
source                  1..20
                        mol_type = other DNA
                        organism = synthetic construct
SEQUENCE: 53
aaccgccatc agaaggcttc                                                20

SEQ ID NO: 54           moltype = DNA  length = 21
FEATURE                 Location/Qualifiers
misc_feature            1..21
                        note = depicts the nucleotide sequence of primer
                         PgTAGLip2_qF2
source                  1..21
                        mol_type = other DNA
                        organism = synthetic construct
SEQUENCE: 54
tgctagagag gtttggcttc a                                              21

SEQ ID NO: 55           moltype = DNA  length = 21
FEATURE                 Location/Qualifiers
misc_feature            1..21
                        note = depicts the nucleotide sequence of primer
                         PgTAGLip2_qR2
source                  1..21
                        mol_type = other DNA
                        organism = synthetic construct
SEQUENCE: 55
tgatctgcca cacttattcc a                                              21

SEQ ID NO: 56           moltype = DNA  length = 22
FEATURE                 Location/Qualifiers
misc_feature            1..22
                        note = depicts the nucleotide sequence of primer
                         PgTAGLip2_qF3
source                  1..22
                        mol_type = other DNA
                        organism = synthetic construct
SEQUENCE: 56
ttcaagggga tcttgtcaat tt                                             22

SEQ ID NO: 57           moltype = DNA  length = 21
FEATURE                 Location/Qualifiers
misc_feature            1..21
                        note = depicts the nucleotide sequence of primer
                         PgTAGLip2_qR3
source                  1..21
                        mol_type = other DNA
                        organism = synthetic construct
SEQUENCE: 57
```

```
tgattcttgc gcatattttg a                                          21

SEQ ID NO: 58          moltype = DNA  length = 22
FEATURE                Location/Qualifiers
misc_feature           1..22
                       note = depicts the nucleotide sequence of primer PgEif4a_qF4
source                 1..22
                       mol_type = other DNA
                       organism = synthetic construct
SEQUENCE: 58
atcgtgagct ttacatccat cg                                         22

SEQ ID NO: 59          moltype = DNA  length = 22
FEATURE                Location/Qualifiers
misc_feature           1..22
                       note = depicts the nucleotide sequence of primer PgEif4a_qR4
source                 1..22
                       mol_type = other DNA
                       organism = synthetic construct
SEQUENCE: 59
tatccctcag gatacggatg tc                                         22

SEQ ID NO: 60          moltype = DNA  length = 20
FEATURE                Location/Qualifiers
misc_feature           1..20
                       note = depicts the nucleotide sequence of sense strand
                        (139-158 bp)
source                 1..20
                       mol_type = other DNA
                       organism = synthetic construct
SEQUENCE: 60
gaacccgatg tcaggagcag                                            20

SEQ ID NO: 61          moltype = DNA  length = 20
FEATURE                Location/Qualifiers
misc_feature           1..20
                       note = depicts the nucleotide sequence of anti-sense strand
                        (348-367 bp)
source                 1..20
                       mol_type = other DNA
                       organism = synthetic construct
SEQUENCE: 61
ttccattata ttgttccatc                                            20

SEQ ID NO: 62          moltype = DNA  length = 20
FEATURE                Location/Qualifiers
misc_feature           1..20
                       note = depicts the nucleotide sequence of sense strand
                        (500-519 bp)
source                 1..20
                       mol_type = other DNA
                       organism = synthetic construct
SEQUENCE: 62
actggattaa ggacttgata                                            20

SEQ ID NO: 63          moltype = DNA  length = 20
FEATURE                Location/Qualifiers
misc_feature           1..20
                       note = depicts the nucleotide sequence of sense strand
                        (670-689 bp)
source                 1..20
                       mol_type = other DNA
                       organism = synthetic construct
SEQUENCE: 63
gttacagggc actcgatggg                                            20

SEQ ID NO: 64          moltype = DNA  length = 20
FEATURE                Location/Qualifiers
misc_feature           1..20
                       note = depicts the nucleotide sequence of anti-sense strand
                        (728-747 bp)
source                 1..20
                       mol_type = other DNA
                       organism = synthetic construct
SEQUENCE: 64
tcagctttgg aagtgataat                                            20

SEQ ID NO: 65          moltype = DNA  length = 20
FEATURE                Location/Qualifiers
```

```
misc_feature           1..20
                       note = depicts the nucleotide sequence of sense strand
                        (922-941 bp)
source                 1..20
                       mol_type = other DNA
                       organism = synthetic construct
SEQUENCE: 65
gtgtgggagc atgatgttga                                            20

SEQ ID NO: 66          moltype = DNA  length = 767
FEATURE                Location/Qualifiers
misc_feature           1..767
                       note = depicts the nucleotide sequence of Pdk intron
source                 1..767
                       mol_type = other DNA
                       organism = synthetic construct
SEQUENCE: 66
ctgtaatcaa tccaaatgta agatcaatga taacacaatg acatgatcta tcatgttacc  60
ttgtttattc atgttcgact aattcattta attaatagtc aatccattta gaagttaata  120
aaactacaag tattatttag aaattaataa gaatgttgat tgaaaataat actatataaa  180
atgatagatc ttgcgctttg ttatattagc attagattat gttttgttac attagattac  240
tgtttctatt agtttgatat tatttgttac tttagcttgt tatttaatat tttgtttatt  300
gataaattac aagcagattg gaatttctaa caaaatattt attaactttt aaactaaaat  360
atttagtaat ggtatagata tttaattata taataaacta ttaatcataa aaaaatatta  420
ttttaattta tttattctta tttttactat agtattttat cattgatatt taattcatca  480
aaccagctag aattactatt atgattaaaa caaatattaa tgctagtata tcatcttaca  540
tgttcgatca aattcattaa aaataatata cttactctca acttttatct tcttcgtctt  600
acacatcact tgtcatattt ttttacatta ctatgttgtt tatgtaaaca atatatttat  660
aaattatttt ttcacaatta taacaactat attattataa tcatactaat taacatcact  720
taactatttt atactaaaag gaaaaaagaa aataattatt tccttac               767

SEQ ID NO: 67          moltype = DNA  length = 767
FEATURE                Location/Qualifiers
misc_feature           1..767
                       note = depicts the nucleotide sequence of chsA intron
source                 1..767
                       mol_type = other DNA
                       organism = synthetic construct
SEQUENCE: 67
gtaaggaaat aattattttc ttttttcctt ttagtataaa atagttaagt gatgttaatt  60
agtatgatta taataatata gttgttataa ttgtgaaaaa ataatttata aatatattgt  120
ttacataaac aacatagtaa tgtaaaaaaa tatgacaagt gatgtgtaag acgaagaaga  180
taaaagttga gagtaagtat attatttta atgaatttga tcgaacatgt aagatgatat  240
actagcatta atatttgttt taatcataat agtaattcta gctggtttga tgaattaaat  300
atcaatgata aaatactata gtaaaaataa gaataaataa attaaaataa tattttttta  360
tgattaatag tttattatat aattaaatat ctataccatt actaaatatt ttagtttaaa  420
agttaataaa tattttgtta gaaattccaa tctgcttgta atttatcaat aaacaaaata  480
ttaaataaca agctaaagta acaaataata tcaaactaat agaaacagta atctaatgta  540
acaaaacata atctaatgct aatataacaa agcgcaagat ctatcatttt atatagtatt  600
attttcaatc aacattctta ttaatttcta aataatactt gtagttttat taacttctaa  660
atggattgac tattaattaa atgaattagt cgaacatgaa taaacaaggt aacatgatag  720
atcatgtcat tgtgttatca ttgatcttac atttggattg attacag               767

SEQ ID NO: 68          moltype = DNA  length = 498
FEATURE                Location/Qualifiers
misc_feature           1..498
                       note = depicts the nucleotide sequence of PgTAGLip1 sense
                        sequence
source                 1..498
                       mol_type = other DNA
                       organism = synthetic construct
SEQUENCE: 68
acatggacat gctcaagatg taatgacttg actcgagggt ttgaggtgac atgtataatt  60
gttgatgtcc aaaattgctt gcaggtgtct gttagccttt ccattatatt gttccatcaa  120
tttcattcaa tgaaaaaaaa taagcatctg gtgattgtcc atccaatgtg gcaggcattc  180
gttggtgttg atcacaatct caatgctatc attgttgcaa taaggggaac tcaagagaac  240
agcatacaga actggattaa ggacttgata tggaagcaag ttaatcttaa ttatcccaac  300
atgcccaatg ctaaggtcca cattgggttt tactcttctt acaataatac acttttacgt  360
ccagccatca cgaatgctgt tcgcaaggct aggaagttgc atggagattg tgacataatt  420
gttacagggc actcgatggg aggagcgatt gcttctttct gtgcgcttga tcttgccatc  480
agctttggaa gtgataat                                              498

SEQ ID NO: 69          moltype = DNA  length = 498
FEATURE                Location/Qualifiers
misc_feature           1..498
                       note = depicts the nucleotide sequence of PgTAGLip1
                        antisense sequence
source                 1..498
                       mol_type = other DNA
```

```
                        organism = synthetic construct
SEQUENCE: 69
attatcactt ccaaagctga tggcaagatc aagcgcacag aaagaagcaa tcgctcctcc  60
catcgagtgc cctgtaacaa ttatgtcaca atctccatgc aacttcctag ccttgcgaac  120
agcattcgtg atggctggac gtaaaagtgt attattgtaa gaagagtaaa acccaatgtg  180
gaccttagca ttgggcatgt tgggataatt aagattaact tgcttccata tcaagtcctt  240
aatccagttc tgtatgctgt tctcttgagt tccccttatt gcaacaatga tagcattgag  300
attgtgatca acaccaacga atgcctgcca cattggatgg acaatcacca gatgcttatt  360
ttttttcatt gaatgaaatt gatggaacaa tataatggaa aggctaacag acacctgcaa  420
gcaattttgg acatcaacaa ttatacatgt cacctcaaac cctcgagtca agtcattaca  480
tcttgagcat gtccatgt                                                498

SEQ ID NO: 70           moltype = DNA  length = 630
FEATURE                 Location/Qualifiers
misc_feature            1..630
                        note = depicts the nucleotide sequence of PgTAGLip2 sense
                         sequence
source                  1..630
                        mol_type = other DNA
                        organism = synthetic construct
SEQUENCE: 70
cctgatgcaa tggttcatca tggattttat actgcatatt ataatacaac gctgcgattt  60
gagatcttga aatctattaa atgggcgagg aaaacatatg gaaaactacc cataaatgtt  120
gtgggtcact ccatgggagg ggctttagct tcattttgtg cccttgatct ttctgttaag  180
tttggctcac aggaagttga gctcatgact tttggacaac ctcggatagg caatcctgct  240
tttgctgcgt actttgctgc tcaagtccca agaacaatcc gtgtgaccca tcagaatgat  300
attgtgccac atttaccacc atactattat tacctaggtg aatggacata tcaccacttt  360
gctagagagg tttggcttca tgtgatcata gacggaaatg ttattaccag aaatgagaca  420
atctgtgatg attccgggga ggacccaacc tgcagcaggt cagtctatgg aataagtgtg  480
gcagatcatc ttgagtacta tggcgtcaca atgcattctg attcaagggg atcttgtcaa  540
tttgtaatgg gttccgccaa ctcagtatac agctacattc gtgaagttga tggaaccatc  600
atcttgtcaa aatatgcgca agaatcacat                                  630

SEQ ID NO: 71           moltype = DNA  length = 630
FEATURE                 Location/Qualifiers
misc_feature            1..630
                        note = depicts the nucleotide sequence of PgTAGLip2
                         antisense sequence
source                  1..630
                        mol_type = other DNA
                        organism = synthetic construct
SEQUENCE: 71
atgtgattct tgcgcatatt ttgacaagat gatggttcca tcaacttcac gaatgtagct  60
gtatactgag ttggcggaac ccattacaaa ttgacaagat ccccttgaat cagaatgcat  120
tgtgacgcca tagtactcaa gatgatctgc cacacttatt ccatagactg acctgctgca  180
ggttgggtcc tccccggaat catcacagat tgtctcattt ctggtaataa catttccgtc  240
tatgatcaca tgaagccaaa cctctctagc aaagtggtga tatgtccatt cacctaggta  300
ataatagtat ggtggtaaat gtggcacaat atcattctga tgggtcacac ggattgttct  360
tgggacttga gcagcaaagt acgcagcaaa agcaggattg cctatccgag gttgtccaaa  420
agtcatgagc tcaacttcct gtgagccaaa cttaacagaa agatcaaggg cacaaaatga  480
agctaaagcc cctcccatgg agtgacccac aacatttatg ggtagttttc catatgtttt  540
cctcgcccat ttaatagatt tcaagatctc aaatcgcagc gttgtattat aatatgcagt  600
ataaaatcca tgatgaacca ttgcatcagg                                  630

SEQ ID NO: 72           moltype = DNA  length = 20
FEATURE                 Location/Qualifiers
misc_feature            1..20
                        note = depicts the nucleotide sequence of anti-sense strand
                         (115-134 bp)
source                  1..20
                        mol_type = other DNA
                        organism = synthetic construct
SEQUENCE: 72
taagcataac cgccatcaga                                              20

SEQ ID NO: 73           moltype = DNA  length = 20
FEATURE                 Location/Qualifiers
misc_feature            1..20
                        note = depicts the nucleotide sequence of sense strand
                         (270-289 bp)
source                  1..20
                        mol_type = other DNA
                        organism = synthetic construct
SEQUENCE: 73
ggatgtggcg aactgtttac                                              20

SEQ ID NO: 74           moltype = DNA  length = 20
FEATURE                 Location/Qualifiers
misc_feature            1..20
```

```
                        note = depicts the nucleotide sequence of anti-sense strand
                         (415-434 bp)
source                  1..20
                        mol_type = other DNA
                        organism = synthetic construct
SEQUENCE: 74
accattgcat caggcatgcc                                              20

SEQ ID NO: 75           moltype = DNA  length = 20
FEATURE                 Location/Qualifiers
misc_feature            1..20
                        note = depicts the nucleotide sequence of sense strand
                         (534-553 bp)
source                  1..20
                        mol_type = other DNA
                        organism = synthetic construct
SEQUENCE: 75
aaatgttgtg ggtcactcca                                              20

SEQ ID NO: 76           moltype = DNA  length = 20
FEATURE                 Location/Qualifiers
misc_feature            1..20
                        note = depicts the nucleotide sequence of sense strand
                         (773-792 bp)
source                  1..20
                        mol_type = other DNA
                        organism = synthetic construct
SEQUENCE: 76
accactttgc tagagaggtt                                              20

SEQ ID NO: 77           moltype = DNA  length = 20
FEATURE                 Location/Qualifiers
misc_feature            1..20
                        note = depicts the nucleotide sequence of sense strand
                         (991-1010 bp)
source                  1..20
                        mol_type = other DNA
                        organism = synthetic construct
SEQUENCE: 77
agctacattc gtgaagttga                                              20

SEQ ID NO: 78           moltype = DNA  length = 33
FEATURE                 Location/Qualifiers
misc_feature            1..33
                        note = depicts the nucleotide sequence of PgTAGLip1_F
                         (dCAPs marker)
source                  1..33
                        mol_type = other DNA
                        organism = synthetic construct
SEQUENCE: 78
atggataggc ggagacgcgc ggtcaaagcg gcc                               33

SEQ ID NO: 79           moltype = DNA  length = 25
FEATURE                 Location/Qualifiers
misc_feature            1..25
                        note = depicts the nucleotide sequence of PgTAGLip1_R
                         (dCAPs marker)
source                  1..25
                        mol_type = other DNA
                        organism = synthetic construct
SEQUENCE: 79
cttgagcatg tccatgtgta tagag                                        25

SEQ ID NO: 80           moltype = DNA  length = 24
FEATURE                 Location/Qualifiers
misc_feature            1..24
                        note = depicts the nucleotide sequence of PgTAGLip1_F (CAPS
                         marker)
source                  1..24
                        mol_type = other DNA
                        organism = synthetic construct
SEQUENCE: 80
ggcggagacg cgcggtcaaa gcgg                                         24

SEQ ID NO: 81           moltype = DNA  length = 25
FEATURE                 Location/Qualifiers
misc_feature            1..25
                        note = depicts the nucleotide sequence of PgTAGLip1_R (CAPS
                         marker)
```

```
source                 1..25
                       mol_type = other DNA
                       organism = synthetic construct
SEQUENCE: 81
cttgagcatg tccatgtgta tagag                                   25

SEQ ID NO: 82          moltype = DNA  length = 21
FEATURE                Location/Qualifiers
misc_feature           1..21
                       note = depicts the nucleotide sequence of PgTAGLip1_F1
                        (Indel marker)
source                 1..21
                       mol_type = other DNA
                       organism = synthetic construct
SEQUENCE: 82
ctaacggctc tatacacatg g                                       21

SEQ ID NO: 83          moltype = DNA  length = 20
FEATURE                Location/Qualifiers
misc_feature           1..20
                       note = depicts the nucleotide sequence of PgTAGLip1_R1
                        (Indel marker)
source                 1..20
                       mol_type = other DNA
                       organism = synthetic construct
SEQUENCE: 83
agttcccctt attgcaacaa                                         20

SEQ ID NO: 84          moltype = DNA  length = 20
FEATURE                Location/Qualifiers
misc_feature           1..20
                       note = depicts the nucleotide sequence of PgTAGLip1_F2
                        (Indel marker)
source                 1..20
                       mol_type = other DNA
                       organism = synthetic construct
SEQUENCE: 84
tatggaagca agttaatctt                                         20

SEQ ID NO: 85          moltype = DNA  length = 20
FEATURE                Location/Qualifiers
misc_feature           1..20
                       note = depicts the nucleotide sequence of PgTAGLip1_R2
                        (Indel marker)
source                 1..20
                       mol_type = other DNA
                       organism = synthetic construct
SEQUENCE: 85
atcgagtgcc ctgtaacaat                                         20

SEQ ID NO: 86          moltype = DNA  length = 20
FEATURE                Location/Qualifiers
misc_feature           1..20
                       note = depicts the nucleotide sequence of PgTAGLip1_F3
                        (Indel marker)
source                 1..20
                       mol_type = other DNA
                       organism = synthetic construct
SEQUENCE: 86
gaatatgcat cagctgtata                                         20

SEQ ID NO: 87          moltype = DNA  length = 20
FEATURE                Location/Qualifiers
misc_feature           1..20
                       note = depicts the nucleotide sequence of PgTAGLip1_R3
                        (Indel marker)
source                 1..20
                       mol_type = other DNA
                       organism = synthetic construct
SEQUENCE: 87
aagcaatttt ggacatcaac                                         20

SEQ ID NO: 88          moltype = DNA  length = 29
FEATURE                Location/Qualifiers
misc_feature           1..29
                       note = depicts the nucleotide sequence of PgTAGLip2_F
                        (dCAPs marker)
source                 1..29
                       mol_type = other DNA
```

```
                         organism = synthetic construct
SEQUENCE: 88
ttttggacaa cctcggatag gcaatccag                                       29

SEQ ID NO: 89            moltype = DNA  length = 25
FEATURE                  Location/Qualifiers
misc_feature             1..25
                         note = depicts the nucleotide sequence of PgTAGLip2_R
                          (dCAPs marker)
source                   1..25
                         mol_type = other DNA
                         organism = synthetic construct
SEQUENCE: 89
cttgagcatg tccatgtgta tagag                                           25

SEQ ID NO: 90            moltype = DNA  length = 21
FEATURE                  Location/Qualifiers
misc_feature             1..21
                         note = depicts the nucleotide sequence of PgTAGLip2_F (CAPs
                          marker)
source                   1..21
                         mol_type = other DNA
                         organism = synthetic construct
SEQUENCE: 90
agcagctcga tgtgacttat c                                               21

SEQ ID NO: 91            moltype = DNA  length = 22
FEATURE                  Location/Qualifiers
misc_feature             1..22
                         note = depicts the nucleotide sequence of PgTAGLip2_R (CAPs
                          marker)
source                   1..22
                         mol_type = other DNA
                         organism = synthetic construct
SEQUENCE: 91
agtacgcagc aaaagcagga tt                                              22

SEQ ID NO: 92            moltype = DNA  length = 20
FEATURE                  Location/Qualifiers
misc_feature             1..20
                         note = depicts the nucleotide sequence of PgTAGLip2_F
                          (Indel marker)
source                   1..20
                         mol_type = other DNA
                         organism = synthetic construct
SEQUENCE: 92
atggctgcga agggcgcgac                                                 20

SEQ ID NO: 93            moltype = DNA  length = 20
FEATURE                  Location/Qualifiers
misc_feature             1..20
                         note = depicts the nucleotide sequence of PgTAGLip2_R
                          (Indel marker)
source                   1..20
                         mol_type = other DNA
                         organism = synthetic construct
SEQUENCE: 93
tcgccacatc cacaatgacc                                                 20

SEQ ID NO: 94            moltype = DNA  length = 23
FEATURE                  Location/Qualifiers
misc_feature             1..23
                         note = depicts the nucleotide sequence of primer PgTAGLip1
                          _F foridentifying mutations in PgTAGLip1 gene.
source                   1..23
                         mol_type = other DNA
                         organism = synthetic construct
SEQUENCE: 94
acagacctaa cggctctata cac                                             23

SEQ ID NO: 95            moltype = DNA  length = 22
FEATURE                  Location/Qualifiers
misc_feature             1..22
                         note = depicts the nucleotide sequence of primer PgTAGLip1
                          _R foridentifying mutations in PgTAGLip1 gene
source                   1..22
                         mol_type = other DNA
                         organism = synthetic construct
SEQUENCE: 95
```

```
gcattgagat tgtgatcaac ac                                            22

SEQ ID NO: 96           moltype = DNA  length = 22
FEATURE                 Location/Qualifiers
misc_feature            1..22
                        note = depicts the nucleotide sequence of primer PgTAGLip1
                         _2F foridentifying mutations in PgTAGLip1 gene.
source                  1..22
                        mol_type = other DNA
                        organism = synthetic construct
SEQUENCE: 96
gcatacagaa ctggattaag ga                                            22

SEQ ID NO: 97           moltype = DNA  length = 22
FEATURE                 Location/Qualifiers
misc_feature            1..22
                        note = depicts the nucleotide sequence of primer PgTAGLip1
                         _2R foridentifying mutations in PgTAGLip1 gene.
source                  1..22
                        mol_type = other DNA
                        organism = synthetic construct
SEQUENCE: 97
agccttgcga acagcattcg tg                                            22

SEQ ID NO: 98           moltype = DNA  length = 21
FEATURE                 Location/Qualifiers
misc_feature            1..21
                        note = depicts the nucleotide sequence of primer PgTAGLip1
                         _3F foridentifying mutations in PgTAGLip1 gene.
source                  1..21
                        mol_type = other DNA
                        organism = synthetic construct
SEQUENCE: 98
gctaggaagt tgcatggaga t                                             21

SEQ ID NO: 99           moltype = DNA  length = 20
FEATURE                 Location/Qualifiers
misc_feature            1..20
                        note = depicts the nucleotide sequence of primer PgTAGLip1
                         _3R foridentifying mutations in PgTAGLip1 gene.
source                  1..20
                        mol_type = other DNA
                        organism = synthetic construct
SEQUENCE: 99
attctgattg tgtttggcac                                               20

SEQ ID NO: 100          moltype = DNA  length = 20
FEATURE                 Location/Qualifiers
misc_feature            1..20
                        note = depicts the nucleotide sequence of primer PgTAGLip2
                         _F foridentifying mutations in PgTAGLip2 gene.
source                  1..20
                        mol_type = other DNA
                        organism = synthetic construct
SEQUENCE: 100
atggctgcga agggcgcgac                                               20

SEQ ID NO: 101          moltype = DNA  length = 20
FEATURE                 Location/Qualifiers
misc_feature            1..20
                        note = depicts the nucleotide sequence of primer
                         PgTAGLip2_Rforidentifying mutations in PgTAGLip2 gene.
source                  1..20
                        mol_type = other DNA
                        organism = synthetic construct
SEQUENCE: 101
caatcacctc aaagcccttt                                               20

SEQ ID NO: 102          moltype = DNA  length = 20
FEATURE                 Location/Qualifiers
misc_feature            1..20
                        note = depicts the nucleotide sequence of primer
                         PgTAGLip2_1Ffor identifying mutations in PgTAGLip2 gene.
source                  1..20
                        mol_type = other DNA
                        organism = synthetic construct
SEQUENCE: 102
ctggtctccg ctcctcctac                                               20
```

```
SEQ ID NO: 103          moltype = DNA  length = 21
FEATURE                 Location/Qualifiers
misc_feature            1..21
                        note = depicts the nucleotide sequence of primer
                         PgTAGLip2_1Rfor identifying mutations in PgTAGLip2 gene.
source                  1..21
                        mol_type = other DNA
                        organism = synthetic construct
SEQUENCE: 103
ttcgccacat ccacaatgac c                                                21

SEQ ID NO: 104          moltype = DNA  length = 20
FEATURE                 Location/Qualifiers
misc_feature            1..20
                        note = depicts the nucleotide sequence of primer
                         PgTAGLip2_2F foridentifying mutations in PgTAGLip2 gene.
source                  1..20
                        mol_type = other DNA
                        organism = synthetic construct
SEQUENCE: 104
gacccaacct gcagcaggtc                                                  20

SEQ ID NO: 105          moltype = DNA  length = 20
FEATURE                 Location/Qualifiers
misc_feature            1..20
                        note = depicts the nucleotide sequence of primer
                         PgTAGLip2_2R foridentifying mutations in PgTAGLip2 gene.
source                  1..20
                        mol_type = other DNA
                        organism = synthetic construct
SEQUENCE: 105
tctaggatat gtgattcttg                                                  20

SEQ ID NO: 106          moltype = DNA  length = 22
FEATURE                 Location/Qualifiers
misc_feature            1..22
                        note = depicts the nucleotide sequence of primer PgTAGLip1
                         gRNAseq_F
source                  1..22
                        mol_type = other DNA
                        organism = synthetic construct
SEQUENCE: 106
gttatggtgc tcttgctgct gt                                               22

SEQ ID NO: 107          moltype = DNA  length = 20
FEATURE                 Location/Qualifiers
misc_feature            1..20
                        note = depicts the nucleotide sequence of primer PgTAGLip1
                         gRNAseq_F
source                  1..20
                        mol_type = other DNA
                        organism = synthetic construct
SEQUENCE: 107
gtctgcaatg atgacgtcga                                                  20

SEQ ID NO: 108          moltype = DNA  length = 21
FEATURE                 Location/Qualifiers
misc_feature            1..21
                        note = depicts the nucleotide sequence of primer PgTAGLip2
                         gRNAseq_F
source                  1..21
                        mol_type = other DNA
                        organism = synthetic construct
SEQUENCE: 108
gagcagaaag gagtactcac g                                                21

SEQ ID NO: 109          moltype = DNA  length = 21
FEATURE                 Location/Qualifiers
misc_feature            1..21
                        note = depicts the nucleotide sequence of primer PgTAGLip2
                         gRNAseq_R
source                  1..21
                        mol_type = other DNA
                        organism = synthetic construct
SEQUENCE: 109
ctaggatatg tgattcttgc g                                                21

SEQ ID NO: 110          moltype = DNA  length = 24
FEATURE                 Location/Qualifiers
```

-continued

```
misc_feature          1..24
                      note = depicts the nucleotide sequence of primer nptII_ConF
source                1..24
                      mol_type = other DNA
                      organism = synthetic construct
SEQUENCE: 110
ttgatatact tggatgatgg cata                                          24

SEQ ID NO: 111        moltype = DNA  length = 22
FEATURE               Location/Qualifiers
misc_feature          1..22
                      note = depicts the nucleotide sequence of primer nptII_ConR
source                1..22
                      mol_type = other DNA
                      organism = synthetic construct
SEQUENCE: 111
agccatgatg gatactttct cg                                            22

SEQ ID NO: 112        moltype = DNA  length = 22
FEATURE               Location/Qualifiers
misc_feature          1..22
                      note = depicts the nucleotide sequence of primer Hpt_F
source                1..22
                      mol_type = other DNA
                      organism = synthetic construct
SEQUENCE: 112
ttgacattgg ggagtttagc ga                                            22

SEQ ID NO: 113        moltype = DNA  length = 22
FEATURE               Location/Qualifiers
misc_feature          1..22
                      note = depicts the nucleotide sequence of primer Hpt_R
source                1..22
                      mol_type = other DNA
                      organism = synthetic construct
SEQUENCE: 113
gtttccacta tcggcgagta ct                                            22
```

MILLET AND FOOD PRODUCTS WITH REDUCED LIPASE ACTIVITY, GENES AND IMPLEMENTATION THEREOF

CROSS-REFERENCE TO RELATED APPLICATIONS

This Application is a 35 U.S.C. § 371 national stage application of PCT International Application No. PCT/US2022/074765, filed Aug. 10, 2022, which claims the right of priority and benefit of Indian Provisional Application 20/214,103629 filed on Aug. 11, 2021, the contents of each are incorporated by reference herein in their entirety.

REFERENCE TO SEQUENCE LISTING SUBMITTED ELECTRONICALLY

The official copy of the sequence listing is submitted electronically via EFS-Web as an XML-formatted sequence listing with a file named 8853-WO-PCT_ST.26, created on Aug. 10, 2022 and having a size of 176,128 bytes, which is filed concurrently with the specification. The sequence listing is part of the specification and is herein incorporated by reference in its entirety.

FIELD OF INVENTION

The present disclosure relates to plant molecular biology, including isolated polynucleotides, gene-edited or transgenic plants and plant parts (e.g., seed or grain) with mutant lipase genes and/or reduced lipase activity, and methods of obtaining such plants, seed, or grain. Also disclosed herein are plant lines and methods for obtaining plant lines having seed or grain with mutant lipase genes and/or reduced lipase activity. Food products from such plants, seed or grain are also disclosed.

BACKGROUND OF INVENTION

Millets, including pearl millet, finger millet, foxtail millet, small millet, and kodo millet are among the most important cereals grown in the semi-arid tropics. Millets are highly nutritious and a principal staple food crop for millions of people across Asia. For example, pearl millet is grown in the driest regions due to its ability to tolerate and thrive under continuous as well as erratic droughts. The crop has potential to contribute to food and nutritional security, as it is a powerhouse of nutrients. Pearl millet is a highly nutritional source of carbohydrates, protein, vitamins, and minerals such as Iron (Fe) and Zinc (Zn). Besides, being a good source of vitamin A, vitamin B, folic acid, calcium, magnesium, iron and zinc, the grain is gluten-free and contains high amounts of antioxidants which have proven beneficial for human health and well-being.

Pearl millet is recognized as an important food crop in the developing countries and is known for having superior balanced nutrients, as compared to other cereals. Pearl millet can help alleviate food shortages and meet the nutritional demands of an increasing population. Recently, millets are receiving increasing spotlight in combating diabetes, micronutrients deficiency and obesity as a dietary option (Kaur, B., & Henry, J. (2014). Micronutrient status in type 2 diabetes: a review. Advances in food and nutrition research, 71, 55-100; Varsha R and Narayanan A (2017). Storage Stability of Bio Fortified Pearl Millet Flour. *International Journal of Agriculture Innovations and Research,* 5(5) 2319-1473).

Despite its many superior qualities, pearl millet meal or flour is difficult to store for long periods of time. Rapid development of off flavors and odor in pearl millet flour is the major hindrance to wider consumer acceptability. Pearl millet has to be milled on a weekly basis for human use, which increases the drudgery of users especially women in the household, who are involved in its grinding and milling. Despite being a nutri-climate smart cereal crop, millets are disappearing from the people's diet and farmlands primarily due to lack of traction from industry due to post harvest issues such as rancidity in milled flour leading to unpleasant odour and taste making its storage challenging.

The low keeping quality of the flour is largely caused by the rapid development of lipid rancidity due to the activities of rancidity-causing enzymes such as lipase, lipoxygenase, peroxidase, and polyphenol oxidase. Additional factors including oxygen, light, high temperature and high humidity storage conditions, exacerbate the problem. Lipase and esterified lipids in cells come in contact with each other due to rupturing of cells, during milling of pearl millet. During this time, the lipase leads to the stepwise hydrolysis of the triacylglycerols, and membrane lipids to create unesterified fatty acids. Since unsaturated fatty acids are in abundance and are amphipathic, they are more prone to oxidation in presence of oxygen and moisture, resulting in rapid deterioration of pearl millet flour quality, which thereby causes off flavour and reduces the shelf life of the pearl millet flour. Therefore, pearl millet flour tends to quickly become unsuitable for human consumption due to high rancidity and off odour during increased storage time.

There are various physiochemical treatments, such as, decortication, dry heat, different packaging procedures, blanching, acid treatment, toasting and boiling, low temperature storage, microwave, available for storing the milled flour. Further, several attempts are made on reducing the rancidity in the milled flour by deploying a combination of different pre-processing options such as High-density polyethylene (HDPE) packaging and refrigeration, combination of fermentation and malting.

However, none of these processes has proven to be universally effective and broadly applied. Therefore, there is a dire need in the art to develop pearl millet varieties that yield flours with reduced rancidity, improved shelf life stability, and flavour.

SUMMARY OF THE INVENTION

In an aspect of the present disclosure, there is provided a food product made from millet having reduced rancidity, wherein the millet comprises a mutant gene encoding a PgTAG Lipase with reduced triacylglycerol (TAG) lipase activity. In a preferred embodiment, the millet seed or grain has reduced TAG lipase activity and the food product is reduced-rancidity flour or meal made from such seed or grain.

The present disclosure is based, at least in part, on the surprising discovery that rancidity can be reduced in food products made from millet comprising reduced activity of the TAG lipase of SEQ ID NO:2 or SEQ ID NO:4. Thus, in one aspect, the present disclosure provides a food product comprising millet, wherein the millet (e.g., the millet seed or grain) comprises a polynucleotide that: a) encodes a modified polypeptide of SEQ ID NO:2 or SEQ ID NO: 4, wherein the modification of SEQ ID NO:2 or SEQ ID NO:4 reduces or eliminates its TAG lipase activity, b) encodes a polypeptide having a mutation in SEQ ID NO: 2, wherein the mutation is a substitution, deletion, or insertion at one or more of amino acid positions 12, 18, 19, 20, 23, 26, 37, 38, 42, 43, 44, 96, 97, 98, 114, 131, 135, 144, 145, 146, 167, 168, 169, 172, 205, 206, 215, 221, 222, 237, 246, 263, 289, 290, 298, 299, 330, 339, or 346 of SEQ ID NO: 2; c) encodes a polypeptide having a mutation in SEQ ID NO: 4, wherein the mutation is a substitution, deletion, or insertion at one or more of amino acid positions 220, 223, 265, 316, 317, 318, 319, 320, 321, 322, 323, 324, 325, 326, 327, 328, 329, 330, 331, or 332 of SEQ ID NO: 4; d) encodes a polypeptide having an amino acid position as set forth in SEQ ID NO: 7; e) encodes a polypeptide having an amino acid sequence as set forth in SEQ ID NO: 13; SEQ ID NO: 15, SEQ ID NO: 17, SEQ ID NO: 19, SEQ ID NO: 21, and SEQ ID NO: 25; f) has a nucleotide sequence as set forth in SEQ ID NO: 22; g) encodes a polypeptide having an amino acid sequence as set forth in SEQ ID NO: 9, and SEQ ID NO: 11; h) has a nucleotide sequence selected from the group having the sequence as set forth in SEQ ID NO: 26, SEQ ID NO: 28, and SEQ ID NO: 30; or i) encodes (1) a sense strand of at least 20 contiguous nucleotides of a polynucleotide encoding a polypeptide having an amino acid sequence as set forth in SEQ ID NO: 2 or SEQ ID NO: 4, (2) a spacer polynucleotide; and (3) an antisense strand that is complementary to the sense strand. In a preferred example, each of the foregoing food product is millet flour or meal having reduced rancidity.

In another aspect, the present disclosure provides an isolated polynucleotide encoding a polypeptide, wherein the polynucleotide: a) encodes a modified polypeptide of SEQ ID NO:2 or SEQ ID NO:4, wherein the modification of SEQ ID NO:2 or SEQ ID NO:4 reduces or eliminates its TAG lipase activity, b) encodes a polypeptide referred to hereafter as “Mut-PgTAGLip1”, which is SEQ ID NO: 2 modified to include a substitution, deletion, or insertion at one or more of amino acid positions 12, 18, 19, 20, 23, 26, 37, 38, 42, 43, 44, 96, 97, 98, 114, 131, 135, 144, 145, 146, 167, 168, 169, 172, 205, 206, 215, 221, 222, 237, 246, 263, 289, 290, 298, 299, 330, 339, and 346 of SEQ ID NO: 2; c) encodes a polypeptide referred to hereafter as “Mut-PgTAGLip2” which is SEQ ID NO: 4 modified to include a substitution, deletion or insertion at one or more of amino acid positions 220, 223, 265, 316, 317, 318, 319, 320, 321, 322, 323, 324, 325, 326, 327, 328, 329, 330, 331, and 332 of SEQ ID NO: 4; d) encodes a polypeptide having an amino acid position as set forth in SEQ ID NO: 7; e) encodes a polypeptide having an amino acid sequence as set forth in SEQ ID NO: 13; SEQ ID NO: 15, SEQ ID NO: 17, SEQ ID NO: 19, SEQ ID NO: 21, and SEQ ID NO: 25; f) has a nucleotide sequence as set forth in SEQ ID NO: 22; g) encodes a polypeptide having an amino acid sequence as set forth in SEQ ID NO: 9, and SEQ ID NO: 11; or h) has a nucleotide sequence selected from the group having the sequence as set forth in SEQ ID NO: 26, SEQ ID NO: 28, and SEQ ID NO:30.

In another aspect, the present disclosure provides a recombinant construct comprising a heterologous promoter (e.g., a seed-preferred promoter) operably linked to the isolated polynucleotide, said isolated polynucleotide encoding a polypeptide, wherein the polynucleotide: a) encodes a modified polypeptide of SEQ ID NO:2 or SEQ ID NO:4, wherein the modification of SEQ ID NO:2 or SEQ ID NO:4 reduces or eliminates its TAG lipase activity, b) encodes Mut-PgTAGLip1 disclosed herein; c) encodes Mut-PgTAGLip2 disclosed herein; d) encodes a polypeptide having an amino acid position as set forth in SEQ ID NO: 7; e) encodes a polypeptide having an amino acid sequence as set forth in SEQ ID NO: 13; SEQ ID NO: 15, SEQ ID NO: 17, SEQ ID NO: 19, SEQ ID NO: 21, and SEQ ID NO: 25; f) has a nucleotide sequence as set forth in SEQ ID NO: 22; g) encodes a polypeptide having an amino acid sequence as set forth in SEQ ID NO: 9, and SEQ ID NO: 11; or h) has a nucleotide sequence selected from the group having the sequence as set forth in SEQ ID NO: 26, SEQ ID NO: 28, and SEQ ID NO:30. In a further aspect, the present disclosure provides a recombinant host cell comprising the recombinant construct as described herein.

In another aspect, the present disclosure provides a recombinant vector comprising the recombinant construct, said DNA construct comprising a heterologous promoter (e.g., a seed-preferred promoter) operably linked to the isolated polynucleotide, said isolated polynucleotide encoding a polypeptide, wherein the polynucleotide: a) encodes a modified polypeptide of SEQ ID NO: 2 or SEQ ID NO:4, wherein the modification of SEQ ID NO:2 or SEQ ID NO:4 reduces or eliminates its TAG lipase activity, b) encodes Mut-PgTAGLip1 disclosed herein; c) encodes Mut-PgTAGLip2 disclosed herein; d) encodes a polypeptide having an amino acid position as set forth in SEQ ID NO: 7; e) encodes a polypeptide having an amino acid sequence as set forth in SEQ ID NO: 13; SEQ ID NO: 15, SEQ ID NO: 17, SEQ ID NO: 19, SEQ ID NO: 21, and SEQ ID NO: 25; f) has a nucleotide sequence as set forth in SEQ ID NO: 22; g) encodes a polypeptide having an amino acid sequence as set forth in SEQ ID NO: 9, and SEQ ID NO: 11; or h) has a nucleotide sequence selected from the group having the sequence as set forth in SEQ ID NO: 26, SEQ ID NO: 28, and SEQ ID NO:30. In a further aspect, the present disclosure provides a recombinant host cell comprising the recombinant vector as described herein.

In another aspect, the present disclosure provides a gene-edited or transgenic plant (e.g., millet), plant tissue (e.g. seed or grain), or cell thereof having reduced lipase activity comprising a polynucleotide that: a) has been altered to encode a modified polypeptide of SEQ ID NO: 2 or SEQ ID NO:4, wherein the modification of SEQ ID NO:2 or SEQ ID NO:4 reduces or eliminates its TAG lipase activity, b) encodes Mut-PgTAGLip1 disclosed herein; c) encodes Mut-PgTAGLip2 disclosed herein; d) encodes a polypeptide having an amino acid position as set forth in SEQ ID NO: 7; e) encodes a polypeptide having an amino acid sequence as set forth in SEQ ID NO: 13; SEQ ID NO: 15, SEQ ID NO: 17, SEQ ID NO: 19, SEQ ID NO: 21, and SEQ ID NO: 25; f) has a nucleotide sequence as set forth in SEQ ID NO: 22; g) encodes a polypeptide having an amino acid sequence as set forth in SEQ ID NO: 9, and SEQ ID NO: 11; h) has a nucleotide sequence selected from the group having the sequence as set forth in SEQ ID NO: 26, SEQ ID NO: 28, and SEQ ID NO:30; or i) encodes (1) a sense strand of at least 20 contiguous nucleotides of a polynucleotide encoding a polypeptide having an amino acid sequence as set forth in SEQ ID NO: 2 or SEQ ID NO: 4, (2) a spacer polynucleotide; and (3) an antisense strand that is complementary to the sense strand.

In another aspect of the present disclosure, there is provided a recombinant construct referred to herein as “Antisense Construct” comprising a heterologous promoter (e.g., a seed-preferred promoter) operably linked to sequence encoding: a) a sense strand of at least 20 contiguous nucleotides of a polynucleotide encoding a polypeptide having an amino acid sequence as set forth in SEQ ID NO: 2 or SEQ ID NO: 4; b) a spacer polynucleotide; and c) an antisense strand that is complementary to the sense strand of a). In a further aspect, the present disclosure provides a recombinant vector comprising the Antisense Construct.

Additionally, the present disclosure provides a recombinant host cell or a transgenic plant having reduced lipase activity, wherein the host cell or transgenic plant comprise the Antisense Construct or recombinant vector as described herein.

In another aspect, the present disclosure provides a method for obtaining a transgenic plant having reduced lipase activity, said method comprising: a) obtaining a recombinant construct as described herein, or obtaining a recombinant vector as described herein; b) transforming a host cell with the recombinant construct of step (a) or with the recombinant vector of step (a), to obtain a recombinant host cell; c) transforming an explant with the recombinant construct or recombinant host cell, to obtain putative transformants; and d) screening the putative transformants to obtain transgenic plant having reduced lipase activity.

In another aspect, the present disclosure provides a recombinant construct hereafter referred to as an "gRNA Construct" comprising: a) a heterologous promoter (e.g., a seed-preferred promoter) operably linked to one or more guide polynucleotides (e.g., a polynucleotide encoding one or more guide RNA (gRNA) sequences), wherein the guide polynucleotide has at least 10 contiguous nucleotides (such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or 20-25 nucleotides in length or about 12, 13, 14, 15, 16, 18, 19, 20, 21, 22, 23, 24, 25 or more nucleotides) that are identical or complementary to a target polynucleotide, wherein the target polynucleotide: i) has a nucleotide sequence as set forth in SEQ ID NO: 1; or ii) encodes a polypeptide having the amino acid sequence as set forth in SEQ ID NO: 2; or iii) has nucleotides from 663 to 692 of SEQ ID NO: 1; or iv) has the nucleotide sequence as set forth in SEQ ID NO: 3; or v) encodes a polypeptide having the amino acid sequence as set forth in SEQ ID NO: 4; or vi) has nucleotides from 531 to 561 of SEQ ID NO: 3. In another aspect, the present disclosure provides a recombinant host cell comprising the gRNA Construct and a Cas endonuclease, wherein the expression from the gRNA Construct provides one or more guide polynucleotides which together with the Cas endonuclease form a guide polynucleotide/Cas endonuclease complex, wherein said complex binds to and cleaves the target polynucleotide. In one example, the Cas endonuclease is expressed from a construct comprising a heterologous promoter (e.g., a seed-preferred promoter) operably linked to a polynucleotide encoding a Cas endonuclease in the recombinant host cell. Alternatively, guide polynucleotides, such as gRNA(s), Cas endonuclease, or both can be delivered to the host cell by transfection or with the aid of cell penetrating peptides.

In another aspect, the present disclosure provides a method for obtaining a gene edited millet plant having reduced lipase activity, said method comprising: a) providing the gRNA Construct disclosed herein to a millet plant cell having a Cas endonuclease, b) expressing the one or more guide polynucleotides to form a complex with the Cas endonuclease that enables the Cas endonuclease to introduce a targeted mutation in the plant cell's genome; and c) generating a gene edited millet plant from the plant cell comprising the targeted mutation. The method can further comprise screening the gene edited millet plant for reduced lipase activity. In certain examples of this method, the gRNA Construct can be expressed in a millet plant cell having the Cas endonuclease and a desirable fatty acid profile genotype (e.g., high oleic acid content due to a mutant fatty acid desaturase gene such as FAD2) and used to generate a plant having reduced lipase activity and desirable fatty acid (e.g., FAD2) profile. Desirable fatty acid profiles can be conferred by mutations in the FAD2a sequence Accession No. Pgl_GLEAN_10011765 or FAD2b sequence Accession No. Pgl_GLEAN_10010027. FAD2 Sequences at *Pennisetum glaucum* reference genome assembly (see Varsney et al. *Nature Biotechnology* 35(10):969-976 (2017)). Oleic acid is a mono-unsaturated fatty acid that is less prone to oxidation than linoleic acid, which is the most abundant fatty acid in wildtype millet. Pearl millet genome sequence provides a resource to improve agronomic traits in arid environments. (Varsney et al. 2017).

In another aspect, the present disclosure provides the gene edited millet e.g., pearl millet) plant having reduced lipase activity as disclosed herein, which gene edited plant is generated using the foregoing method.

In a further aspect, the present disclosure provides a food product from the transgenic plant or the gene edited millet plant as described herein. In preferred aspect, the food product is flour or meal generated from the millet seed or grain disclosed herein which has reduced lipase activity.

In another aspect, the present disclosure provides a method of detecting or identifying one or more millet (e.g., pearl millet) plants with reduced lipase activity, said method referred to herein as the "First Detection/Identification Method" comprises: a) obtaining nucleic acid from one or more millet plants; and b) detecting in each nucleic acid a polynucleotide sequence: i) encoding a mutation or modification in the polypeptide of SEQ ID NO: 2, wherein the mutation or modification of SEQ ID NO: 2 reduces or eliminates its TAG lipase activity, ii) encoding a polypeptide having one or more substitutions, insertions or deletions at amino acid positions 12, 18, 19, 20, 23, 26, 37, 38, 42, 43, 44, 96, 97, 98, 114, 131, 135, 144, 145, 146, 167, 168, 169, 172, 205, 206, 215, 221, 222, 237, 246, 263, 289, 290, 298, 299, 330, 339, or 346 of SEQ ID NO: 2; iii) encoding a polypeptide having an amino acid sequence as set forth in SEQ ID NO: 7; iv) encoding a polypeptide having an amino acid sequence as set forth in SEQ ID NO: 13; SEQ ID NO: 15, SEQ ID NO: 17, SEQ ID NO: 19, SEQ ID NO: 21, SEQ ID NO: 23, or SEQ ID NO: 25; v) having a nucleotide sequence as set forth in SEQ ID NO: 12; SEQ ID NO: 14, SEQ ID NO: 16, SEQ ID NO: 18, SEQ ID NO: 20, SEQ ID NO: 22, or SEQ ID NO: 24. The presence of this polynucleotide sequence indicates the millet (e.g., pearl millet) comprises reduced lipase activity. In some examples, a plurality of millet plants are screened for the presence of this polynucleotide sequence, and millet plants in which this polynucleotide sequence is detected are selected for breeding or for producing a food product.

In another aspect, the present disclosure provides a method of detecting or identifying one or more millet (e.g., pearl millet) plants with reduced lipase activity, said method referred to herein as the "Second Detection/Identification Method" comprises: a) obtaining nucleic acid from one or more millet plants; and b) detecting in each nucleic acid a polynucleotide sequence: i) encoding a mutation or modification in the polypeptide of SEQ ID NO: 2, wherein the mutation or modification of SEQ ID NO: 4 reduces or eliminates its TAG lipase activity, ii) encoding a polypeptide having one or more substitutions, insertions or deletions at amino acid positions 220, 223, 265, 316, 317, 318, 319, 320, 321, 322, 323, 324, 325, 326, 327, 328, 329, 330, 331, or 332 of SEQ ID NO: 4; ii) encoding a polypeptide having an amino acid sequence as set forth in SEQ ID NO: 9, and SEQ ID NO: 11; iii) encoding a polypeptide having an amino acid sequence as set forth in SEQ ID NO: 27; SEQ ID NO: 29, or SEQ ID NO: 31; or (iv) having a nucleotide sequence selected from the group having the sequence as set forth in SEQ ID NO: 26, SEQ ID NO: 28, and SEQ ID NO:30. The presence of the polynucleotide sequence indicates the millet (e.g., pearl millet) comprises reduced lipase activity. The presence of this polynucleotide sequence indicates the millet (e.g., pearl millet) comprises reduced lipase activity. In some examples, a plurality of millet plants are screened for the presence of this polynucleotide sequence, and millet plants in which this polynucleotide sequence is detected are selected for breeding or for producing a food product.

In another aspect, the present disclosure provides a method of using markers to detect or identify one or more millet (e.g., pearl millet) plants with reduced lipase activity, said method referred to herein as the "RE-Site Marker Detection/Identification Method" comprises: a) obtaining nucleic acid from one or more millet plants; and b) amplifying sequence from the nucleic acid using cleaved amplified polymorphic sequences ("CAPS") primers or derived cleaved amplified polymorphic sequences ("dCAPS") primers to produce amplified sequence c) contacting the amplified sequence with a restriction enzyme (RE) that distinguishes the presence of absence of a RE-site in amplified sequence, wherein the presence or absence of the RE-site in the amplified product distinguishes between nucleic obtained from a millet with reduced lipase activity and that obtained from a millet with wild type lipase activity. Suitable CAPS primers, dCAPS primers, restriction enzymes and diagnostic restriction fragments are described herein, e.g., in the Examples, including Tables 16 and 17. In some examples, a plurality of millet plants are screened using the RE-Site Marker Detection/Identification Method, and millet plants in which the presence or absence of the RE-site indicates reduced lipase activity are selected for breeding or for producing a food product.

In another aspect, the present disclosure provides a method of producing a millet (e.g., pearl millet) plant with reduced lipase activity, said method comprises: a) using the First Detection/Identification Method, the Second Detection/Identification Method or the RE-Site Marker Detection/Identification Method disclosed herein to identify one or more millet plants with sequence(s) indicative of reduced lipase activity; b) crossing the identified plant having the detected mutant sequence (first parent) with a second plant (second parent) to obtain a progeny plant; and c) obtaining seeds from the progeny plant of step (b); and d) producing millet plant from said seeds, wherein said plant produced from said seeds comprises the one or more detected mutant sequences. In particular examples, the first parent and second parent are hybrid parental lines, the progeny plant is a hybrid, and the seed is hybrid seed. In some examples, the second parent provides desirable agronomic qualities that are not provided by the first parent millet plant.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

Figure 3:
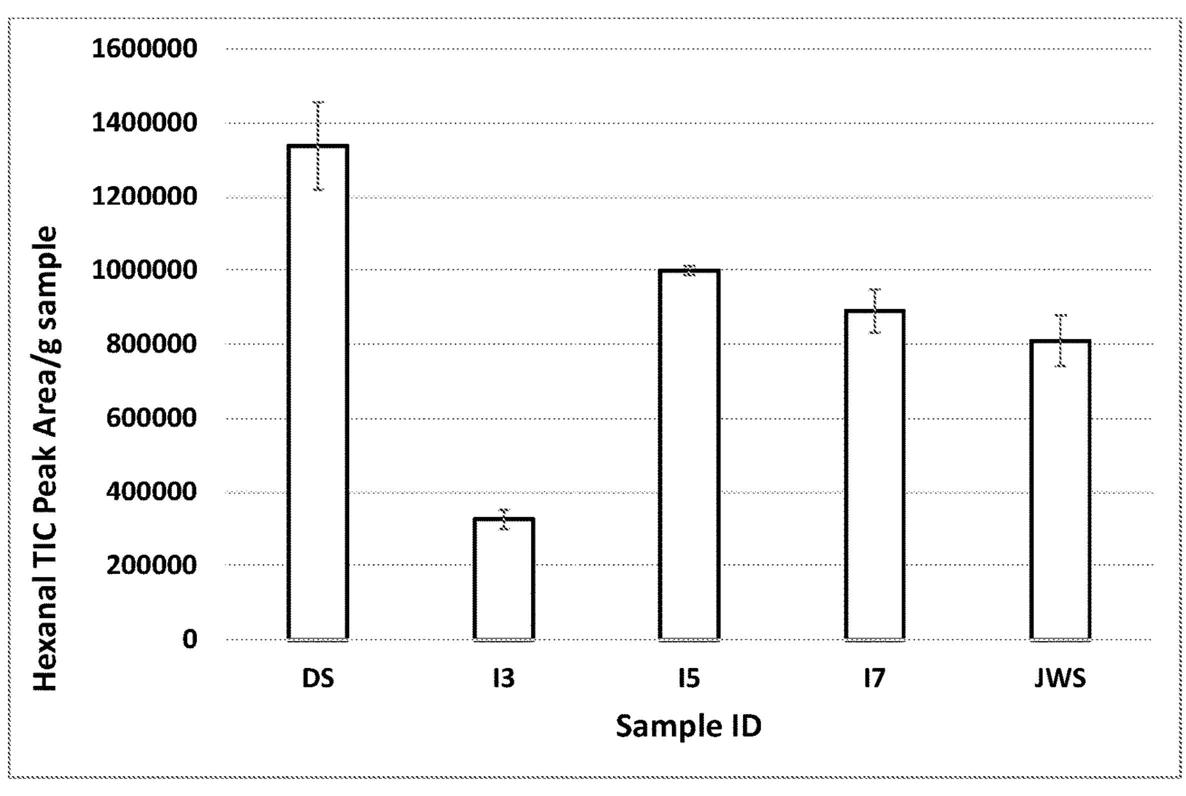

FIG. 3 depicts hexanal Peak Area (corrected for sample weight) determined by SPME Headspace Analysis of ground flours. Values are means of three technical replicates, error bars indicate the standard deviations. Samples were analyzed after 21 Days of accelerated aging (35° C. and 71% relative humidity).

Figure 4:
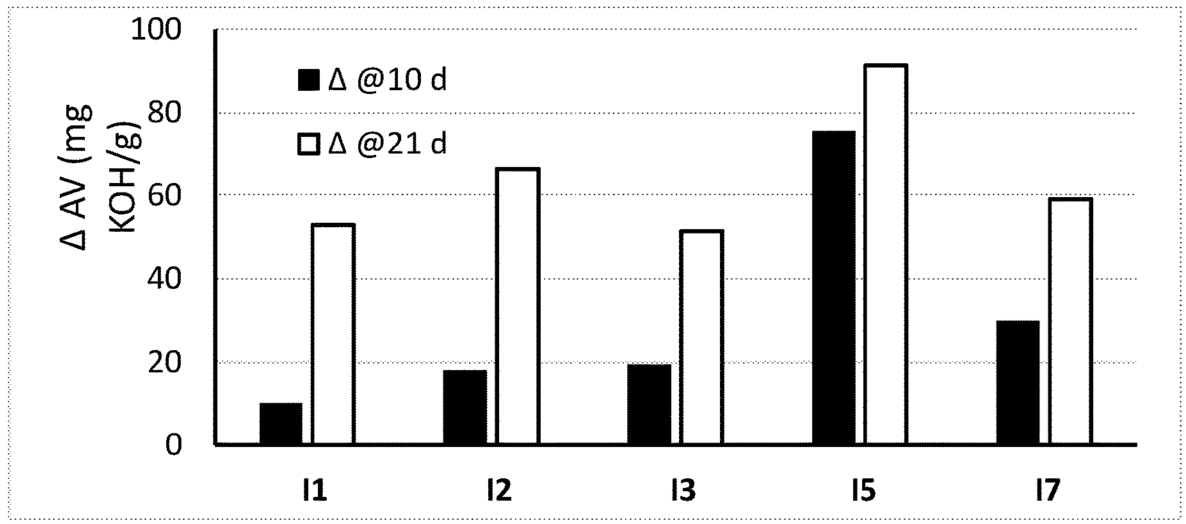

FIG. 4 depicts changes (delta) in the Acid Value (AV) in the pearl millet flour under accelerated storage conditions (35±0.5° C.; RH 75%) on day 10 and 21.

Figure 5:
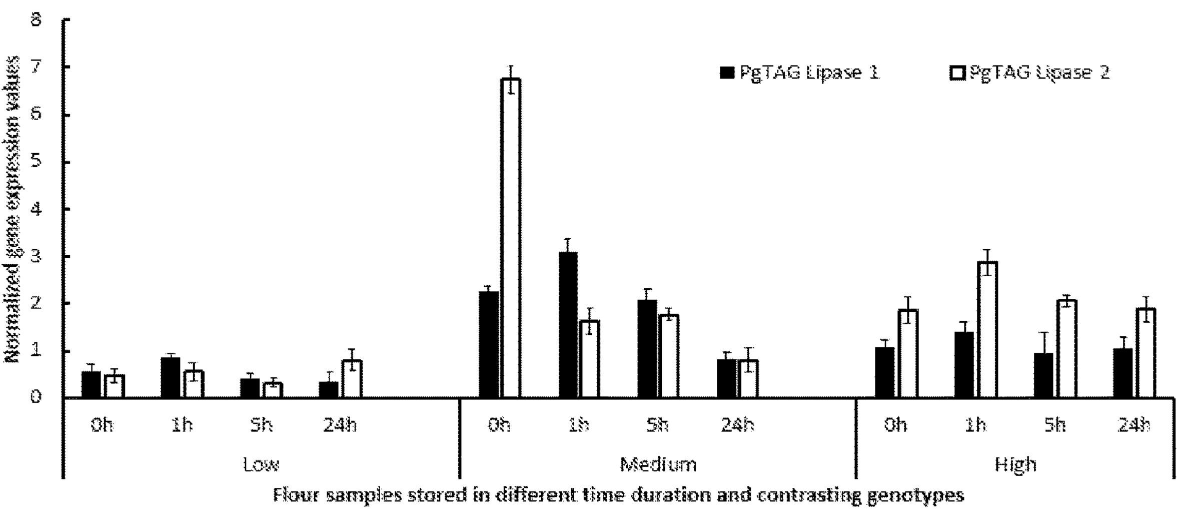

FIG. 5 depicts expression of PgTAG Lipases in milled flour stored for different time intervals in pearl millet lines with contrasting propensity (Low, Medium, and High) to develop rancidity, as measured by qRT-PCR. Data points represent the expression values obtained after normalization against the reference gene, eukaryotic initiation factor4α (PgEIF4α). Each data point represents the mean of three biological replications with standard error (±SE). Each biological replication represents the mean of three technical replications.

Figure 6:
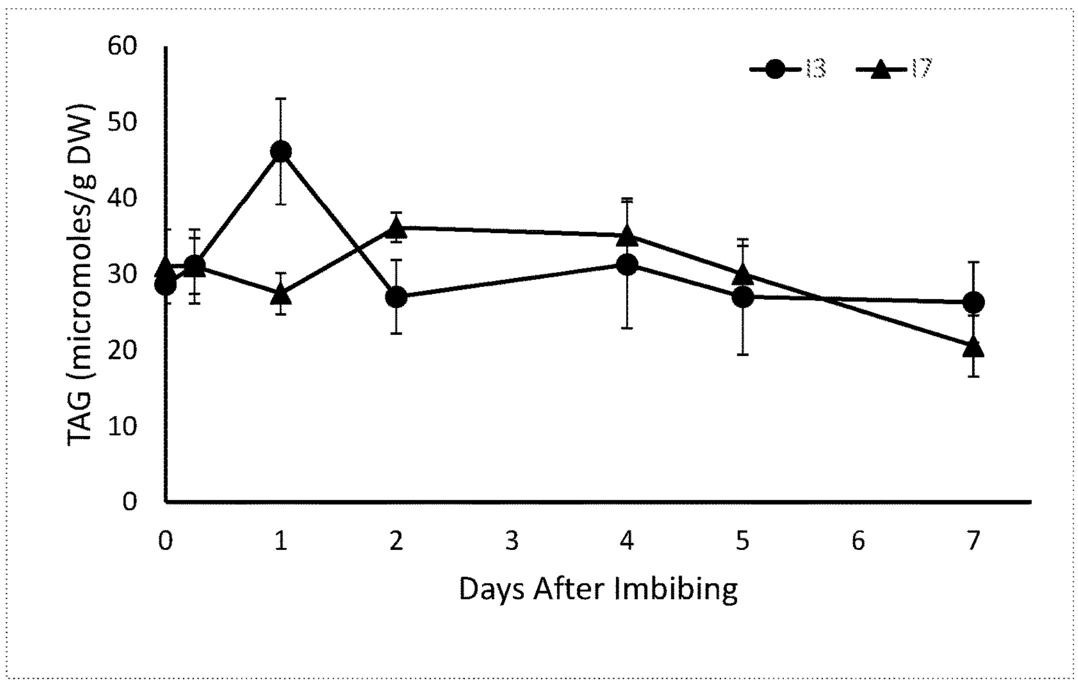

FIG. 6 depicts mobilization of triacylglycerol (TAG) during germination. Error bars are standard deviation of 3 replicates.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Sequences listing description. Nucleic acid sequences listed in the accompanying sequence listing and referenced herein are shown using standard letter abbreviations for nucleotide bases. Only one strand of each nucleic acid sequence is shown, but the complementary strand is understood to be included by any reference to the displayed strand.

SEQ ID NO: 1 depicts the nucleotide sequence of PgTAGLip1 gene coding region (cDNA).

SEQ ID NO: 2 depicts the amino acid sequence of PgTAGLIP1.

SEQ ID NO: 3 depicts the nucleotide sequence of PgTAGLip2 gene coding region (cDNA).

SEQ ID NO: 4 depicts the amino acid sequence of PgTAGLIP2.

SEQ ID NO: 5 depicts the nucleotide sequence of PgTAGLip1 mutant (cDNA) having 1061 bp.

SEQ ID NO: 6 depicts the nucleotide sequence of PgTAGLip1 mutant (cDNA) having 528 bp.

SEQ ID NO: 7 depicts the amino acid sequence of the PgTAGLIP1 mutant variant.

SEQ ID NO: 8 depicts the nucleotide sequence of a mutant of PgTAGLip2.

SEQ ID NO: 9 depicts the amino acid sequence of a mutant of PgTAGLIP2.

SEQ ID NO: 10 depicts the nucleotide sequence of a mutant of PgTAGLip2.

SEQ ID NO: 11 depicts the amino acid sequence of a mutant of PgTAGLIP2.

SEQ ID NO: 12 depicts the nucleotide sequence having 84 bp insertion at 89 nucleotide position of PgTAGLip1.

SEQ ID NO: 13 depicts the amino acid sequence having an insertion at 30th amino acid position of PgTAGLIP1.

SEQ ID NO: 14 depicts the nucleotide sequence having deletion of 17 bp nucleotides (269-285) in PgTAGLip1 gene.

SEQ ID NO: 15 depicts the amino acid sequence having deletion of 6 amino acids (CNDLTR) at 90-95 position of PgTAGLIP1.

SEQ ID NO: 16 depicts the nucleotide sequence having 116 bp insertion at 287 nucleotide position of PgTAGLip1.

SEQ ID NO: 17 depicts the amino acid sequence having an insertion at the 96th position (V*) of PgTAGLIP1.

SEQ ID NO: 18 depicts the nucleotide sequence having 155 bp deletion (269-423) in PgTAGLip1 gene.

SEQ ID NO: 19 depicts the amino acid sequence having a deletion of 51 amino acids (91-141 bp) in PgTAGLIP1.

SEQ ID NO: 20 depicts the nucleotide sequence having 90 bp nucleotide deletion (331-420) in PgTAGLip1 gene.

SEQ ID NO: 21 depicts the amino acid sequence having deletion of 30 amino acids (111-140) in PgTAGLIP1.

SEQ ID NO: 22 depicts the nucleotide sequence having 7 bp nucleotide deletion (490-496) in PgTAGLip1 gene.

SEQ ID NO: 23 depicts the amino acid sequence having deletion of two amino acids (Serine and Isoleucine) at 164-165th position of PgTAGLIP1.

SEQ ID NO: 24 depicts the nucleotide sequence having deletion of 49b nucleotide (563-611) in PgTAGlip1 gene.

SEQ ID NO: 25 depicts the amino acid sequence having deletion of 16 amino acids (189-224) in PgTAGLIP1.

SEQ ID NO: 26 depicts the nucleotide sequence having 6 bp insertion at 33 bp in PgTAGLip2 gene.

SEQ ID NO: 27 depicts the amino acid sequence having insertion of 2 amino acids at $11^{th}$ position in PgTAGLIP2.

SEQ ID NO: 28 depicts the nucleotide sequence having 3 bp insertion at 32 bp PgTAGLip2 gene.

SEQ ID NO: 29 depicts the amino acid sequence having an insertion of one amino acid at 12th position in PgTAGLIP2.

SEQ ID NO: 30 depicts the nucleotide sequence having an insertion of 6 nucleotide at $80^{th}$ position in PgTAGLip2 gene.

SEQ ID NO: 31 depicts the amino acid sequence having an insertion of 2 amino acids at $28^{th}$ position in PgTAGLIP2.

SEQ ID NO: 32 depicts the nucleotide sequence of primer PgTAGLip1_F1.

SEQ ID NO: 33 depicts the nucleotide sequence of primer PgTAGLip1_R1.

SEQ ID NO: 34 depicts the nucleotide sequence of primer PgTAGLip1_R2.

SEQ ID NO: 35 depicts the nucleotide sequence of primer PgTAGLip1_R3.

SEQ ID NO: 36 depicts the nucleotide sequence of primer PgTAGLip1_qF1.

SEQ ID NO: 37 depicts the nucleotide sequence of primer PgTAGLip1_qR1.

SEQ ID NO: 38 depicts the nucleotide sequence of primer PgTAGLip1_qF2.

SEQ ID NO: 39 depicts the nucleotide sequence of primer PgTAGLip1_qR2.

SEQ ID NO: 40 depicts the nucleotide sequence of primer PgTAGLip1_qF3.

SEQ ID NO: 41 depicts the nucleotide sequence of primer PgTAGLip1_qR3.

SEQ ID NO: 42 depicts the nucleotide sequence of primer PgEif4a_qF4.

SEQ ID NO: 43 depicts the nucleotide sequence of primer PgEif4a_qR4.

SEQ ID NO: 44 depicts the nucleotide sequence of primer PgTAGLip1_RNAi_SF.

SEQ ID NO: 45 depicts the nucleotide sequence of primer PgTAGLip1_RNAi_SR.

SEQ ID NO: 46 depicts the nucleotide sequence of primer PgTAGLip1_RNAi_ASF.

SEQ ID NO: 47 depicts the nucleotide sequence of primer PgTAGLip1_RNAi_ASR.

SEQ ID NO: 48 depicts the nucleotide sequence of primer PgTAGLip2_F1.

SEQ ID NO: 49 depicts the nucleotide sequence of primer PgTAGLip2_R1.

SEQ ID NO: 50 depicts the nucleotide sequence of primer PgTAGLip2_R2.

SEQ ID NO: 51 depicts the nucleotide sequence of primer PgTAGLip2_R3.

SEQ ID NO: 52 depicts the nucleotide sequence of primer PgTAGLip2_qF1.

SEQ ID NO: 53 depicts the nucleotide sequence of primer PgTAGLip2_qR1.

SEQ ID NO: 54 depicts the nucleotide sequence of primer PgTAGLip2_qF2.

SEQ ID NO: 55 depicts the nucleotide sequence of primer PgTAGLip2_qR2.

SEQ ID NO: 56 depicts the nucleotide sequence of primer PgTAGLip2_qF3.

SEQ ID NO: 57 depicts the nucleotide sequence of primer PgTAGLip2_qR3.

SEQ ID NO: 58 depicts the nucleotide sequence of primer PgEif4a_qF4.

SEQ ID NO: 59 depicts the nucleotide sequence of primer PgEif4a_qR4.

SEQ ID NO: 60 depicts the nucleotide sequence of sense strand (139-158 bp).

SEQ ID NO: 61 depicts the nucleotide sequence of anti-sense strand (348-367 bp).

SEQ ID NO: 62 depicts the nucleotide sequence of sense strand (500-519 bp).

SEQ ID NO: 63 depicts the nucleotide sequence of sense strand (670-689 bp).

SEQ ID NO: 64 depicts the nucleotide sequence of anti-sense strand (728-747 bp).

SEQ ID NO: 65 depicts the nucleotide sequence of sense strand (922-941 bp).

SEQ ID NO: 66 depicts the nucleotide sequence of Pdk intron.

SEQ ID NO: 67 depicts the nucleotide sequence of chsA intron.

SEQ ID NO: 68 depicts the nucleotide sequence of PgTAGLip1 sense sequence.

SEQ ID NO: 69 depicts the nucleotide sequence of PgTAGLip1 antisense sequence.

SEQ ID NO: 70 depicts the nucleotide sequence of PgTAGLip2 sense sequence.

SEQ ID NO: 71 depicts the nucleotide sequence of PgTAGLip2 antisense sequence.

SEQ ID NO: 72 depicts the nucleotide sequence of anti-sense strand (115-134 bp).

SEQ ID NO: 73 depicts the nucleotide sequence of sense strand (270-289 bp).

SEQ ID NO: 74 depicts the nucleotide sequence of anti-sense strand (415-434 bp).

SEQ ID NO: 75 depicts the nucleotide sequence of sense strand (534-553 bp).

SEQ ID NO: 76 depicts the nucleotide sequence of sense strand (773-792 bp).

SEQ ID NO: 77 depicts the nucleotide sequence of sense strand (991-1010 bp).

SEQ ID NO: 78 depicts the nucleotide sequence of PgTAGLip1_F (dCAPs marker).

SEQ ID NO: 79 depicts the nucleotide sequence of PgTAGLip1_R (dCAPs marker).

SEQ ID NO: 80 depicts the nucleotide sequence of PgTAGLip1_F (CAPS marker).

SEQ ID NO: 81 depicts the nucleotide sequence of PgTAGLip1_R (CAPS marker).

SEQ ID NO: 82 depicts the nucleotide sequence of PgTAGLip1_F1 (Indel marker).

SEQ ID NO: 83 depicts the nucleotide sequence of PgTAGLip1_R1 (Indel marker).

SEQ ID NO: 84 depicts the nucleotide sequence of PgTAGLip1_F2 (Indel marker).

SEQ ID NO: 85 depicts the nucleotide sequence of PgTAGLip1_R2 (Indel marker).

SEQ ID NO: 86 depicts the nucleotide sequence of PgTAGLip1_F3 (Indel marker).

SEQ ID NO: 87 depicts the nucleotide sequence of PgTAGLip1_R3 (Indel marker).

SEQ ID NO: 88 depicts the nucleotide sequence of PgTAGLip2_F (dCAPs marker).

SEQ ID NO: 89 depicts the nucleotide sequence of PgTAGLip2_R (dCAPs marker).

SEQ ID NO: 90 depicts the nucleotide sequence of PgTAGLip2_F (CAPs marker).

SEQ ID NO: 91 depicts the nucleotide sequence of PgTAGLip2_R (CAPs marker).

SEQ ID NO: 92 depicts the nucleotide sequence of PgTAGLip2_F (Indel marker).

SEQ ID NO: 93 depicts the nucleotide sequence of PgTAGLip2_R (Indel marker).

SEQ ID NO: 94 depicts the nucleotide sequence of primer PgTAGLip1_F for identifying mutations in PgTAGLip1 gene.

SEQ ID NO: 95 depicts the nucleotide sequence of primer PgTAGLip1_R for identifying mutations in PgTAGLip1 gene.

SEQ ID NO: 96 depicts the nucleotide sequence of primer PgTAGLip1_2F for identifying mutations in PgTAGLip1 gene.

SEQ ID NO: 97 depicts the nucleotide sequence of primer PgTAGLip1_2R for identifying mutations in PgTAGLip1 gene.

SEQ ID NO: 98 depicts the nucleotide sequence of primer PgTAGLip1_3F for identifying mutations in PgTAGLip1 gene.

SEQ ID NO: 99 depicts the nucleotide sequence of primer PgTAGLip1_3R for identifying mutations in PgTAGLip1 gene.

SEQ ID NO: 100 depicts the nucleotide sequence of primer PgTAGLip2_F for identifying mutations in PgTAGLip2 gene.

SEQ ID NO: 101 depicts the nucleotide sequence of primer PgTAGLip2_R for identifying mutations in PgTAGLip2 gene.

SEQ ID NO: 102 depicts the nucleotide sequence of primer PgTAGLip2_1F for identifying mutations in PgTAGLip2 gene.

SEQ ID NO: 103 depicts the nucleotide sequence of primer PgTAGLip2_1R for identifying mutations in PgTAGLip2 gene.

SEQ ID NO: 104 depicts the nucleotide sequence of primer PgTAGLip2_2F for identifying mutations in PgTAGLip2 gene.

SEQ ID NO: 105 depicts the nucleotide sequence of primer PgTAGLip2_2R for identifying mutations in PgTAGLip2 gene.

SEQ ID NO: 106 depicts the nucleotide sequence of primer PgTAGLip1 gRNAseq_F

SEQ ID NO: 107 depicts the nucleotide sequence of primer PgTAGLip1 gRNAseq_F

SEQ ID NO: 108 depicts the nucleotide sequence of primer PgTAGLip2 gRNAseq_F

SEQ ID NO: 109 depicts the nucleotide sequence of primer PgTAGLip2 gRNAseq_R

SEQ ID NO: 110 depicts the nucleotide sequence of primer nptII_ConF

SEQ ID NO: 111 depicts the nucleotide sequence of primer nptII_ConR

SEQ ID NO: 112 depicts the nucleotide sequence of primer Hpt_F

SEQ ID NO: 113 depicts the nucleotide sequence of primer Hpt_R

Definitions

For convenience, certain terms employed in the specification and examples are delineated here. These definitions should be read in the light of the remainder of the disclosure and understood as by a person of skill in the art.

The articles “a”, “an” and “the” are used to refer to one or to more than one (i.e., to at least one) of the grammatical object of the article.

The terms “comprise” and “comprising” are used in the inclusive, open sense, meaning that additional elements may be included. It is not intended to be construed as “consists of only”.

Throughout this specification, unless the context requires otherwise the word “comprise”, and variations such as “comprises” and “comprising”, will be understood to imply the inclusion of a stated element or step or group of element or steps but not the exclusion of any other element or step or group of element or steps.

The term “including” is used to mean “including but not limited to”. “Including” and “including but not limited to” are used interchangeably.

As used herein, the term “mutant” in connection with a gene or sequence refers to a gene or sequence comprising one or more mutation relative to the corresponding normal, non-mutated cellular gene or sequence (the latter referred to herein as the “wild-type” gene or sequence). A mutant sequence can encompass any variant of a normal cellular gene, gene product, or gene fragment whose expression is associated lipase activity and/or rancidity.

For the purpose of the present disclosure, the term "rancidity" refers to the process of complete or incomplete oxidation or hydrolysis of fats and oils when exposed to air, light, or moisture or by bacterial action, resulting in unpleasant taste and/or odour.

For the purposes of the present document, the term "reduced lipase" or "reduced TAG lipase activity" refers to the reduced activity of lipase enzyme activity that is determinant of rancidity in millet having a mutant gene encoding a PgTAG Lipase whose activity is lower (e.g., statistically significantly lower) than that of the corresponding wild type PgTAG Lipase gene.

The term "reduced rancidity" refers to the rancidity of a millet having a mutant gene encoding a PgTAG Lipase whose rancidity is statistically significantly lower than a wild type gene encoding PgTAG Lipases.

In the present disclosure, the wild type PgTAG Lipase genes are represented by a nomenclature: "PgTAGLip1" and "PgTAGLip2" genes which have the nucleotide sequence as set forth in SEQ ID NO: 1, and SEQ ID NO: 3, respectively. "PgTAGLip1" and "PgTAGLipase 1" are used interchangeably, and "PgTAGLip2" and "PgTAGLipase 2" are used interchangeably throughout the present disclosure.

The proteins encoded by "PgTAGLip1 gene" (SEQ ID NO: 1), and "PgTAGLip2 gene" (SEQ ID NO: 3) are represented by a nomenclature "PgTAGLIP1", and "PgTAGLIP2", respectively. The amino acid sequence of PgTAGLIP1 and PgTAGLIP2, is as set forth in SEQ ID NO: 2, and SEQ ID NO: 4, respectively.

As used herein, the term "hydrolytic stability" refers to the conversion of tri-acylglycerides (TAG) into non-esterified or free fatty acids (FFA). An increase or improvement in hydrolytic stability refers to a reduction in the rate of TAG conversion to FFA.

The term, "increased shelf life" refers to an increase in the time period for which the product can remain sellable, usable, or consumable. In some embodiments, an "increased shelf life" may also refer to the reduced accumulation of free fatty acids, hexanal, or objectionable flavours and odours.

As used herein, lipase is an enzyme that catalyzes the hydrolysis of fats (lipids): Lipases are a subclass of esterases. In the present disclosure, TAG lipases are enzymes that cause lipolysis and oxidation of de-esterified unsaturated fatty acids. The lipolysis and oxidation of de-esterified unsaturated fatty acids is caused by the following: (a) oxidative/hydrolytic enzymatic action; (b) physical process: The physical process involves oxidation of the unsaturated double bonds on exposure to air. This physical process is accelerated: (i) under elevated temperatures, by light; and/or (ii) in presence of transition metals particularly Iron and Copper.

As used herein, an "increased oxidative stability" refers to a reduction in the rate of degradation of a product by available oxygen.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers, and to longer chains generally referred to as proteins. Polypeptides may contain amino acids other than the 20 gene-encoded standard amino acids. "Polypeptide(s)" include those modified either by natural processes, such as processing and other post-translational modifications, but also by chemical modification techniques. Such modifications are well described in scientific literature and are well known to those of skill in the art. It will be appreciated that the same type of modification may be present in the same or varying degree at several sites in a given polypeptide.

The term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, cDNA, single- and double-stranded RNA, and RNA that is a mixture of single- and double-stranded regions, hybrid molecules comprising DNA and RNA that may be single-stranded or, more typically, double-stranded, or triple-stranded regions, or a mixture of single- and double-stranded regions. The term "polynucleotide(s)" also embraces short nucleotides or fragments, often referred to as "oligonucleotides".

The term "recombinant" refers to an artificial combination of two otherwise separated segments of sequence, e.g., by chemical synthesis, or manipulation of isolated segments of nucleic acids by genetic engineering techniques.

The term "recombinant construct" comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. In the present disclosure, "recombinant construct", "recombinant DNA molecule", "expression construct", "construct", and "recombinant DNA construct" are used interchangeably herein.

As used herein, the term "transgenic plant" refers to a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

The term "gene edited plant" refers to a plant comprising at least one cell comprising at least one gene edited by human intervention. Such gene edits include deletion, insertion, silencing, or repression, such as of the "native genome" of the cell. Methods for creating a gene edited plant include, but are not limited to techniques such as zinc-finger nucleases (ZFN), transcription activator-like effector nucleases (TALEN), and clustered regularly interspersed short palindromic repeats (CRISPR/Cas) system. For example, targeted editing in the genome of a plant can be made by introducing a double strand break (DSB) or nick. According to this approach, mutations, such as deletions, insertions, inversions and/or substitutions may be introduced at a target site via imperfect repair of the DSB or nick to produce a knock-out or knock-down of an endogenous gene (i.e., a gene encoding pgTAG lipase). Such mutations may be generated by imperfect repair of the targeted locus even without the use of a donor template molecule. The DSB may be repaired via a Non-Homologous End Joining (NHEJ) pathway in the absence of any additional composition, via template-directed repair in the presence of a polynucleotide modification template, or via homologous recombination with a heterologous polynucleotide (donor DNA molecule). The HDR pathway repairs double-stranded DNA breaks and includes homologous recombination (HR) and single-strand annealing (SSA) (Lieber 2010. Annual Review Biochemistry 79:181-211).

The term "target polynucleotide", refer to a polynucleotide sequence such as, but not limited to, a nucleotide sequence on a chromosome, episome, or any other DNA molecule in the genome (including chromosomal, chloroplast, mitochondrial DNA, plasmid DNA) of a cell that can be gene edited. Target polynucleotide includes one which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. Cells include, but not limited to plant cells as well as plants and seeds produced by the methods described herein. The terms "target polynucleotide" target site", "target sequence", "target site sequence, "target DNA", "target polynucleotide" are used interchangeably herein.

As used herein, the term "guide polynucleotide/Cas complex" refers to at least one guide polynucleotide (e.g., guide RNA) and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occur if the correct protospacer-adjacent motif (PAM) is located at or adjacent to the 3' end of the DNA target sequence. Alternatively, a Cas protein herein may lack DNA cleavage or nicking activity but can still specifically bind to a DNA target sequence when complexed with a suitable RNA component.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All patent applications, patents, and printed publications cited herein are incorporated herein by reference in the entireties, except for any definitions, subject matter disclaimers or disavowals and except to the extent that the incorporated material is inconsistent with the express disclosure herein, in which case the language in this disclosure controls.

The present disclosure is not to be limited in scope by the specific embodiments described herein, which are intended for the purposes of exemplification only. Functionally-equivalent products, compositions, and methods are clearly within the scope of the disclosure, as described herein.

There are various mechanical and physiochemical techniques, such as, dehulling, blanching, heat treatment by dry heating, microwave heating and infra-red heating, High-density polyethylene (HDPE), packaging and refrigeration, that reduces the rancidity and increases shelf life of the millet flour. However, these techniques have limitations on maintaining the total quality of micronutrients and macronutrients. These techniques consequently reduce the total iron/zinc or other micronutrient content of millet grains and their food products. Hence, all these traditional and physical techniques show limited success in reducing rancidity and increasing shelf life of the milled flour. Further, various efforts have been made to correlate quantitatively rancidity determinants with volatile and semi-volatile compounds produced during storage of flour, to understand the variability in terms of biochemical behavior. However, key genetic factors to improve the shelf life and reduce rancidity of pearl millet flour have not been disclosed. This has hampered the ability of the crop breeders to identify and develop millet genotypes that provide enhanced shelf life. Thus, there is a desire for genetic solutions to reduce rancidity and to improve shelf life and of millet (e.g., pearl millet). There is also a desire to reduce the rancidity of millet (e.g., pearl millet) meal or flour with minimal or no alteration of its nutritional and other phenotypic parameters.

The present disclosure addresses these problems by identifying mutant genes in millet associated with reduced lipase activity. The disclosed mutant genes are also associated with enhanced shelf life or reduced rancidity in pearl millet and can be used to identify and develop low rancid mutant pearl millet plant lines and products thereof. The present disclosure relates to an isolated polynucleotide encoding for a polypeptide having an amino acid sequence as set forth in SEQ ID NO: 2 (PgTAGLIP1) and SEQ ID NO: 4 (PgTAGLIP2), wherein said polypeptide comprises one or more mutations.

The present disclosure also relates to plants comprising one or more mutations in genes encoding the polypeptide SEQ ID NO: 2 or SEQ ID NO: 4, which mutant genes can be screened for or generated by any suitable method in the art, for example, genome editing, single locus conversion or gene replacement. The mutations in SEQ ID NO: 2, or SEQ ID NO: 4 may be introduced using any genome modification technique known in the art or described herein. In certain embodiments, the mutations are introduced through a genome modification technique selected from the group consisting of a polynucleotide-guided endonuclease, CRISPR-Cas endonucleases, base editing deaminases, zinc finger nuclease, a transcription activator-like effector nuclease (TALEN).

For example, the disclosure provides mutations proximal to the catalytic active site of polypeptide (SEQ ID NO: 2) that results in a mutant polypeptide SEQ ID NO: 7. In another example, the disclosure provides mutations proximal to the catalytic active site of polypeptide (SEQ ID NO: 4) that results in a mutant polypeptide having an amino acid sequence SEQ ID NO: 9 or SEQ ID NO: 11.

Millet, e.g., pearl millet plants comprising the mutant polypeptide described herein can have lower lipase activity, lower rancidity, and better keeping quality. For this purpose, the present disclosure also discloses a gene edited or transgenic plant having reduced lipase activity, and method for obtaining the transgenic plant with reduced lipase activity. The gene edited or transgenic plant exhibits the following characteristic features: (a) increased shelf life; (b) reduced free fatty acid production; (c) reduced hexanal production; (d) increased oxidative stability; (e) increased hydrolytic stability; (f) reduced volatiles production; and (g) improved sensory characteristics (e.g., reduced rancidity). Moreover, the food products produced from the transgenic plant or gene-edited plants are also disclosed in the present disclosure.

Millet e.g., pearl millet plants comprising mutant genes encoding for reduced TAG Lipase activity provide new opportunities to develop food products with reduced rancidity, reduced lipase activity, enhanced shelf life, and flavor. The development of said food product comprising millet having reduced rancidity would change the way this millet (a nutricereal) is viewed by the processing industry and fill an unmet need in the gluten free flour category that does not currently exist largely due to issues of rancidity. Millet, e.g., pearl millet plants comprising the disclosed mutant genes also provide millet breeders and biotechnologists with the tools to develop elite germplasm with enhanced processing quality. The method provided herein for increasing the shelf life of millet (e.g., pearl millet) crops also creates opportunities for primary and secondary processing markets and can enhanced the value or profits extracted from these crops by smallholder farmers.

In an implementation of the present disclosure, there is provided a food product comprising millet, e.g., pearl millet, having reduced rancidity, wherein the millet comprises a mutant gene encoding a PgTAG Lipase with reduced TAG Lipase activity.

In an implementation of the present disclosure, there is provided a food product comprising millet, e.g., pearl millet, having reduced rancidity, wherein the millet comprises a polynucleotide that encodes a polypeptide having a substitution at an amino acid position in SEQ ID NO: 2, wherein the substitution at the amino acid position is selected from the group consisting of positions at 12, 18, 19, 20, 23, 26, 37, 38, 42, 43, 44, 96, 97, 98, 114, 131, 135, 144, 145, 146, 167, 168, 169, 172, 205, 206, 215, 221, 222, 237, 246, 263, 289, 290, 298, 299, 330, 339, and 346.

In an implementation of the present disclosure, there is provided a food product comprising millet, e.g., pearl millet, having reduced rancidity, wherein the millet comprises a polynucleotide that encodes a polypeptide having a substitution at an amino acid position at an amino acid sequence as set forth in SEQ ID NO: 4, wherein the substitution at the amino acid position is selected from the group consisting of positions at 220, 223, 265, 316, 317, 318, 319, 320, 321, 322, 323, 324, 325, 326, 327, 328, 329, 330, 331, and 332.

In an implementation of the present disclosure, there is provided a food product comprising millet, e.g., pearl millet, having reduced rancidity, wherein the millet comprises a polynucleotide that encodes a polypeptide having an amino acid sequence as set forth in SEQ ID NO: 7.

In an implementation of the present disclosure, there is provided a food product comprising millet, e.g., pearl millet, having reduced rancidity, wherein the millet comprises a polynucleotide that encodes a polypeptide having an amino acid sequence as set forth in SEQ ID NO: 13; SEQ ID NO: 15, SEQ ID NO: 17, SEQ ID NO: 19, SEQ ID NO: 21, and SEQ ID NO: 25.

In an implementation of the present disclosure, there is provided a food product comprising millet, e.g., pearl millet, having reduced rancidity, wherein the millet comprises a polynucleotide having a nucleotide sequence as set forth in SEQ ID NO: 22.

In an implementation of the present disclosure, there is provided a food product comprising millet, e.g., pearl millet, wherein the millet comprises a polynucleotide that encodes a polypeptide having an amino acid sequence as set forth in SEQ ID NO: 9, and SEQ ID NO: 11.

In an implementation of the present disclosure, there is provided a food product comprising millet, e.g., pearl millet, wherein the millet comprises a polynucleotide having a nucleotide sequence selected from the group having the sequence as set forth in SEQ ID NO: 26, SEQ ID NO: 28, and SEQ ID NO:30.

In an implementation of the present disclosure, there is provided a food product comprising millet, e.g., pearl millet, wherein the millet comprises a polynucleotide that encodes (i) a sense strand of at least 20 contiguous nucleotides of a polynucleotide encoding a polypeptide having an amino acid sequence as set forth in SEQ ID NO: 2 or SEQ ID NO: 4, (ii) a spacer polynucleotide; and (iii) an antisense strand that is complementary to the sense strand.

In an implementation of the present disclosure, there is provided an isolated polynucleotide encoding a polypeptide, wherein the polynucleotide encodes a polypeptide having a substitution at an amino acid position in SEQ ID NO: 2, wherein the substitution at the amino acid position is selected from the group consisting of positions at 12, 18, 19, 20, 23, 26, 37, 38, 42, 43, 44, 96, 97, 98, 114, 131, 135, 144, 145, 146, 167, 168, 169, 172, 205, 206, 215, 221, 222, 237, 246, 263, 289, 290, 298, 299, 330, 339, and 346.

In an implementation of the present disclosure, there is provided a food product comprising millet, e.g., pearl millet, having reduced rancidity as described herein, wherein the reduced rancidity refers to the rancidity of a millet having a modified or mutant gene encoding a PgTAG Lipase (e.g., modified or mutant SEQ ID NO: 2 or SEQ ID NO: 4) that is statistically significantly lower than that of the rancidity of a wild type gene encoding PgTAG Lipases.

In yet another implementation of the present disclosure, the food product rancidity provided by millet having a mutant gene encoding a PgTAG Lipase can be 0-10%, or 10-30%, or 30-50%, or 50-70%, or 70-80%, or 80-90%, or 90-99%, lower than the rancidity provided by a millet having wild type gene encoding PgTAG Lipases.

In an embodiment of the present disclosure, the food product rancidity provided by a millet having a mutant gene encoding a PgTAG Lipase can be 0-1%, 1%, 2%, 3%, 4, 5%, 6%, 7%, 8%, 9%, 10%, 11%, 12%, 13%, 14%, 15%, 16%, 17%, 18%, 19, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, 99% lower than the food product rancidity provided by a millet having wild type gene encoding PgTAG Lipases, after storage of the food products for the same period of time under the same conditions. In another embodiment of the present disclosure, the food product made from millet having a mutant gene as described herein has no rancidity or zero rancidity as compared to food product from millet having wild type gene encoding PgTAG Lipases, after both are stored for the same period of time under the same conditions.

In an embodiment of the present disclosure, the reduced TAG lipase activity of a disclosed mutant PgTAGLIP1 or mutant PgTAGLIP2 refers to lipase enzyme activity that is reduced by 1-10%, or 10-30%, or 30-50%, or 50-70%, or 70-80%, or 80-90%, or 90-99%, relative to that of the activity of the wild type PgTAG Lipase (PgTAGLIP1 or PgTAGLIP2/SEQ ID NO: 4, respectively). Exemplary mutant PgTAGLIP1 and PgTAGLIP2 include any mutation in SEQ ID NO: 2 that reduces lipase activity.

In an embodiment of the present disclosure, the reduced TAG Lipase activity of a disclosed mutant PgTAGLIP1 or mutant PgTAGLIP2 refers to lipase activity that is reduced by 0.1-1%, 1%, 2%, 3%, 4, 5%, 6%, 7%, 8%, 9%, 10%, 11%, 12%, 13%, 14%, 15%, 16%, 17%, 18%, 19, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, 99% relative to the activity level of the wild type PgTAG Lipase (PgTAGLIP1 or PgTAGLIP2, respectively). In another embodiment of the present disclosure, the mutant gene as described herein has no activity or zero activity as compared to wild type gene encoding PgTAG Lipases. Methods for assaying lipase activity are known in the art and discussed herein.

In an example of the present disclosure, there is provided a food product comprising millet having reduced rancidity as described herein, wherein the millet, e.g., pearl millet comprises mutant gene SEQ ID NO: 5 or SEQ ID NO: 6. In yet another example of the present disclosure, there is provided a food product comprising millet having reduced rancidity as described herein, wherein the millet, e.g., pearl millet comprises mutant gene SEQ ID NO: 8 or SEQ ID NO: 10.

In an implementation of the present disclosure, there is provided an isolated polynucleotide encoding a polypeptide, wherein the polynucleotide encodes a polypeptide having one or more substitutions at an amino acid sequence as set forth in SEQ ID NO: 4, the substitutions are at one or more of amino acid positions selected from the group consisting of positions 220, 223, 265, 316, 317, 318, 319, 320, 321, 322, 323, 324, 325, 326, 327, 328, 329, 330, 331, and 332 of SEQ ID NO: 4.

As per one of the implementation of the present disclosure, the substituted amino acid position in SEQ ID NO: 2 is selected from the group consisting of positions 12, 18, 19, 20, 23, 26, 37, 38, 42, 43, 44, 96, 97, 98, 114, 131, 135, 144, 145, 146, 167, 168, 169, 172, 205, 206, 215, 221, 222, 237, 246, 263, 289, 290, 298, 299, 330, 339, and 346, wherein the substitution corresponds to A12T, L18A, L19R, S20S, P23L, G26S, S37L, S38F, T42F, E43*, S44*, C96W, F97V, E98*, V114*, K131I, I135*, V144W, G145C, V146*, N167T, W168G, W168G, L172*, A205P, I206*, I206S, K215S, D221T, I222*, C237Y, G246*, A263P, L289C, P290L, Q298S, L299*, N330I, F339S, L346*, respectively. In an exemplary embodiment, the substitution in SEQ ID NO: 2 is A12T, resulting in a change from alanine to threonine at an amino acid position 12 in SEQ ID NO: 2. In another exemplary embodiment, the substitution in SEQ ID NO: 2 is I222*, resulting in a change from isoleucine to a stop (*) codon at an amino acid position 222 of SEQ ID NO: 2.

As per one of the implementation of the present disclosure, the substituted amino acid position in SEQ ID NO: 4 is selected from the group consisting of positions 220, 223, 265, 316, 317, 318, 319, 320, 321, 322, 323, 324, 325, 326, 327, 328, 329, 330, 331, and 332, wherein the substitution corresponds to A220V, A223V, W265*, R316G, G317I, S318L, C319S, Q320I, F321C, V322N, M323G, G324F, S325R, A326Q, N327L, S328S, V329I, Y330Q, S331L, Y332H, respectively.

In an implementation of the present disclosure, there is provided an isolated polynucleotide encoding a polypeptide having amino acid sequence SEQ ID NO: 7.

In an implementation of the present disclosure, there is provided an isolated polynucleotide encoding a polypeptide having amino acid sequence as set forth in SEQ ID NO: 13, SEQ ID NO: 15, SEQ ID NO: 17, SEQ ID NO: 19, SEQ ID NO: 21, or SEQ ID NO: 25.

In an implementation of the present disclosure, there is provided an isolated polynucleotide that has a nucleotide sequence as set forth in SEQ ID NO: 22.

In an implementation of the present disclosure, there is provided an isolated polynucleotide encoding a polypeptide having an amino acid sequence as set forth in SEQ ID NO: 9, and SEQ ID NO: 11.

In an implementation of the present disclosure, there is provided an isolated polynucleotide encoding a polypeptide having the sequence as set forth in SEQ ID NO: 26, SEQ ID NO: 28, and SEQ ID NO:30.

In a further implementation of the present disclosure, there is provided a recombinant construct comprising a heterologous promoter operably linked to the isolated polynucleotide described herein as an implementation of the present disclosure.

Various methods can be used to introduce the polynucleotide encoding a disclosed mutant polypeptide with reduced TAG lipase activity described herein or recombinant DNA comprising such a polynucleotide as described herein into a plant, plant part, plant cell, seed, and/or grain. "Introducing" is intended to mean altering the plant, plant cell, seed, and/or grain to include (e.g., by mutagenesis, by editing its genome or by presenting) the inventive polynucleotide sequence disclosed herein. The methods of the disclosure do not depend on a particular method for introducing a sequence into a plant, plant cell, seed, and/or grain.

Stable transformation is intended to mean that the polynucleotide introduced into a plant integrates into the genome of the plant of interest and is capable of being inherited by the progeny thereof. "Transient transformation" is intended to mean that a polynucleotide is introduced into the plant of interest and does not integrate into the genome of the plant or organism or a polypeptide is introduced into a plant or organism.

Transformation protocols as well as protocols for introducing polypeptides or polynucleotide sequences into plants may vary depending on the type of plant or plant cell, targeted for transformation. Suitable methods of introducing polypeptides and polynucleotides into plant cells include, but not limited to *Agrobacterium*-mediated transformation, particle bombardment-based method, and in-planta transformation.

Methods are known in the art for the targeted insertion of a polynucleotide at a specific location in the plant genome. In one embodiment, the insertion of the polynucleotide at a desired genomic location is achieved using a site-specific recombination system. Briefly, the polynucleotide disclosed herein can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided, and the transfer cassette is integrated at the target site. The polynucleotide of interest is thereby integrated at a specific chromosomal position in the plant genome.

A person skilled in the art will recognize that after the expression cassette containing the isolated polynucleotide as described herein, is stably incorporated in transgenic plants and confirmed to be operable, it can be introduced into other plants by sexual crossing. Any of a number of standard breeding techniques can be used, depending upon the species to be crossed.

Parts obtained from the regenerated plants described herein, such as flowers, seeds, leaves, branches, fruit, and the like are included, provided that these parts comprise cells comprising the isolated polynucleotide as described herein. Progeny and variants, and mutants of the regenerated plants are also included, provided that these parts comprise the introduced nucleic acid sequences.

In the present disclosure, various methods can be used to introduce a genetic modification (i.e., mutation) at a genomic locus (SEQ ID NO: 1, or SEQ ID NO: 3) that encodes a polypeptide (SEQ ID NO: 2, or SEQ ID NO: 4, respectively) into the plant, plant part, plant cell, seed, and/or grain. In an embodiment of the present disclosure, the targeted DNA modification is through a genome modification technique selected from the group consisting of a polynucleotide-guided endonuclease, CRISPR-Cas endonucleases, Targeting Induced Local Lesions IN Genomes (TILLING), base editing deaminases, zinc finger nuclease, a transcription activator-like effector nuclease (TALEN), engineered site-specific meganuclease, or Argonaute. In an exemplary embodiment of the present disclosure, the targeted DNA modification is through a genome modification technique CRISPR-Cas endonuclease. In another exemplary embodiment of the present disclosure, the targeted DNA modification is through TALEN. In yet another exemplary embodiment of the present disclosure, the targeted DNA modification is through TILLING.

(a) Zinc-Finger Nucleases (ZFNs)

Zinc-finger nucleases (ZFNs) are artificial restriction enzymes generated by fusing a zinc finger DNA-binding domain to a DNA-cleavage domain. ZFNs were created by combining zinc finger protein (ZFP) to the cleavage domain of the FokI enzyme. These can be redesigned to cleave new targets by developing ZFPs that can cleave any specific target sequence. Engineering of ZFN and the FokI render it possible to recognize the target of interest, bind and cleave that very specific region, and allow a broad range of genetic manipulations at predefined locations. ZFNs can induce DSBs in specific DNA sequences and promote site-specific homologous recombination with an exogenous template. The exogenous template contains the sequence that is to be introduced into the genome.

(b) TALENS

TALENs (transcription activator-like effector nucleases) are an alternative for ZFNs and work as pairs. The bindings sites for TALENs are chosen so that they get settled on opposite DNA strands and are separated by a spacer sequence. DNA binding domain fused with carboxy-terminal FokI cleavage domain dimerizing the TALEN proteins, which cut two ends of 12-19 bp spacer sequence. The TALE binding domains have repeating sequences with 34 residues which was a breakthrough finding to create a sequence-specific nuclease (SSN) binding site. Such engineered fused TALE protein with nuclease, better known as TALEN, can bring modification in nearly any type of gene. The sole limitation to the choice of TALEN enzyme sites is the need for T before the 5'-finish of the target sequence. However, this limitation may be overcome by selectively choosing mutant variants of the TALEN N-terminal domain that are capable of binding to A, G, or C. Nonetheless, this technology does come with its shares of challenges, such as the large nature of repeat structures in TAL effector proteins, difficulty in assembling, delivery into plant cells and associated instabilities.

(c) CRISPR/Cas System

Clustered regularly interspaced short palindromic repeats (CRISPR) tool gained more popularity than ZFNs and TALENs due to reduced off-target binding and simplicity in its utilization. The CRISPR (clustered regularly interspaced short palindromic repeats) locus, which encodes RNA components of the system, and the cas (CRISPR-associated) locus, which encodes proteins (Jansen et al. (2002) Mal. Microbial. 43:1565-1575; Makarova et al. (2002) Nucleic Acids Res. 30:482-496; Makarova et al. (2006) Biol. Direct 1:7; Haft et al. (2005) PLOS Comput. Biol. 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H—N—H) nuclease domain, each of which can cleave a single DNA strand at a target sequence (the concerted action of both domains leads to DNA double strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al. (2014) Cell 157:12621278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

For RNA-guided endonucleases, a guide RNA (gRNA) molecule is further provided to direct the endonuclease to a target site in the genome of the plant via base-pairing or hybridization to cause a DSB or nick at or near the target site. The gRNA may be transformed or introduced into a plant cell or tissue (perhaps along with a nuclease, or nuclease-encoding DNA molecule, construct or vector) as a gRNA molecule, or as a recombinant DNA molecule, construct or vector comprising a transcribable DNA sequence encoding the guide RNA operably linked to a plant-expressible promoter. As understood in the art, a "guide RNA" may comprise, for example, a CRISPR RNA (crRNA), a single-chain guide RNA (sgRNA), or any other RNA molecule that may guide or direct an endonuclease to a specific target site in the genome. A "single-chain guide RNA" (or "sgRNA") is a RNA molecule comprising a crRNA covalently linked a tracrRNA by a linker sequence, which may be expressed as a single RNA transcript or molecule. The guide RNA comprises a guide or targeting sequence that is identical or complementary to a target site within the plant genome, such as at or near a PgTAG Lipase coding sequence. A protospacer-adjacent motif (PAM) may be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. See, e.g., Wu, X. et al. (2014) "Target specificity of the CRISPR-Cas9 system," Quant Biol. 2(2): 59-70. The guide RNA may typically be a non-coding RNA molecule that does not encode a protein. The guide sequence of the guide RNA may be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 18, 19, 20, 21, 22, 23, 24, 25 or more nucleotides in length. The guide sequence may be at least 95%, at least 96%, at least 97%, at least 99% or 100% identical or complementary to at least 10, at least 11, at least 12, at least 13, at least 14, at least 15, at least 16, at least 17, at least at least 19, at least 20, at least 21, at least 22, at least 23, at least 24, at least 25, or more consecutive nucleotides of a DNA sequence at the genomic target site.

Genome editing using double stranded break DSB-inducing agents, such as Cas endonuclease-gRNA complexes, has been described, for example in U.S. Patent Application US 2015-0082478 A1, published on Mar. 19, 2015, WO2015/026886 A1, published on Feb. 26, 2015, W02016007347, published on Jan. 14, 2016, and WO201625131, published on Feb. 18, 2016. The DSB can be repaired by using non-homologous end-joining (NHEJ) or homology-directed recombination (HDR) pathways. The NHEJ repair pathway often results in insertions/deletions (InDels) at the DSB site that can lead to frameshifts and/or premature stop codons, effectively disrupting the function of the targeted gene. HDR can be used to introduce exogenous DNA at the repairing site of the cleaved DNA. These mechanisms enable a Cas endonuclease-gRNA complex to introduce targeted mutations and create gene edited plants as disclosed herein.

Vectors comprising polynucleotides encoding a Cas endonuclease, and optionally one or more, or two or more gRNAs are provided to a plant cell by transformation methods known in the art (e.g., without being limiting, particle bombardment, PEG-mediated protoplast transfection or *Agrobacterium*-mediated transformation). Methods for the introduction of Cas endonucleases and guide polynucleotide into plant cells are described, for example, in US 2016/0208272 A1, published 21 Jul. 2016, and in US 2016/0201072 A1, published 14 Jul. 2016. In the case of a CRISPR-Cas system, uptake of the endonuclease and/or the guided polynucleotide into the cell can be facilitated with a Cell Penetrating Peptide (CPP) as described in WO2016073433 published May 12, 2016. Alternatively, CRISPR-Cas system components can be delivered by transfection, such as by lipofection, electroporation, nucleofection, microinjection, viral particle encapsulation, etc.

(d) Double Stranded RNA Suppression

In an implementation of the present disclosure, there is provided a dsRNA recombinant construct encoding a Double Stranded RNA Suppression or "dsRNA". As used herein, "dsRNA" is meant to encompass polynucleotides capable of mediating RNA interference or gene silencing, including, for example, short-interfering RNA (siRNA), double-stranded RNA (dsRNA), micro-RNA (miRNA), hairpin RNA, short hairpin RNA (shRNA), post-transcriptional gene silencing RNA (ptgsRNA), and others. The dsRNA recombinant construct comprises a heterologous promoter operably linked to sequence encoding: (a) a sense strand of at least 20 contiguous nucleotides of a polynucleotide encoding a polypeptide having an amino acid sequence as set forth in SEQ ID NO: 2 or SEQ ID NO: 4; (b) a spacer polynucleotide; and (c) an antisense strand that is complementary to the sense strand of a). SEQ ID NO:1 is an example of a polynucleotide encoding SEQ ID NO: 2 and SEQ ID NO: 3 is an example for a polynucleotide encoding SEQ ID NO: 4. In one example, of such a recombinant construct the sense strand of (a) comprises at least 20, at least 30, at least 40, at least 50, at least 60, at least 70, or at least 80 contiguous nucleotides of a polynucleotide encoding a polypeptide having an amino acid sequence as set forth in SEQ ID NO: 2 or SEQ ID NO: 4. In another example, the sense strand of (a) comprises 20-30, 40-50, 50-60, 60-70, 70-80, or 80-90 contiguous nucleotides of a polynucleotide encoding a polypeptide having an amino acid sequence as set forth in SEQ ID NO: 2 or SEQ ID NO: 4.

In an implementation of the present disclosure, there is provided a dsRNA recombinant construct comprising a heterologous promoter operably linked to sequence encoding: (a) a sense strand having a nucleotide sequence as set forth in SEQ ID NO: 68, or SEQ ID NO: 70; (b) a spacer polynucleotide; and (c) an antisense strand that is complementary to the sense strand of a). For example, the (c) antisense strand that is complementary to the sense strand of a) can have a nucleotide sequence as set forth in SEQ ID NO: 69 or SEQ ID NO: 71.

In an implementation of the present disclosure, there is provided a recombinant construct comprising a heterologous promoter operably linked to sequence encoding: (a) a sense strand having a nucleotide sequence as set forth in SEQ ID NO: 70; (b) a spacer polynucleotide selected from the group consisting of polynucleotide having the nucleotide sequence as set forth in SEQ ID NO: 66, and SEQ ID NO: 67; and (c) an antisense strand that is complementary to the sense strand of a), has a nucleotide sequence as set forth in SEQ ID NO: 71.

In an implementation of the present disclosure, there is provided a recombinant vector comprising the recombinant construct as described herein.

In an implementation of the present disclosure, there is provided a recombinant vector comprising the recombinant construct as described herein, wherein the recombinant vector is a plant expression vector.

In an implementation of the present disclosure, there is provided a recombinant host cell comprising the recombinant construct as described herein or the recombinant vector as described herein.

In an implementation of the present disclosure, there is provided a recombinant host cell as described herein, wherein the host cell is selected from the group consisting of bacteria, yeast and plant. In another implementation of the present disclosure, the host cell is bacteria. In yet another implementation of the present disclosure, the host cell is yeast. In one another implementation of the present disclosure, the host cell is plant.

In an implementation of the present disclosure, the heterologous promoter for use in a recombinant construct provided herein is a promoter selected from the group consisting of consisting of constitutive promoters selected from ubiquitin, or enhanced CAMV35S, AXIG1, and U6. In certain examples it can be preferable to use seed-preferred promoters that preferentially express gene products in seed tissues. The term "seed-preferred promoter" when used herein can be a FAD2-1, Glutenin, zein, or BD1 promoter or any of the following seed-preferred promoters: Maize Cystatin (CC7) promoter, Maize Lipid transfer Protein promoter, Aleurone specific promoter, Embryo Abundant Protein promoter, Maize Globulin 1 promoter, Jasomonate Induced Protein promoter, Barley Lipid Transfer Protein promoter, Maize 16KD Oleosin promoter, *Sorghum* 16KD Oleosin promoter, Maize 17KD Oleosin promoter, Maize 18KD Oleosin promoter, Maize Embryo Abundant Protein2 promoter, Maize Globulin Like Protein promoter, Maize Leafy Cotyledon 1 promoter, Maize Vacuolar Processing Enzyme promoter, Maize 22KD Alpha Zein promoter, Barley Endosperm Pyrophosphorylase (Small Subunit) promoter, Cytokinin Induced Message from maize promoter, Maize 19KD Alpha Zein promoter, Early Endosperm Protein from Maize promoter, Early Endosperm Protein from Maize promoter, Maize Floury 2 (22KD Zein) promoter, 27 KD Gamma Zein from Maize (W64A) promoter, *Sorghum* Alpha Kafirin promoter, *Sorghum* Beta Kafirin promoter, *Sorghum* Delta Kafirin promoter, *Sorghum* Legumin promoter, Waxy gene from Maize promoter, Maize Legumin promoter, Putative Proteinase Inhibitor promoter, or Subtilison Inhibitor Protein promoter. (See, e.g., Belanger and Kriz (1989). Molecular Characterization of the Major Maize Embryo Globulin Encoded by the Glb1 Gene. *Plant Physiology* 91(2):636-643; Kalla et al. (1994)). The promoter of the barley aleurone-specific gene encoding a putative 7 kDa lipid transfer protein confers aleurone cell-specific expression in transgenic rice. *Plant J.* 6(6):849-860; Lee et al. (1991); Maize oleosin is correctly targeted to seed oil bodies in *Brassica napus* transformed with the maize oleosin gene. *Proc. Nat'l Acad. Sci. USA* 88(4) 6181-6185; Joshi et al., (2015). A maize α-zein promoter drives an endosperm-specific expression of transgene in rice. *Physiology Molecular Biology Plants* 21(1):35-42; Russell and Fromm (1997). Tissue-specific expression in transgenic maize of four endosperm promoters from maize and rice. *Transgenic Research* 6(2):157-168.

In an implementation of the present disclosure, there is provided a transgenic or gene-edited plant, plant tissue, or cell thereof having reduced lipase activity comprising a polynucleotide that encodes Mut-PgTAGLip1 or Mut-PgTAGLip2 disclosed herein. In an implementation of the present disclosure, there is provided a transgenic or gene-edited plant, plant tissue, or cell thereof having reduced lipase activity comprising a polynucleotide that encodes a polypeptide having an amino acid position as set forth in SEQ ID NO: 7, SEQ ID NO: 13; SEQ ID NO: 15, SEQ ID NO: 17, SEQ ID NO: 19, SEQ ID NO: 21, or SEQ ID NO: 25.

In an implementation of the present disclosure, there is provided a plant, e.g., a transgenic or gene-edited plant, plant tissue, or cell thereof having reduced lipase activity comprising a polynucleotide that has a nucleotide sequence as set forth in SEQ ID NO: 22, SEQ ID NO: 9, or SEQ ID NO: 11.

In an implementation of the present disclosure, there is provided a plant, e.g., a transgenic or gene-edited plant, plant tissue, or cell thereof having reduced lipase activity comprising a polynucleotide that has a nucleotide sequence selected from the group having the sequence as set forth in SEQ ID NO: 26, SEQ ID NO: 28, and SEQ ID NO:30.

In an implementation of the present disclosure, there is provided a plant, plant tissue, or cell thereof comprising a dsRNA recombinant construct disclosed herein. The dsRNA recombinant construct can comprise a polynucleotide that encodes (i) a sense strand of at least 20 contiguous nucleotides of a polynucleotide encoding a polypeptide having an amino acid sequence as set forth in SEQ ID NO: 2 or SEQ ID NO: 4, (ii) a spacer polynucleotide; and (iii) an antisense strand that is complementary to the sense strand. For example, the (i) sense strand can comprise at least 20-30, 40-50, 50-60, 60-70, 70-80, or 80-90 contiguous nucleotides of a polynucleotide encoding a polypeptide having an amino acid sequence as set forth in SEQ ID NO: 2 or SEQ ID NO: 4. Exemplary polynucleotides sense strand encoding a polypeptide having an amino acid sequence as set forth in SEQ ID NO: 2 or SEQ ID NO: 4 include SEQ ID NO: 68 or SEQ ID NO: 70, respectively; and an antisense strand that is complementary to the sense strand have a polynucleotide as set forth in SEQ ID NO: 69, or SEQ ID NO: 71, respectively.

In an implementation of the present disclosure, there is provided a transgenic plant having reduced lipase activity comprising the recombinant construct as described herein.

In an implementation of the present disclosure, the plant, gene edited plant, or transgenic plant having reduced lipase activity provided herein exhibits one or more characteristics selected from the group consisting of: (a) reduced free fatty acid production; (b) reduced hexanal production; (c) increased oxidative stability; (d) increased hydrolytic stability; (e) reduced volatiles production; and (f) improved sensory characteristics (e.g., reduced rancidity). Each of these characteristics is relative to a plant that has wild type PgTAG activity and is otherwise isogenic to the plant having reduced lipase activity.

In each implementation of the present disclosure relating to a plant, gene edited plant, or transgenic plant having reduced lipase activity as described herein, the plant can be a millet, e.g., a Pearl millet, Finger millet, Foxtail millet, Small millet, or Kodo millet. In an exemplary embodiment of the present disclosure, the plant, gene edited plant, or transgenic plant having reduced lipase activity as described herein is a pearl millet.

The reduced lipase activity of the plant, gene edited plant, or transgenic plant having reduced lipase activity as described herein is a lipase activity reduced to 0-10%, or 10-30%, or 30-50%, or 50-70%, or 70-80%, or 80-90%, or 90-99%, of the activity level of the wild type, the otherwise isogenic plant having wild type PgTAG activity. In another implementation of the present disclosure, the lipase activity of the transgenic plant is reduced to 0-1%, 1%, 2%, 3%, 4, 5%, 6%, 7%, 8%, 9%, 10%, 11%, 12%, 13%, 14%, 15%, 16%, 17%, 18%, 19, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, 99% more than the activity level of the wild type, the otherwise isogenic plant having wild type PgTAG activity. In yet another implementation of the present disclosure, the lipase activity of the plant having reduced lipase activity as described herein has no activity or zero activity as compared to such a wild type plant.

In an exemplary embodiment of the present disclosure, the plant, gene edited plant, or transgenic plant having reduced lipase activity as described herein is a pearl millet which comprises a polynucleotide that encodes a polypeptide having a substitution at an amino acid position in SEQ ID NO: 2 disclosed herein as "Mut-PgTAGLip1" and which has a lipase activity reduced to 0-10%, or 10-30%, or 30-50%, or 50-70%, or 70-80%, or 80-90%, or 90-99%, of the activity level of the wild type, i.e., otherwise isogenic pearl millet plant comprising a polynucleotide that encodes a polypeptide having an amino acid as set forth in SEQ ID NO: 2.

In another exemplary embodiment of the present disclosure, the plant, gene edited plant, or transgenic plant having reduced lipase activity as described herein is a pearl millet plant which comprises a polynucleotide that encodes a polypeptide having a substitution at an amino acid position at an amino acid sequence as set forth in SEQ ID NO: 4 disclosed herein as "Mut-PgTAGLip2" and which has a lipase activity reduced to 0-10%, or 10-30%, or 30-50%, or 50-70%, or 70-80%, or 80-90%, or 90-99% of the activity level of the wild type, i.e., otherwise isogenic pearl millet plant comprising a polynucleotide that encodes a polypeptide having an amino acid as set forth in SEQ ID NO: 4.

As per an implementation of the present disclosure, the plant, gene edited plant, or transgenic plant having reduced lipase activity as described herein is a pearl millet plant which comprises a polynucleotide that encodes a polypeptide having an amino acid sequence as set forth in SEQ ID NO: 7 and which has a lipase activity reduced to 0-10%, or 10-30%, or 30-50%, or 50-70%, or 70-80%, or 80-90%, or 90-99%, of the activity level of the wild type, i.e., otherwise isogenic pearl millet plant comprising a polynucleotide that encodes a polypeptide having an amino acid sequence as set forth in SEQ ID NO: 2.

According to the implementation of the present disclosure, the plant, gene edited plant, or transgenic plant having reduced lipase activity as described herein is a pearl millet transgenic plant which comprises a polynucleotide that encodes a polypeptide having an amino acid sequence as set forth in SEQ ID NO: 9 or SEQ ID NO: 11 and which has a lipase activity reduced to 0-10%, or 10-30%, or 30-50%, or 50-70%, or 70-80%, or 80-90%, or 90-99% of the activity level of the wild type, i.e., otherwise isogenic pearl millet plant comprising a polynucleotide that encodes a polypeptide having an amino acid sequence as set forth in SEQ ID NO: 4.

As per an implementation of the present disclosure, provided is a food product (e.g., the flour or meal) made from the plant, gene edited plant, or transgenic plant having reduced lipase activity as described herein. In some examples of this implementation the shelf life of the food product is increased by 1 to 6 months as compared to the shelf life of the food product made from the wild type plant. In yet another implementation of the present disclosure, the shelf life of this food product provided herein, is increased by 1 to 5 months, or 2 to 4 months, or 3 to 4 months as compared to the shelf life of the food product of the wild type, i.e., the plant having wild type PgTAG activity. The food product as described herein can be a milled food product. In an exemplary embodiment of the present disclosure, the food product is a milled pearl millet flour or meal.

According to an implementation of the present disclosure, the free fatty acid production of the milled product of the plant, gene edited plant, or transgenic plant having reduced lipase activity as described herein is reduced by 15 to 100% as compared to the free fatty acid production of milled product made from wild type plant. In another implementation of the present disclosure, the free fatty acid production of the plant, gene edited plant, or transgenic plant having reduced lipase activity as described herein is reduced by 15 to 25%, or 25 to 50%, or 50 to 100% as compared to the free fatty production of wild type, i.e., otherwise isogenic plant having reduced lipase activity.

In an implementation of the present disclosure, there is provided a method for obtaining a transgenic plant having reduced lipase activity, said method comprising: (a) obtaining a recombinant construct as described herein, or obtaining a recombinant vector as described herein; (b) transforming plant cell(s) with the recombinant construct or recombinant vector to generate transgenic plant cell(s), (c) generating plants from the transgenic plant cells; and (d) screening the plants to obtain transgenic plants having reduced lipase activity.

Transforming plant cell(s) can be done by any suitable method such as by *Agrobacterium*-mediated transformation, particle bombardment transformation, and in-planta transformation.

Screening of plant cells or plants can comprise PCR, reverse transcriptase-PCR, quantitative real-time PCR (qRT-PCR), Southern blot, biochemical assays selected from the group consisting of acid values, lipase enzyme assays, volatile analysis, esterified lipid pool assays (showing reduced turnover), and triacyl glycerol-free fatty acid (TAG/FFA) assays.

In an implementation of the present disclosure, there is provided a method for obtaining a gene edited plant having reduced lipase activity, said method comprising providing a site-specific endonuclease to create DNA breaks that lead to modifications at the target site. transforming a host cell with the recombinant construct of step (a) or with the recombinant vector of step (a), to obtain a recombinant host cell; (c) transforming an explant is done by a method selected from the group consisting of an *Agrobacterium*-mediated transformation, particle bombardment-based method, and in-planta transformation with the recombinant construct or recombinant host cell, to obtain putative transformants, wherein the explant is selected from the group consisting of immature embryos, leaf, nodal explant, and shoot tips meristem; and (d) screening the putative transformants to obtain transgenic plants having reduced lipase activity.

In an implementation of the present disclosure, there is provided a recombinant construct comprising a heterologous promoter operably linked to a guide polynucleotide sequence, wherein the guide polynucleotide has at least 10 (e.g., 11-14, 15-29, 20, 21-25, or 26-30) contiguous nucleotides that are identical or complementary to a target polynucleotide, and wherein the target polynucleotide has a nucleotide sequence as set forth in SEQ ID NO: 1 or SEQ ID NO: 2. Optionally, such a recombinant construct can further include a heterologous promoter operably linked to a polynucleotide encoding a Cas endonuclease, wherein the guide polynucleotide with the Cas endonuclease forms a guide polynucleotide/Cas endonuclease complex, wherein said complex binds to and cleaves the target polynucleotide.

In an implementation of the present disclosure, there is provided a recombinant construct comprising a heterologous promoter operably linked to a guide polynucleotide sequence, wherein the guide polynucleotide has at least 10 (e.g., 11, 12, 13, 14, 15, 16, 17, 18, 19, or 20) contiguous nucleotides of a target polynucleotide, and wherein the target polynucleotide has nucleotides (a) from 663 to 692 of SEQ ID NO: 1 or (b) SEQ ID NO: 3. Optionally, such a recombinant construct can also include a heterologous promoter operably linked to a polynucleotide encoding a Cas endonuclease, wherein the guide polynucleotide with the Cas endonuclease that forms a guide polynucleotide/Cas endonuclease complex, wherein said complex binds to and cleaves the target polynucleotide. For example, the target polynucleotide can have nucleotides from 663 to 690, or 665 to 685, or 670 to 680 of SEQ ID NO: 1.

In an implementation of the present disclosure, there is provided a recombinant construct comprising: (a) a heterologous promoter operably linked to a guide polynucleotide, wherein the guide polynucleotide having 20 contiguous nucleotides of a target polynucleotide, wherein the target polynucleotide encodes a polypeptide having the amino acid sequence as set forth in SEQ ID NO: 4; and (b) a heterologous promoter operably linked to a polynucleotide encoding a Cas endonuclease, wherein the guide polynucleotide with the Cas endonuclease forms a guide polynucleotide/Cas endonuclease complex, wherein said complex binds to and cleaves the target polynucleotide.

In an implementation of the present disclosure, there is provided a recombinant construct comprising: (a) a heterologous promoter operably linked to a guide polynucleotide, wherein the guide polynucleotide having 20 contiguous nucleotides of a target polynucleotide, wherein the target polynucleotide has nucleotides from 531 to 561 of SEQ ID NO: 3; and (b) a heterologous promoter operably linked to a polynucleotide encoding a Cas endonuclease, wherein the guide polynucleotide with the Cas endonuclease forms a guide polynucleotide/Cas endonuclease complex, wherein said complex bind to and cleave the target polynucleotide. In another implementation of the present disclosure, the target polynucleotide has nucleotides from 531 to 560, or 535-555, or 540-550 of SEQ ID NO: 3.

According to the present disclosure, the guide polynucleotide is selected from the group consisting of polynucleotide having the nucleotide sequence as set forth in SEQ ID NO: 60, SEQ ID NO: 61, SEQ ID NO: 62, SEQ ID NO: 63, SEQ ID NO: 64, SEQ ID NO: 65, SEQ ID NO: 72, SEQ ID NO: 73, SEQ ID NO: 74, SEQ ID NO: 75, SEQ ID NO: 76, and SEQ ID NO: 77.

As per the implementation of the present disclosure, the recombinant construct as described herein, wherein the heterologous promoter is selected from the group consisting of CaMV 35S, Ubi, AXIG1, and U6.

In an implementation of the present disclosure, there is provided a recombinant host cell comprising the recombinant construct as described herein.

According to the present disclosure, there is provided a recombinant host cell as described herein, wherein the recombinant host cell is selected from the group consisting of bacteria, yeast and plant.

In an implementation of the present disclosure, there is provided a method for obtaining a gene edited plant having reduced lipase activity, said method comprising: (a) obtaining a recombinant construct, said recombinant construct comprising: (i) a heterologous promoter operably linked to a guide polynucleotide, wherein the guide polynucleotide having 20 contiguous nucleotides of a target polynucleotide, and wherein the target polynucleotide has a nucleotide sequence as set forth in SEQ ID NO: 1; and (ii) a heterologous promoter operably linked to a polynucleotide encoding a Cas endonuclease, wherein the guide polynucleotide with the Cas endonuclease forms a guide polynucleotide/Cas endonuclease complex, wherein said complex binds to and cleaves the target polynucleotide; (b) transforming a host cell with the recombinant construct of step (a) to obtain a recombinant host cell; (c) transforming an explant with the recombinant host cell, to obtain putative transformants; and (d) screening the putative transformants to obtain the gene edited plant having reduced lipase activity.

In an implementation of the present disclosure, there is provided a method for obtaining a gene edited plant having reduced lipase activity, wherein transforming the explant is done by a method selected from the group consisting of an *Agrobacterium*-mediated transformation, particle bombardment-based method, and in-planta transformation.

In an implementation of the present disclosure, there is provided a method for obtaining a gene edited plant having reduced lipase activity as described herein, wherein screening comprises PCR, reverse transcriptase-PCR, quantitative real-time PCR (qRT-PCR), Surveyor nuclease assay, and DNA Sequencing.

In an implementation of the present disclosure, there is provided a method for obtaining a gene edited plant having reduced lipase activity as described herein, wherein the explant is selected from the group consisting of immature embryos, leaf, nodal explant, and shoot tips meristem.

In an implementation of the present disclosure, there is provided a gene edited plant having reduced lipase activity obtained using the method, said method comprising: (a) obtaining a recombinant construct as described herein; (b) transforming a host cell with the recombinant construct of step (a) to obtain a recombinant host cell; (c) transforming an explant with the recombinant host cell, to obtain putative transformants; and (d) screening the putative transformants to obtain gene edited plant having reduced lipase activity.

As per one of the implementations of the present disclosure, the gene edited plant has SDN-1 and/or SDN-2 type mutations.

In an implementation of the present disclosure, there is provided a gene edited plant having reduced lipase activity as described herein, wherein the gene edited plant exhibits a characteristic selected from the group consisting of: (a) reduced free fatty acid production; (b) reduced hexanal production; (c) increased oxidative stability; (d) increased hydrolytic stability; (e) reduced volatiles production; and (f) improved sensory characteristics (e.g., reduced rancidity).

As per one of the implementations of the present disclosure, there is also provided is a method of screening for the presence or absence of the isolated polynucleotide as described herein in a plurality of genomic pearl millet DNA samples. Methods of extracting modified (mutated) DNA from a sample or detecting the presence of DNA corresponding to the modified genomic sequences comprising insertion, deletions or substitutions in SEQ ID NO: 2, or SEQ ID NO: 4 are provided. Such methods comprise contacting a sample comprising pearl millet genomic DNA with a DNA primer set, that when used in a nucleic acid amplification reaction, such as the polymerase chain reaction (PCR), with genomic DNA extracted from pearl millet plant produces an amplicon that is diagnostic for either the presence or absence of the modified or mutated polynucleotide. The methods include the steps of performing a nucleic acid amplification reaction, thereby producing the amplicon and detecting the amplicon. In one embodiment of the present disclosure, one of the pair of DNA molecules comprises the wild type sequence where the modification such as a deletion occurs with the second of the pair being upstream or downstream as appropriate and suitably in proximity to the wild type sequence where the modification such as deletion occurs, such that an amplicon is produced when the wild type allele is present, but no amplicon is produced when the modified allele is present.

In an implementation of the present disclosure, there is provided a method of detecting one or more pearl millet plants with reduced lipase activity, said method comprising: (a) obtaining nucleic acid from one or more pearl millet plants; and (b) detecting mutations in a polynucleotide encoding a polypeptide having an amino acid sequence as set forth in SEQ ID NO: 2, wherein the mutations are selected from the group consisting of: (i) a polynucleotide encoding a polypeptide having a substitution at an amino acid position in SEQ ID NO: 2, wherein the substitution at the amino acid position is selected from the group consisting of positions at 12, 18, 19, 20, 23, 26, 37, 38, 42, 43, 44, 96, 97, 98, 114, 131, 135, 144, 145, 146, 167, 168, 169, 172, 205, 206, 215, 221, 222, 237, 246, 263, 289, 290, 298, 299, 330, 339, and 346; (ii) a polynucleotide encoding a polypeptide having an amino acid sequence as set forth in SEQ ID NO: 7; (iii) a polynucleotide having an amino acid sequence as set forth in SEQ ID NO: 13; SEQ ID NO: 15, SEQ ID NO: 17, SEQ ID NO: 19, SEQ ID NO: 21, and SEQ ID NO: 25; (iv) a polynucleotide having a nucleotide sequence as set forth in SEQ ID NO: 22.

In an implementation of the present disclosure, there is provided a method of detecting one or more pearl millet plants with reduced lipase activity, said method comprising: (a) obtaining nucleic acid from one or more pearl millet plants; and (b) detecting mutations in a polynucleotide encoding a polypeptide having an amino acid sequence as set forth in SEQ ID NO: 4, wherein the mutations are selected from the group consisting of: (i) a polynucleotide encoding a polypeptide having an amino acid sequence as set forth in SEQ ID NO: 9, and SEQ ID NO: 11; and (ii) a polynucleotide having a nucleotide sequence selected from the group having the sequence as set forth in SEQ ID NO: 26, SEQ ID NO: 28, and SEQ ID NO:30.

In an implementation of the present disclosure, there is provided a method of detecting one or more pearl millet plants with reduced lipase activity, said method comprising: (a) obtaining nucleic acid from one or more pearl millet plants; and (b) detecting mutations in a polynucleotide as set forth in SEQ ID NO: 2, or SEQ ID NO: 4, wherein detecting the mutations is carried out by PCR followed by sequencing.

In an implementation of the present disclosure, there is provided a method of producing a pearl millet plant with reduced lipase activity, said method comprises: (a) obtaining a pearl millet plant with reduced lipase activity, wherein the plant is identified with a mutation in a lipase gene, and wherein the mutation is selected from the group consisting of: (i) a polynucleotide encoding a polypeptide having a substitution at an amino acid position in SEQ ID NO: 2, wherein the substitution at the amino acid position is selected from the group consisting of positions at 12, 18, 19, 20, 23, 26, 37, 38, 42, 43, 44, 96, 97, 98, 114, 131, 135, 144, 145, 146, 167, 168, 169, 172, 205, 206, 215, 221, 222, 237, 246, 263, 289, 290, 298, 299, 330, 339, and 346; (ii) a polynucleotide encoding a polypeptide having an amino acid sequence as set forth in SEQ ID NO: 7; (iii) a polynucleotide encoding a polypeptide having an amino acid sequence as set forth in SEQ ID NO: 13; SEQ ID NO: 15, SEQ ID NO: 17, SEQ ID NO: 19, SEQ ID NO: 21, and SEQ ID NO: 25; and (iv) a polynucleotide having a nucleotide sequence as set forth in SEQ ID NO: 22; (b) crossing the plant having reduced lipase activity showing a mutation in the lipase gene with a second plant having normal lipase activity to obtain a hybrid; and (c) obtaining seeds from the hybrid of step (b); and (d) producing pearl millet plant from said seeds, wherein said plant produced from said seeds comprises said mutation, and wherein said plant shows reduced lipase activity.

In an implementation of the present disclosure, there is provided a method of producing a pearl millet plant with reduced lipase activity, said method comprises: (a) obtaining a pearl millet plant with reduced lipase activity, wherein the plant is identified with a mutation in a lipase gene, and wherein the mutation is selected from the group consisting of: (i) a polynucleotide encoding a polypeptide having a substitution at an amino acid position in SEQ ID NO: 4 wherein the substitution at the amino acid position is selected from the group consisting of positions at 220, 223, 265, 316, 317, 318, 319, 320, 321, 322, 323, 324, 325, 326, 327, 328, 329, 330, 331, and 332; (ii) a polynucleotide encoding a polypeptide having an amino acid sequence as set forth in SEQ ID NO: 9, and SEQ ID NO: 11; and (iii) a polynucleotide having a nucleotide sequence selected from the group having the sequence as set forth in SEQ ID NO: 26, SEQ ID NO: 28, and SEQ ID NO:30; (b) crossing the plant having reduced lipase activity showing a mutation in the lipase gene with a second plant having normal lipase activity to obtain a hybrid; (c) obtaining seeds from the hybrid of step (b); and (d) producing pearl millet plant from said seeds, wherein said plant produced from said seeds comprises said mutation, and wherein said plant shows reduced lipase activity.

In an implementation of the present disclosure, there is provided a food product from the transgenic plant or the gene-edited plant as described herein.

In an implementation of the present disclosure, there is provided a food product from the transgenic plant or the gene-edited plant as described herein, wherein the food product is selected from the group consisting of flour, meal, whole grain, and broken grain.

In another implementation of the present disclosure, there is provided a flour from the transgenic plant or the gene-edited plant as described herein.

In yet another implementation of the present disclosure, there is provided a broken grain from the transgenic plant or the gene-edited plant as described herein.

As per one of implementation of the present disclosure, the food product as described herein exhibits characteristic features selected from the group consisting of: (a) reduced rancidity; (b) reduced lipase activity; (c) increased shelf life.

According to the present disclosure, the food product can be used in a form selected from group consisting of bakery goods, confectionary items, weaning foods, or dietary formulations.

As per one of the implementations of the present disclosure, the food product can be prepared by a method selected from the group consisting of milling, extrusion, baking, or malting.

In an implementation of the present disclosure, the food product as described herein is a flour, wherein the flour is a milled flour.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

Example 1

Identification of the Pearl Millet Genotypes Contrasting for the Rancidity

This example demonstrates a time course experiment which was designed to measure the development of rancidity in Pearl millet (*Pennisetum glaucum* L.) flours. Five Pearl millet varieties were selected for this study (as shown in Table 1). Thirty-gram samples of each line were ground to fine powders in a custom built (Wolfe Machinery Company, Johnston IA) industrial burr-mill grinder. Particle size analysis was performed on samples of the dehulled and whole seed (Johnny's) to determine the grinding quality. A RO-TAP® (model RX-29; W.S. Tyler Co, Mentor, OH), was used following the ANSI/ASAE S319.4 Feb. 2008 R2012, protocol with a flow agent (Sipernat®; Evonik, Essen, Germany). Greater than 95% of the ground flours passed through a 30-mesh sieve (<600μ), with the bulk of the material falling in the 150-300μ range. Table 1 shows the identity, form and sources of seed used in study.

TABLE 1

| Line Abbreviation | Variety | Form | Source |
|---|---|---|---|
| DS | Whole Grain Millet | Dehulled | Bob's Red Mill ®; grocery store |
| JWS | Hybrid Pearl Millet F1 | Whole Seed | Johnny's Selected Seeds, (Product ID 187) |
| I3 | Line 3 | Whole Seed | ICRISAT, Hyderabad, India |
| I5 | Line 5 | Whole Seed | ICRISAT, Hyderabad, India |
| I7 | Line 7 | Whole Seed | ICRISAT, Hyderabad, India |

The ground flours were spread into evenly distributed layers in lidless food grade trays (Rubber Maid). After removal of approximately 3.0 g samples for analysis, the trays were placed onto the lowest shelf of an environmentally controlled cabinet. The Nalgene desiccator cabinet (30.5×30.5×30.5 cm; Part #5317-0120) had a shallow tray containing a super saturated solution of Sodium Chloride (200 g NaCl in 100 ml DI water) placed on the bottom of the cabinet. The cabinet housed in a forced draft incubator set at 35° C. A small fan placed in a lateral position in the upper third of the cabinet was used to equilibrate the temperature and moisture conditions. Environmental conditions within the cabinet were monitored throughout the experiment with two iButton Hydrochron (DS1923; Maxim Integrated Products Inc. San Jose, Ca) temperature and moisture dataloggers. Conditions were monitored every ten minutes with one of the loggers placed on the shelf holding the samples and the other on the frame holding the fan. The average conditions measured within the chamber during the experiment were 35.4+/−0.2° C. and 71.4+/−3.1% RH. Sub-samples of flour were collected subsequently at seven-day intervals to 21 days for four time points (0, 7, 14, and 21 days).

The flours were split into sub-fractions at each sampling, which were used for separate analytical procedures. Sub-fractions for lipid analysis were lyophilized overnight. Total lipids were extracted from 20 mg or 100 mg of the lyophilized tissue, for High-performance liquid chromatography (HPLC) and Gas Chromatography (GC) analysis, respectively. Three mL of methanol:chloroform (2:1 v/v) was added to each sample followed by shaking for 15 min at room temperature. Phase separation was induced by the addition of 1 mL chloroform and 1.8 mL water.

The samples were vortexed thoroughly and centrifuged at 1000×g for 5 minutes before the lower lipid-containing layer was collected. Each sample was re-extracted twice with 2 mL chloroform. The re-extracted lipid fractions were combined with the initial lipid extract. Lipid extracts were then filtered with a 0.2 μm Polytetrafluoroethylene (PTFE) filter and dried under a stream of nitrogen gas.

Triacylglycerol (TAG) and free fatty acids (FFA) were quantified by HPLC-ELSD. Samples were resuspended in 160 μL of 1:1 chloroform:methanol and 1 μL sample was injected on the HPLC. Lipid species were separated on a cyanopropyl column (Luna 5 μm CN 100 Å 250×4.6 mm; Phenomenex) with hexane as mobile phase A and methyl tertiary-butyl ether (MTBE):isopropanol (95:5 v/v) plus 0.2% acetic acid as mobile phase B, with a gradient of 0% to 100% B, and re-equilibration of the column to 0% B. Standard curves of tri-C18:2 TAG, and 18:2 FFA were run with each sample set to quantify total TAG and FFA as a percent of dry weight (DW).

Fatty acid profiles were determined for samples collected at the 0-day time point by gas chromatography with flame-ionization detection (GC-FID).

Lipid extracts were derivatized to form Fatty acid methyl esters (FAMES) by adding 1 mL of 5% sulfuric acid in methanol followed by heating at 90° C. for 1 hour. Phase separation was induced by the addition of 1 mL of 1M NaCl and 1 mL heptane. After vortexing and centrifugation, the upper heptane layer was transferred to a sample vial for analysis. FAME separation was performed on a GC system (Agilent 7890A) with an OmegaWax 320 column (Supelco) followed by FID analysis. The GC oven temperature was set at a starting temperature of 190° C., then increased to 240° C. at 5° C./min, with a total run time of 10 min.

Results

Figure 1:
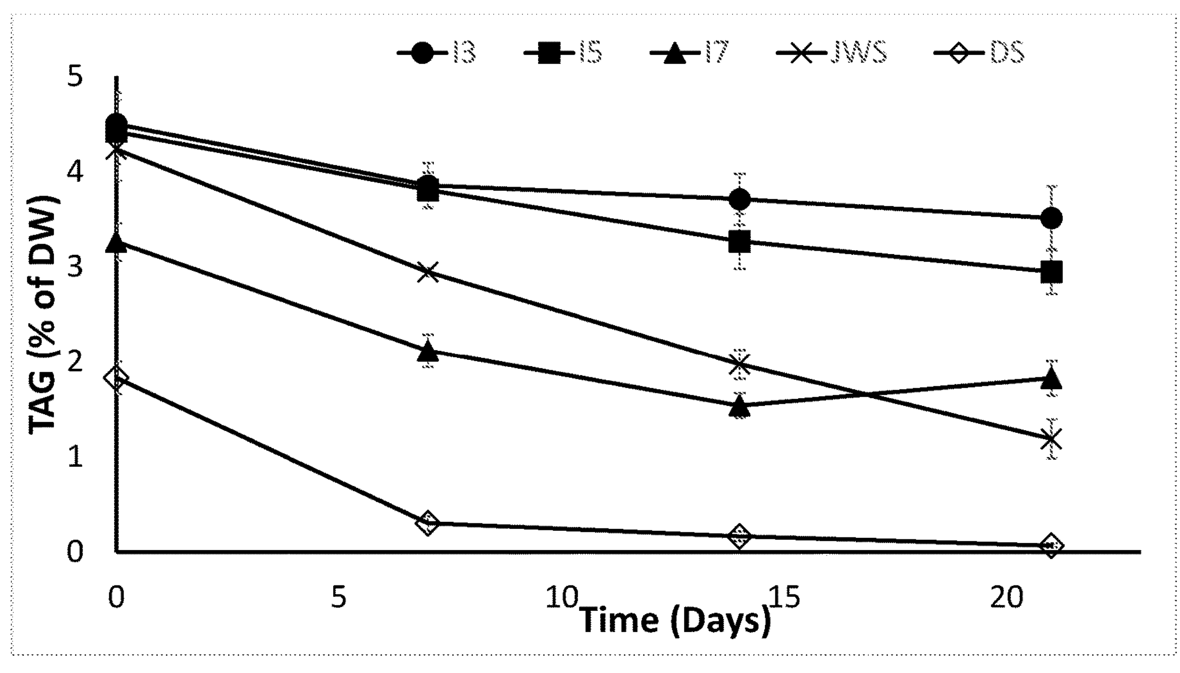
FIG. 1 depicts a decrease in triacylglycerol (TAG) extracted from pearl millet flour. Error bars represent the standard deviation of 3 separate lipid extractions at each time point.
Figure 2:
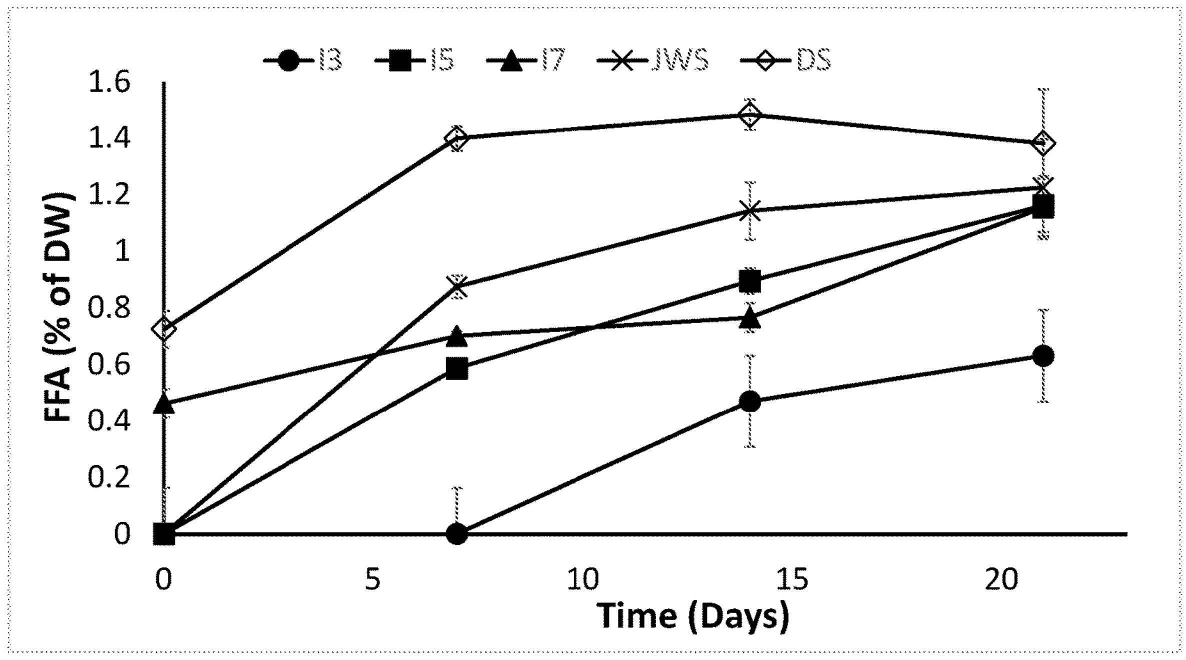
FIG. 2 depicts an increase in free fatty acid (FFA) extracted from pearl millet flour. Error bars represent the standard deviation of 3 separate lipid extractions at each time point.

Quantitation of neutral lipids by HPLC-ELSD showed that for all lines (DS, JWS, I3, I5, I7), TAG levels decreased over time, as shown in FIG. 1, while FFA levels increased, as depicted in FIG. 2. The DS and JWS lines accumulated the most FFA, corresponding to a rapid breakdown in TAG. The I3 line accumulated FFAs at a slower rate compared to all other lines. FFAs were not present at detectible levels in I3 samples at the 7-day timepoint. By 14 days, FFAs accounted for less than 0.5% of dry weight (DW) and at 21 days, FFAs were less than 0.7% of DW in I3 samples. These levels are low in comparison to the other lines tested, which had 0.8-1.5% FFAs at 14 days and 1.2-1.4% at 21 days. The I3 line also had the smallest decrease in TAG levels throughout the time course.

Fatty acid profiles (as shown in Table 2) showed that 18:2 fatty acid was dominant for all lines tested. The dehulled seed had higher levels of 18:2 compared to whole seed varieties. Among whole seed varieties, there were minimal differences in fatty acid composition. Table 2: Fatty acid profiles of samples collected at the 0-day time point.

TABLE 2

| Line | C16:0 | C18:0 | C18:1 |
|---|---|---|---|
| I3 | 16.94 ± .09 | 4.42 ± .03 | 30.60 ± .09 |
| I5 | 16.22 ± .04 | 4.41 ± .01 | 32.02 ± .05 |
| I7 | 17.18 ± .05 | 4.31 ± .01 | 34.72 ± .09 |
| JWS | 16.91 ± .02 | 3.68 ± .03 | 29.03 ± .12 |
| DS | 8.80 ± .08 | 1.67 ± .00 | 22.62 ± .09 |
| **Line** | **C18:2** | **C18:3** | **C20:0** |
| I3 | 44.42 ± .09 | 2.79 ± .05 | .82 ± .01 |
| I5 | 43.64 ± .08 | 2.82 ± .02 | .90 ± .00 |
| I7 | 40.03 ± .08 | 2.84 ± .03 | .93 ± .01 |
| JWS | 46.34 ± .09 | 3.31 ± .02 | .72 ± .00 |
| DS | 65.14 ± .16 | 1.21 ± .00 | .57 ± .01 |

Therefore, it can be inferred from Table 2, FIG. 1 and FIG. 2 that differences in the rate of TAG breakdown, including increased TAG stability in the I3 line, was not due to the fatty acid composition. Overall, it can be inferred that the I3 line had the lowest levels of free acids among all the Pearl millet lines tested.

Example 2

Determining Levels of Hexanal, Biproduct of Fatty Acid Oxidation

Head Space Analysis Samples.

In the present example, the levels of hexanal of each Pearl millet varieties (DS, JWS, I3, I5, I7) as shown in Table 1 were analysed by head space analysis. For this purpose, three 0.5 g samples for each variety were individually weighed (to an accuracy of 0.0001 g) into 20 mL amber glass headspace vials (Gerstel Part #093640-037-00). The vials were tightly capped and stored at −20° C. until further analysis (performed within 1 week of sampling). Prior to analysis, the vials were brought to room temperature and were incubated at 35° C. for one hour prior to GC-MS analysis on an Agilent 7890 Gas Chromatography system fitted with an Agilent 5977B Mass spectrometer and a Gerstel Multi-Purpose Sampler (MPS Robotic; Gerstel, Linthicum, MD) with automated Solid Phase Micro-Extraction (SPME) sampling capability.

The split/splitless inlet used for sample introduction was fitted with a Topaz SPME inlet Liner (Part #23434; Restek, PA). The robotic sampler was fitted with a 23 Gauge SPME fiber assembly (divinylbenzene/Carboxen/polydimethylsiloxane (DVB/CAR/PDMS; Millipore-Sigma Part #52729-U). Prior to analysis, the SPME fiber was conditioned by exposing the fiber in the heated inlet (265° C. at a 100:1 split ratio with He as the carrier gas) and maintaining it there throughout the chromatographic cycle. The column (Ultra-1 50 m×0.32, 0.52 u film thickness; Agilent part #19091A-1115) flow rate was held constant (1.1 mL per minute). The sampling sequence performed two complete regeneration cycles of the fiber before beginning the sampling run. The sampling run started with an empty headspace vial to monitor any potential carryover and to establish a chromatographic baseline. Ester standards were used to establish retention time indices and were run at the beginning and end of each sample set. The ethyl esters, ethyl acetate through ethyl tetra-decanoate, were prepared at a nominal concentration of 0.0035% (v:v) in high oleic vegetable oil. Two μL aliquots were placed into empty headspace vials and were sampled in the same manner as the samples and empty vial blanks.

For samples, the robotic sampler introduced the headspace vials into a block heater (at 70° C.) which agitated (250 rpm) them for 5 min prior to introduction of the SPME sampling needle and exposure of the fiber. After 20 min the fiber was retracted and the SPME sampling device was transferred to the split/splitless inlet of the gas chromatograph for desorption and analysis. With the inlet set at 250° C. in a splitless mode the fiber was exposed to start the cycle. After 5 min in the inlet, the split vent was opened (30 mL/min) and this state was retained until the next sampling cycle began. The column oven was maintained at 40° C. for the first 5 min after sample introduction and was then ramped (12° C./min) to 240° C., with a 1 min hold, before ramping (30° C./min) to 325° C., which was held for 4 min prior to cycling back to the starting conditions prior to the cycle starting again. Gerstel Maestro™ control software was used to orchestrate the sampling process, allowing sampling and analysis phase overlap. Data analysis was performed using Agilent Mass Hunter Quantitative software.

Results

The results of the Headspace Analysis of ground flours are depicted in FIG. 3. Referring to FIG. 3, it can be observed that the I3 line had the lowest levels of headspace hexanal, a known oxidation product of linoleic acid, accumulating in the headspace above flours exposed to 21 days of accelerated aging. Conversely, the dehulled seed flours (DH) had the highest levels of headspace hexanal.

These results as depicted in FIG. 3 are consistent with the hypothesis that the low levels of free fatty acids present in the I3 flours, after 21 days of accelerated aging (as demonstrated in Example 1), were related to lower levels of lipid oxidation (rancidity), as indicated by the lower levels of hexanal in the headspace.

Example 3

Increased Shelf Life in Pearl Millet Lines Carrying Dysfunctional Mutants.

The pearl millet flour was made from pearl millet grains in a cyclotec grinding mill (Foss Analytical AB, Sweden) and either used immediately for chemical analysis or stored in BPA-free GLAD containers (4 oz/118 mL) for 21 days under accelerated conditions at a temperature of 35° C. and 70% RH. Samples of the stored flour was withdrawn at 0, 7, 14 and 21 days for biochemical analysis, such as acid value, polyphenol oxidase and peroxidase activities.

(a) Measurement of Acid Value and Polyphenol Oxidase & Peroxidase Activities

Total crude fat was extracted in a Soxhlet apparatus from 5 g flour using a modified protocol based on the method of the Association of Official Analytical Chemists (AOAC 1990). Briefly, 5 g of flour was taken in a nitrocellulose thimble. The thimble was suspended in a pre-weighed extraction beaker containing 100 ml petroleum ether or diethyl ether and kept on a hot plate until the sample started to boil. The extracted oil was titrated against 0.1 N KOH using phenolphthalein as indicator. The end point was recorded. The acid value was calculated using the formula:

Acid value (AV) mg KOH/g=Titrate value×Normality of KOH×56.1/Weight of sample

The polyphenol oxidase (PPO) and peroxidase (POD) activities of ground pearl millet seeds were recorded for each time interval. The 100 mg of flour was homogenized in 1 mL of PBS buffer (pH 7.5) and centrifuged at 3000 rpm for 20 min. The extracted enzyme was assayed by kit (Biosource) method and absorbance was measured at 450 nm on an ELISA plate reader. One unit of enzyme activity of POD or PPO was defined as the amount of enzyme required to increase 0.1-unit absorbance $min^{-1}$ g $d{\cdot}m{\cdot}^{-1}$ (dry matter) under the test conditions.

(b) Biochemical Determinants of Rancidity

Crude fat content of stored flour of the genotypes varied from 4.2 to 7.2%. The study indicated the existence of significant diversity in the rancidity profile among the selected lines. Acid value of fresh flour (day 0) varied from 5.15 to 12.37 mg KOH/g and 7.7 to 13.6 mg KOH/g in a set of pearl millet inbred and diversity panel lines, respectively. Upon accelerated storage on day 7, the Acid value (AV) increased in range of 15.41-28 mg KOH/g in the low rancid mutants compared to 43-88. 1 mg KOH/g in the rancidity prone lines. On day 14, the AV increased up to 104.6 mg KOH/g in the rancidity prone lines as compared to 59-65.53 mg KOH/g recorded in low rancid mutants (Table 3). Table 3 shows Acid Values (AV) for pearl millet inbred and diversity panel lines at 0, 7, and 14 days after milling and storage under accelerated storage conditions.

TABLE 3

| Genotypes | AV 0 days | AV 7 days | AV 14 days |
|---|---|---|---|
| I1 | 10.14 ± 0.2 | 27.135 ± 0.80 | 83.77 ± 3.52 |
| I2 | 5.15 ± 0.36 | 15.41 ± 2.61 | 63.11 ± 1.2 |
| I3 | 14.62 ± 0.39 | 27.85 ± 3.32 | 65.53 ± 3.43 |
| I4 | 11.83 ± 1.93 | 35.55 ± 4.9 | 67.33 ± 2.71 |
| I5 | 9.17 ± 0.01 | 42.36 ± 1.56 | 72.32 ± 6 |
| I6 | 6.90 ± 0.63 | 30.01 ± 2.36 | 96.19 ± 2.87 |
| I7 | 10.94 ± 0.30 | 43.01 ± 1.6 | 73.45 ± 2.15 |
| P13 | 11.3 ± 0.49 | 21.2 ± 0.25 | 64.2 ± 0.85 |
| P14 | 13.0 ± 0.61 | 30.9 ± 0.29 | 79.4 ± 0.63 |
| P15 | 7.7 ± 0.39 | 26.9 ± 0.93 | 59.1 ± 0.35 |
| P16 | 12.8 ± 0.48 | 88.1 ± 0.21 | 104.1 ± 1.74 |
| P17 | 13.6 ± 1.36 | 43.2 ± 0.50 | 72.6 ± 0.46 |
| I8 | 12.37 ± 2.69 | 38.16 ± 2.45 | 49.28 ± 2.3 |
| I9 | 9.515 ± 1.21 | 28.5 ± 1.46 | 46.48 ± 1.84 |

In another study done under accelerated storage conditions, the delta values (change from Day 0) calculated for AV on day 10 and 21, revealed that low rancid lines (I1, I2, and I3) had significantly lower rates of increase in AV, with 9-19.1 mg KOH/g and 51.3-66.35 mg KOH/g on day 10 and 21, respectively. In contrast, the high rancid line I5 had a change of (Δ) AV of 75.32 and 91.36 mg KOH/g on day 10 and 21, respectively (FIG. 4).

Example 4

Expression Analyses of PgTAG Lipases in Flours During Early Onset of Rancidity and TAG Mobilization During Germination.

To study gene expression, the flour samples were collected at 0 h, 6 h, 12 h, and 24 h exposure to accelerated aging conditions and used for total RNA extraction using RNeasy Plant Mini kit (Qiagen, Germany) and their quantity and quality analyzed using NanoVue plus spectrophotometer (GE health care, USA). 1.5 μg of total RNA was used for cDNA synthesis using Superscript III (Invitrogen) and samples diluted 1:10 times were used as a template. qRT-PCR was carried out in 96-well optical reaction plates, with a total reaction volume of 10 μL containing 0.5 μM of each primer (0.8 μL), cDNA (1.0 μL), and Sensi Master Mix (2×) and $dH_2O$ were added up to 3.2 μL. The qRT-PCR primers (as shown in Table 4) were designed using Primer3 software (v.0.4.0) (Untergasser A, Cutcutache I, Koressaar T, Ye J, Faircloth B C, Remm M, Rozen S G (2012) Primer3—new capabilities and interfaces. Nucleic Acids Research 40(15): e115).

Table 4 lists qRT-PCR primers with GC content of 40-60%, a $T_m$ of 60-62° C., primer length 20-25 nucleotides, for an expected product size of 90-180 bp. The qRT-PCR reactions were carried out using standard thermal profile: 95° C. for 10 s, 40 cycles of 15 s at 95° C., 15 s at 61° C. with fluorescent signal recording and 15 s at 72° C. After the $40^{th}$ cycle, amplicon dissociation curves were measured by heating at 58 to 95° C. with fluorescence measured within 20 min. All qRT-PCR data were obtained from three biological replicates with three technical replicates. Normalized expression was calculated with qBase+ software (Schmidt and Delaney 2010) with reference genes eukaryotic initiation factor4α (PgEIF4α) and Malate dehydrogenase (PgMDH) (Reddy P S, Reddy D S, Sharma K K, Bhatnagar-Mathur P, Vadez V (2015) Cloning and validation of reference genes for normalization of gene expression studies in pearl millet [*Pennisetum glaucum* (L.) R. Br.] by quantitative real-time PCR. Plant Gene 1: 35-42).

TABLE 4

| SEQ ID | Description | Sequence |
|---|---|---|
| SEQ ID NO: 36 | PgTAGLip1_qF1 | GCGTGTTTGTGCTGTTCTGG |
| SEQ ID NO: 37 | PgTAGLip1_qR1 | TTGCCCCATGACGATTCTGC |
| SEQ ID NO: 38 | PgTAGLip1_qF2 | TATGGTGCTCTTGCTGCTGT |
| SEQ ID NO: 39 | PgTAGLip1_qR2 | TCGGGTTCTGTGTTGGACTC |
| SEQ ID NO: 40 | PgTAGLip1_qF3 | TGTTGCAATAAGGGGAACTCA |
| SEQ ID NO: 41 | PgTAGLip1_qR3 | GACCTTAGCATTGGGCATGT |
| SEQ ID NO: 52 | PgTAGLip2_qF1 | GGCTGCGAAGGGCGCGACGG |
| SEQ ID NO: 53 | PgTAGLip2_qR1 | AACCGCCATCAGAAGGCTTC |
| SEQ ID NO: 54 | PgTAGLip2_qF2 | TGCTAGAGAGGTTTGGCTTCA |
| SEQ ID NO: 55 | PgTAGLip2_qR2 | TGATCTGCCACACTTATTCCA |
| SEQ ID NO: 56 | PgTAGLip2_qF3 | TTCAAGGGGATCTTGTCAATTT |
| SEQ ID NO: 57 | PgTAGLip2_qR3 | TGATTCTTGCGCATATTTTGA |

TABLE 4-continued

| SEQ ID | Description | Sequence |
|---|---|---|
| SEQ ID NO: 42, 58 | PgEif4a_qF4 | ATCGTGAGCTTTACATCCATCG |
| SEQ ID NO: 43, 59 | PgEif4a_qR4 | TATCCCTCAGGATACGGATGTC |

In general, under accelerated storage conditions at 35° C. and RH of 75%, the expression of PgTAG Lipase 1 gene or PgTAGLip1 (SEQ ID NO: 1) and PgTAG Lipase 2 gene or PgTAGLip2 (SEQ ID NO: 3) significantly increased in medium and high rancid lines (I5 and I7, respectively) within 24 h, as shown in FIG. 5. The expression of PgTAGLip1 gene and PgTAGLip2 gene was considerably lower in low rancid mutant line (I3) throughout, as also shown in FIG. 5.

In general, under accelerated storage conditions at 35° C. and RH of 75%, the expression of PgTAG Lipase 1 gene or PgTAGLip1 (SEQ ID NO: 1) and PgTAG Lipase 2 gene or PgTAGLip2 (SEQ ID NO: 3) significantly increased in medium and high rancid lines (I5 and I7, respectively) within 24 h, as shown in FIG. 5. The expression of PgTAGLip1 gene and PgTAGLip2 gene was considerably lower in low rancid mutant line (I3) throughout, as also shown in FIG. 5.

Grains were disinfected with 80% (v/v) ethanol and 0.05% (w/v) mercuric chloride solution followed by stratification for 2 days at 4° C. in moistened filter papers by placing in sterile Petri plates. Imbibed grains were transferred to growth chamber at 26° C. and were sampled for lipid analysis on day 1 at 0, 6 and 24 hours after imbibition (HAI), and subsequently after 2, 5 and 7 days after imbibition (DAI).

Further, to determine the difference of storage lipid mobilization between mutants, TAG breakdown was measured during the seed germination, from 0 DAI to 7 DAI. I3 accumulated significantly higher TAG until 24 hrs which reduced thereafter until day 7. In I7, TAG mobilization started almost immediately from 4$^{th}$ day onwards coinciding with germination (FIG. 6). No significant differences were observed in the rate of germination or post-germinative seedling establishment or growth, indicating that while the mutations in both candidate lipases might be useful for TAG hydrolysis, these were not essential for germination and there could be other lipase gene(s) complementing this function.

Example 5

Identification of Mutant Alleles (a) Genomic DNA Isolation

Genomic DNA isolation was carried out by cetyltrimethylammonium bromide (CTAB) method (Lodhi M A, Guang-Ning Y, Norman F W, Bruce I R (1994) A simple and efficient method for DNA extraction from grapevine cultivars, *Vitis* species and *Ampelopsis*. Plant Mol Biol Rep 12:6-13) to capture most of the mutations in plants that carried a mutation at one or more of the PgTAGLip1 (SEQ ID NO: 1) and PgTAGLip2 loci (SEQ ID NO: 3).

PgTAGLipase 1 or PgTAGLip1 having nucleotide sequence as set forth in SEQ ID NO: 1 encodes a protein (PgTAGLIP1) having an amino acid sequence as set forth in SEQ ID NO: 2, whereas, PgTAGLipase2 or PgTAGLip2 having nucleotide sequence as set forth in SEQ ID NO: 3 encodes a protein (PgTAGLIP2) having an amino acid sequence as set forth in SEQ ID NO: 4.

Preferably, pooled plant samples of two or more individual pearl millet lines were subjected to genomic DNA isolation and PgTAGLip1 and PgTAGLip2 sequence-specific amplification using Polymerase Chain Reaction (PCR). Primers specific to PgTAGLip1 and PgTAGLip2 locus or the sequences immediately adjacent to one of these loci may amplify the PgTAGLip1 and PgTAGLip2 gene sequences within the pooled DNA sample. The primers that were designed to detect exonic regions of one or more PgTAGLipase genes are listed in Table 5.

Table 5 lists the primers specific to PgTAGLip1 and PgTAGLip2 locus

TABLE 5

| SEQ ID | Description | Sequence |
|---|---|---|
| SEQ ID NO: 32 | PgTAGLip1_F1 | ATGGATAGGCGGAGACGCGCGGT |
| SEQ ID NO: 33 | PgTAGLip1_R1 | TCAAACGACCTGGACGCTATTGTC |
| SEQ ID NO: 48 | PgTAGLip2_F1 | ATGGCTGCGAAGGGCGCGAC |
| SEQ ID NO: 49 | PgTAGLip2_R1 | TCATATGGATTCTAGGATATG |

The primers were designed based upon the PgTAG Lipase genes of pearl millet: PgTAGLip1 (SEQ ID NO: 1) and PgTAGLip2 (SEQ ID NO: 3). Table 6 shows exemplary primers that are useful in identifying mutations in PgTAGLip1 (SEQ ID NO: 1) and PgTAGLip2 (SEQ ID NO: 3) of pearl millet

TABLE 6

| SEQ ID NO: | Description | Sequence |
|---|---|---|
| SEQ ID NO: 94 | PgTAGLip1_F | ACAGACCTAACGGCTCTATACAC |
| SEQ ID NO: 95 | PgTAGLip1_R | GCATTGAGATTGTGATCAACAC |
| SEQ ID NO: 96 | PgTAGLip1_2F | GCATACAGAACTGGATTAAGGA |
| SEQ ID NO: 97 | PgTAGLip1_2R | AGCCTTGCGAACAGCATTCGTG |
| SEQ ID NO: 98 | PgTAGLip1_3F | GCTAGGAAGTTGCATGGAGAT |
| SEQ ID NO: 99 | PgTAGLip1_3R | ATTCTGATTGTGTTTGGCAC |
| SEQ ID NO: 100 | PgTAGLip2_F | ATGGCTGCGAAGGGCGCGAC |
| SEQ ID NO: 101 | PgTAGLip2_R | CAATCACCTCAAAGCCCTTT |
| SEQ ID NO: 102 | PgTAGLip2_1F | CTGGTCTCCGCTCCTCCTAC |
| SEQ ID NO: 103 | PgTAGLip2_1R | TTCGCCACATCCACAATGACC |
| SEQ ID NO: 104 | PgTAGLip2_2F | GACCCAACCTGCAGCAGGTC |
| SEQ ID NO: 105 | PgTAGLip2_2R | TCTAGGATATGTGATTCTTG |

The primers in Table 5 were also used for identifying intact versus missing PgTAGLipases complementary cDNA sequences.

Further, the primers in Table 4 were also useful in evaluating gene expression of multiple pearl millet lipase genes.

In the present disclosure, PCR amplification products can be screened to identify PgTAGLip1 and PgTAGLip2 mutations using any method known to a person skilled in the art, that identifies nucleotide differences between wild-type and mutant sequences. These may include, for example, but are not limited to, sequencing or preferably, direct PCR amplification products by distinguishing the product size (large indels identification) and/or could be incubated with an endonuclease that preferentially cleaves mismatches in heteroduplexes between wild-type and mutant sequences followed by electrophoresis using agarose gel apparatus, and image analyses. DNA or RNA from plants with induced or naturally occurring mutations or deletions were screened with or without PCR by next-generation sequencing methods such as exome capture or TILLING/EcoTILLING methods using sequencing methods.

Mutation in each PgTAG Lipase gene is evaluated in order to predict its impact on protein function (i.e., from completely tolerated to causing loss-of-function) using bioinformatics tools such as SIFT (Sorting Intolerant from Tolerant), PSSM (Position-Specific Scoring Matrix) and PARSESNP. For example, a SIFT score that is less than 0.05 and a large change in PSSM score (e.g., roughly 10 or above) indicate a mutation that is likely to have a deleterious effect on protein function.

(b) Sequence Variation Between Mutant and WT Alleles

Multiple PgTAG Lipase genes were identified based upon their homology with known lipases using the latest version of the pearl millet genome (Varshney R, Shi C, Thudi M et al. (2017) Pearl millet genome sequence provides a resource to improve agronomic traits in arid environments. Nat Biotechnol 35: 969-976). To find the evolutionary relationships of pearl millet Lipase proteins with other species, the phylogenetic tree was constructed within the pearl millet and compared with closely related species such as rice using the Neighbor-Joining (NJ) method of the Mac Vector assembly program (V16.04).

To find the sequence variations, the PgTAGLip1 and PgTAGLip2 genes were cloned from different genotypes and sequenced using standard sequencing methods such as Sanger sequencing. Comparative sequencing analysis of coding regions revealed 50 structural variants in the PgTAGLip1 and PgTAGLip2 genes (single base to large indels) resulting in either missense mutation or loss of function of the gene and affect its functionality.

Table 7 shows the point mutations that are created in PgTAG Lipase 1 (DNA sequence SEQ ID NO: 1, Protein sequence SEQ ID NO: 2).

TABLE 7

| Nucleotide mutations identified in SEQ ID NO: 1 | Amino acid mutation identified in SEQ ID NO: 2 |
|---|---|
| GCG-ACG (34-36) | A12T |
| CTG-GCT (52-54) | L18A |
| CTG-CGC (55-57) | L19R |
| TCC-TCA (58-60) | S20S |
| CCT-CTG (67-69) | P23L |
| TCT-CTC (109-111) | S37L |
| TCT-TTC (113-114) | S38F |

TABLE 7-continued

| Nucleotide mutations identified in SEQ ID NO: 1 | Amino acid mutation identified in SEQ ID NO: 2 |
|---|---|
| ACT-TTT 124-126 | T42F |
| GAG-TGA (127-129) | E43* |
| TCC-TGA (130-132) | S44* |
| GGG-TGG (286-288) | C96W |
| TTT-GTT (289-291) | F97V |
| GAG-TGA (292-294) | E98* |
| GTT-TAG (340-342) | V114* |
| AAG-ATA (391-393) | K131I |
| ATT-TGA (403-405) | I135* |
| GTT-TGG (430-432) | V144W |
| GGT-TGT (433-435) | G145C |
| GTT-TGA (436-438) | V146* |
| AAC-ACT (499-501) | N167T |
| TGG-GGA (502-504) | W168G |
| ATT-TTA (505-507) | I169L |
| TTG-TGA (514-516) | L172* |
| GCC-CCA (613-615) | A205P |
| ATA-TAA (616-618) | I206* |
| ATC-TCA (616-618) | I206S |
| AAG-AGT (643-645) | K215S |
| GAC-ACA (661-663) | D221T |
| ATA-TAA (664-666) | I222* |
| TGT-TAT (709-711) | C237Y |
| GGA-TGA (736-738) | G246* |
| GCT-CCT (787-789) | A263P |
| TTG-TGC (865-867) | L289C |
| CCT-CTT (871-873) | P290L |
| CAG-AGC (892-894) | Q298S |
| CTG-TGA (895-897) | L299* |
| AAT-ATT (988-990) | N330I |
| TTC-TCT (1015-1017) | F339S |
| TTG-TGA (1036-1038) | L346* |

Table 8 shows the point mutations that are created in PgTAG Lipase 2 (DNA sequence SEQ ID NO: 3, Protein sequence SEQ ID NO: 4).

TABLE 8

| Nucleotide mutations identified in SEQ ID NO: 3 | Amino acid mutation identified in SEQ ID NO: 4 |
|---|---|
| GCT-GTT (658-660) | A220V |
| GCG-GTG (667-669) | A223V |
| TGG-TAG (793-795) | W265* |
| AGG-GGG (946-948) | R316G |
| GGA-ATC (949-951 | G317I |
| TCT-TTG (952-954) | S318L |
| TGT-TCA (955-957) | C319S |
| CAA-ATT (958-960) | Q320I |
| TTT-TGT (961-963) | F321C |
| GTA-AAT (964-966) | V322N |
| ATG-GGG (967-969) | M323G |
| GGT-TTC (970-972) | G324F |
| TCC-CGC (973-975) | S325R |
| GCC-CAA (976-978) | A326Q |
| AAC-CTC (979-981) | N327L |
| TCA-AGT (982-984) | S328S |
| GTA-ATA (985-987) | V329I |
| TAC-CAG (988-990) | Y330Q |
| AGC-CTA (991-993) | S331L |
| TAC-CAT (994-996) | Y332H |

Mutants including insertions, deletions were also determined in PgTAG Lipase 1 and PgTAG Lipase 2. Table 9 shows the mutations including insertions and deletions in PgTAG Lipase 1.

TABLE 9

| SEQ ID | Description of nucleotide mutation |
|---|---|
| SEQ ID NO: 12 | 84 bp insertion at 89 nucleic acid position |
| SEQ ID NO: 13 | Insertion at 30 position (GTSIFVPR*) |
| SEQ ID NO: 14 | 17 bp nucleotides deletion (269-285 bp) |
| SEQ ID NO: 15 | 6 amino acids deletion (CNDLTR) (90-95 amino acid position) |
| SEQ ID NO: 16 | 116 bp insertion at 287 nucleotide position |
| SEQ ID NO: 17 | insertion at 96 position (V*) |
| SEQ ID NO: 18 | 155 bp deletion (269-423 bp) |
| SEQ ID NO: 19 | 51 amino acids deletion (91-141 amino acid position) |
| SEQ ID NO: 20 | 90 b nucleotide deletion (331-420) |
| SEQ ID NO: 21 | 30 amino acids deleted (111-140 position) |
| SEQ ID NO: 22 | 7 nucleotides deletion AGCATAC (490-496) |
| SEQ ID NO: 23 | 2 amino acids deleted (164-165 position), frame shifted |
| SEQ ID NO: 24 | 49 b nucleotide deletion (565-613) |
| SEQ ID NO: 25 | 16 amino acids deletion (189-224) |

Table 10 shows the mutations including insertions and deletions in PgTAG Lipase 2.

TABLE 10

| SEQ ID | Description of nucleotide mutation |
|---|---|
| SEQ ID NO: 26 | 6 bp insertion at 33 position (CTGCTC) |
| SEQ ID NO: 27 | 2 amino acids 11$^{th}$ position (LL) |
| SEQ ID NO: 28 | 3 bp insertion at 32 position (TGC) |
| SEQ ID NO: 29 | Insertion of one amino acid at 12 position (L) |
| SEQ ID NO: 30 | 6 nucleotides insertion at 80th position (GGGTGC) |
| SEQ ID NO: 31 | Insertion of 2 amino acids at 28th position GA |

(c) CRISPR/Cas9 Gene Editing

CRISPR/Cas9 gene editing constructs (recombinant construct) were prepared as described by Anand et al. (2019) "Novel ternary vectors for efficient *sorghum* transformation" in *Sorghum* (pp. 185-196) Humana Press, New York, NY. In the present example, both single gRNA and as well as multi-gRNA expression cassettes were used for CRISPR/Cas9. In the first step, 20 bp guide RNA (as shown in Table 11 and 12) was cloned into donor vectors consisting of *Z. mays* U6 promoter, terminator and gRNA scaffold through overlapping and infusion PCR. The binary vector contained the Cas9 gene fused with *Z. mays* Ubiquitin promoter and Potato PINII terminator. Both sgRNA and Cas9 cassettes were further cloned into a destination vector through multisite gateway cloning.

Table 11 shows the guide RNA targeting the polynucleotide having a nucleotide sequence as set forth in SEQ ID NO: 1 (PgTAG Lip1)

TABLE 11

| SEQ ID of guide RNA | Strand | Position of the target polynucleotide (SEQ ID NO: 1) |
|---|---|---|
| SEQ ID NO: 60 | +Ve (sense strand) | 139-158 |
| SEQ ID NO: 61 | −Ve (anti-sense strand) | 348-367 |
| SEQ ID NO: 62 | +Ve (sense strand) | 500-519 |
| SEQ ID NO: 63 | +Ve (sense strand) | 670-689 |
| SEQ ID NO: 64 | −Ve (anti-sense strand) | 728-747 |
| SEQ ID NO: 65 | +Ve (sense strand) | 922-941 |

Table 12 shows the guide RNA targeting the polynucleotide having a nucleotide sequence as set forth in SEQ ID No: 3 (PgTAGLip2).

TABLE 12

| SEQ ID of guide RNA | Strand | Position of the target polynucleotide (SEQ ID NO: 3) |
|---|---|---|
| SEQ ID NO: 72 | −Ve (anti-sense strand) | 115-134 |
| SEQ ID NO: 73 | +Ve (sense strand) | 270-289 |
| SEQ ID NO: 74 | −Ve (anti-sense strand) | 415-434 |
| SEQ ID NO: 75 | +Ve (sense strand) | 534-553 |
| SEQ ID NO: 76 | +Ve (sense strand) | 773-792 |
| SEQ ID NO: 77 | +Ve (sense strand) | 991-1010 |

The binary plasmids contained spectinomycin for bacterial selection, CYAN1 and NPTII as plant reporter and selectable markers, respectively. The final expression cassettes were confirmed by Sanger DNA sequencing before transforming into *Agrobacterium* (host cell). The ternary vector was constructed by transforming the accessory plasmid into an *Agrobacterium* auxotrophic strain LBA4404 Thy-strain and selected on media containing 25 mg/L gentamicin. Subsequently, the binary constructs were electroporated into *Agrobacterium* strain LBA4404 Thy-containing the accessory plasmid and recombinant colonies were used for pearl millet transformation.

Economically important pearl millet genotypes (high yielding varieties) were used to transform expression cassettes (recombinant construct) prepared from multiple sources such as RNAi and genome editing tools through immature embryos described by Che, et al. (2018) Developing a flexible, high-efficiency *Agrobacterium*-mediated *sorghum* transformation system with broad application. Plant Biotechnology Journal 16(7):1388-95. Out of all the important pearl millet genotypes, only I7 mutant line was used to functionally validate the genes.

The immature embryos (explant) of pearl millet genotypes were co-cultured with *Agrobacterium tumefaciens* LBA4404 Thy-consisting of expression cassettes were further subjected to the following sequential steps: (i) *Agrobacterium* infection (ii) co-cultivation (iii) resting in the dark (iv) embryos selection in selection media (v) regeneration, and vi) rooting. Regenerated plantlets were transferred into pots and used for subsequent analysis.

Genomic DNA was isolated from the leaves of transformed pearl millet plants (gene-edited pearl millet plants) using the Nucleo Spin plant II midi kit (Macherey-Nagel, Duren, Germany) following the manufacturer's protocol. To ascertain transgene integration, polymerase chain reaction (PCR) analysis of the genomic DNA was carried out using primers (as shown in Table 13) to detect selection marker genes integration. The genomic DNA flanks around the sgRNA target sites were amplified and sequenced using appropriate primers to determine the mutations in the target genes. Selected E0 plants with mutations were self-crossed and advanced to the next generations.

TABLE 13

| SEQ ID | Description | Sequence |
|---|---|---|
| SEQ ID NO: 106 | PgTAGLip1 gRNAseq F | GTTATGGTGCTCTTGCTGCTGT |
| SEQ ID NO: 107 | PgTAGLip1 gRNAseq F | GTCTGCAATGATGACGTCGA |
| SEQ ID NO: 108 | PgTAGLip2 gRNAseq F | GAGCAGAAAGGAGTACTCACG |
| SEQ ID NO: 109 | PgTAGLip2 gRNAseq R | CTAGGATATGTGATTCTTGCG |

(d) Tilling

Chemical mutagenesis methods based on EMS may also be used to create and identify the PgTAGLipase 1 and 2 mutations using a method known as Targeting Induced Local Lesions IN Genomes (TILLING) (McCallum C M, Comai L, Greene E A & Henikoff S (2000) Targeting induced local lesions in genomes (TILLING) for plant functional genomics. Plant Physiology 123(2): 439-442).

The present example demonstrates how the mutations are created and identified in PgTAGLip1 (SEQ ID NO: 1) and PgTAGLip2 (SEQ ID NO: 3) using the TILLING methodology. For this purpose, pearl millet seeds are mutagenized and grown into M1 plants and self-pollinated to obtain M2 plants. DNA samples from the resulting M2 plants are pooled and re-screened for mutations in a gene of interest. Having identified a mutation in a gene of interest (SEQ ID NO: 1, or SEQ ID NO: 3), the seeds of the M2 plant carrying that mutation are grown into mature M3 plants and screened for the phenotypic characteristics associated with the gene of interest.

(e) RNA Interference (RNAi)

RNA interference (RNAi) is a biological mechanism involved in sequence-specific inhibition of gene expression by double-stranded RNA (dsRNA) molecules to prevent the expression of specific genes. The sense and antisense sequences are flanked by an unrelated sequence (spacer sequences preferably intragenic region), enabling the sense and anti-sense sequences to hybridize to form the dsRNA molecule with the unrelated sequence forming a loop structure and induces cleavage. The length of the sense and anti-sense sequences that hybridize should be 500 or 1000 nucleotides with the degree of identity most preferably 95-100%. The RNA molecule may of course comprise unrelated sequences which may function to stabilize the molecule. The targeted mRNA molecule may be expressed under the control of an RNA polymerase II or RNA polymerase III promoter. Examples of the latter include tRNA or snRNA promoters.

The present example demonstrates the development of recombinant construct, recombinant vector, and transgenic pearl millet plant with reduced lipase activity, using RNAi technology. For this purpose, the PgTAGLip1 (SEQ ID NO: 1) and PgTAGLip2 (SEQ ID NO: 3) coding regions around 200 bp are used to design dsRNA constructs (recombinant constructs) suitable for RNAi experiments in pearl millet using different web-based online tools such as E-RNAi and RNAi designing tool from IDT (https://www.idtdna.com/site/order/designtool/index/DSIRNA_CUSTOM).

Further, these regions are amplified from the PgLipase cDNA using primers listed in Table 14 cloned into a plant transformation vector through gateway-mediated cloning.

TABLE 14

| SEQ ID NO: | Description | Sequence |
|---|---|---|
| SEQ ID NO: 44 | PgLipase_RNAi_SF | ACATGGACATGCTCAAGATGT |
| SEQ ID NO: 45 | PgLipase_RNAi_SR | ATTATCACTTCCAAAGCTGAT |
| SEQ ID NO: 46 | PgLipase_RNAi_ASF | ATTATCACTTCCAAAGCTGA |
| SEQ ID NO: 47 | PgLipase_RNAi_ASR | ACATGGACATGCTCAAGATGT |

The gene fragment region in opposing orientations on either side of a PDK intron (SEQ ID NO: 66)/chsA intron (SEQ ID NO: 67) creates an inverted repeat driven by a constitutive promoter or a seed-preferred promoters disclosed herein. The PgTAGLip1 and PgTAGLip2 RNAi plasmids (recombinant construct) are transformed into pearl millet using *Agrobacterium tumefaciens* strain LBA4404/LBA4404thy—through immature embryos (implant), to obtain transgenic plant (see protocol described by Che P, et al. (2018)). See also, Developing a flexible, high-efficiency *Agrobacterium*-mediated *sorghum* transformation system with broad application. Plant Biotechnology Journal 16(7): 1388-95). Genomic DNA is isolated from the leaves of transformed pearl millet plants (transgene pearl millet plant) using the Nucleo Spin plant II midi kit (Macherey-Nagel, Duren, Germany) following the manufacturer's protocol. To ascertain transgene integration, genomic DNA is analyzed by polymerase chain reaction (PCR) using primers listed in Table 15 to detect npt II/hpt gene integration.

TABLE 15

| SEQ ID | Description | Sequence |
|---|---|---|
| SEQ ID NO: 110 | nptII_ConF | TTGATATACTTGGATGATGGCATA |
| SEQ ID NO: 111 | nptII_ConR | AGCCATGATGGATACTTTCTCG |
| SEQ ID NO: 112 | Hpt_F | TTGACATTGGGGAGTTTAGCGA |
| SEQ ID NO: 113 | Hpt_R | GTTTCCACTATCGGCGAGTACT |

Example 6

Use of Markers to Detect and Identify Pearl Millet Lines, Including High Yielding Lines of Pearl Millet, Having Lower Lipase Activity.

PgTAGLip1 (SEQ ID NO: 1) and PgTAGLip2 (SEQ ID NO: 3) sequence analysis revealed variants in these lipase sequences (including indels, small) that result in reduced or loss of gene function and functionality. PgTAGLip1 allelic variants were identified that have a single base change (as shown in Table 7) or that have deletions of 17 bp (SEQ ID NO: 14), 49 bp (SEQ ID NO: 24), or 90 bp (SEQ ID NO: 20) (as shown in Table 9), whereas, PgTAGLip2 allelic variants revealed insertions of 6 bp (SEQ ID NO: 26), 3 bp (SEQ ID NO: 28), and 6 bp (SEQ ID NO: 30) (as shown in Table 10), in addition to variants that have a single base change (as shown in Table 8). Cleaved amplified polymorphic sequence (CAPS)/derived Cleaved Amplified Polymorphic Sequences (dCAPS) and indels are used to develop markers for genotyping and marker-assisted detection and identification of pearl millet plants and lines having lower lipase activity. Thus, the markers developed and disclosed herein can be used to detect and identify pearl millet lines that provide seed or grain that (i) have lower lipase activity and (ii) can be milled to make flour or meal with reduced rancidity, as compared to seed from wild type pearl millet.

(a) SNP Based Markers

Single nucleotide polymorphisms (SNPs) in genomes for marker assays can guide genotyping and selection of desired lines in large-scale populations. Cleaved amplified polymorphic sequences (CAPS) assays involve the PCR amplification of an SNP site and the detection of this site by an appropriate restriction endonuclease whose recognition sequence has been altered or introduced by the SNP. Derived Cleaved Amplified Polymorphic Sequences (dCAPS) assay is a modification of CAPS technique for detection of Single Nucleotide Polymorphisms (SNPs).

CAPS and dCAPS marker primers are designed for PgTAGLip1, and PgTAGLip2 mutants using SNP2CAPS and dCAP finder (Neff M M, Turk E and Kalishman M (2002) Web-based Primer Design for Single Nucleotide Polymorphism Analysis. Trends in Genetics, 18 613-615), respectively. Table 16 list CAPS and dCAPS marker primers designed for PgTAG Lip1 (SEQ ID NO: 1).

TABLE 16

| SEQ ID | Description | Sequence |
|---|---|---|
| | dCAPs markers | |
| SEQ ID NO: 78 | PgTAGLip1_F | ATGGATAGGCGGAGACGCGCGGTCAAAGCG GCC |
| SEQ ID NO: 79 | PgTAGLip1_R | CTTGAGCATGTCCATGTGTATAGAG |
| | CAPS markers | |
| SEQ ID NO: 80 | PgTAGLip1_F | GGCGGAGACGCGCGGTCAAAGCGG |
| SEQ ID NO: 81 | PgTAGLip1_R | CTTGAGCATGTCCATGTGTATAGAG |

Table 17 list the CAPS and dCAPS marker primers designed for PgTAG Lip2 (SEQ ID NO: 3).

TABLE 17

| SEQ ID | Description | Sequence |
|---|---|---|
| | dCAPs markers | |
| SEQ ID NO: 88 | PgTAGLip2_F | TTTTGGACAACCTCGGATAGGCAATCCAG |
| SEQ ID NO: 89 | PgTAGLip2_R | TACTCAAGATGATCTGCCACACTTA |
| | CAPS markers | |
| SEQ ID NO: 90 | PgTAGLip2_F | AGCAGCTCGATGTGACTTATC |
| SEQ ID NO: 91 | PgTAGLip2_R | AGTACGCAGCAAAAGCAGGATT |

CAPS markers are based on PCR-amplifications of DNA fragments (SEQ ID NO: 1, or SEQ ID NO: 3) with specific primers. PCR-amplified product is digested with restriction enzymes and digested products are separated in an agarose gel. PCR product generated using SEQ ID NOs: 80 and 81 is digested with endonuclease FNu4H which produces restriction fragments of either about (i) 260 bp in length, indicative of PgTAGLip1 mutant plants or (ii) 234 and 26 bp in length, indicative of wild type plants. PCR product generated using SEQ ID NOs: 90 and 91 is digested with endonuclease HaeIII which produces restriction fragments of either about (i) 172 and 110 bp in length, indicative of PgTAGLip2 mutant plants or (ii) 282 bp in length indicative of wild type plants.

For dCAPS assay, PCR primers are used that introduce a restriction endonuclease (RE)-site in either PgTAGLip mutant plants or wild type plants (but not both). PCR-amplified product is then subjected to restriction enzyme digestion and the presence or absence of the PgTAGLip mutant sequence is determined by whether or not the RE-site is present in the PCR-amplified product. PCR product generated using SEQ ID NOs: 78 and 79 is digested with endonuclease AciI which produces restriction fragments of either about (i) 267 bp in length, indicative of PgTAGLip1 mutant plants or (ii) 237 and 30 bp in length, indicative of wild type plants. PCR product generated using SEQ ID NOs: 88 and 89 is digested with endonuclease AluI which produces restriction fragments of either about (i) 285 bp in length indicative of PgTAGLip2 mutant plants or (ii) 256 and 29 bp in length, indicative of wild type plants.

(b) InDel Markers

InDels are structural variations distributed throughout the genome that lead to the organism's gain/loss of function. InDels can be genotyped by sequencing or by simple gel-based size separation procedures and the absence/presence of the band in the gel or size variation in the gel. Primers for the flanking region of the identified InDels were designed using Primer3 software (Untergasser 2012). Table 18 list the InDels marker primers designed for PgTAGLip1 (SEQ ID NO: 1).

TABLE 18

| SEQ ID | Description | Sequence |
|---|---|---|
| SEQ ID NO: 82 | PgTAG Lip1_F1 | CTAACGGCTCTATACACATGG |
| SEQ ID NO: 83 | PgTAG Lip1_R1 | AGTTCCCCTTATTGCAACAA |
| SEQ ID NO: 84 | PgTAG Lip1_F2 | TATGGAAGCAAGTTAATCTT |
| SEQ ID NO: 85 | PgTAG Lip1_R2 | ATCGAGTGCCCTGTAACAAT |
| SEQ ID NO: 86 | PgTAG Lip1_F3 | GAATATGCATCAGCTGTATA |
| SEQ ID NO: 87 | PgTAG Lip1_R3 | AAGCAATTTTGGACATCAAC |

Table 19 list the InDels marker primers designed for PgTAGLip2 (SEQ ID NO: 3).

TABLE 19

| SEQ ID | Description | Sequence |
|---|---|---|
| SEQ ID NO: 92 | PgTAGLip2_F | ATGGCTGCGAAGGGCGCGAC |
| SEQ ID NO: 93 | PgTAGLip2_R | TCGCCACATCCACAATGACC |

Validation of these identified InDels was done through regular PCR and agarose gel electrophoresis.

The present disclosure provides an isolated polynucleotide encoding for a polypeptide having an amino acid sequence as set forth in SEQ ID NO: 2 (PgTAGLip1), or SEQ ID NO: 4 (PgTAGLip2), wherein the said isolated polynucleotide has one or more mutations. In an example, mutations that are introduced in SEQ ID NO: 1 result in a mutant polypeptide having an amino acid sequence as set forth in SEQ ID NO: 7, whereas, mutations that are introduced in SEQ ID NO: 3 results in a mutant polypeptide having an amino acid sequence as set forth in SEQ ID NO: 9, or SEQ ID NO: 11. The mutations that are created and identified in the isolated polynucleotide as described herein, confers specific properties of enhanced shelf life, reduced rancidity, reduced lipase activity, as compared to the wild type polynucleotide (SEQ ID NO: 1, or SEQ ID NO: 3). This property can then be extended to provide transgenic plants or gene-edited plants having reduced lipase activity and the characteristic features such as (a) reduced free fatty acid production; (b) reduced hexanal production; (c) increased oxidative stability; (d) increased hydrolytic stability; (e) reduced volatiles production; and (f) improved sensory characteristics (e.g., reduced rancidity), as compared to that of the wild type plant or non-transformed plant. The application of the present disclosure can further extended to provide the food products from the transgenic pearl millet plants or gene-edited plants, wherein the food products exhibit the desired characteristic features, such as, increased shelf life, reduced rancidity, and better sensory characteristics. The food product can be flour, meal, whole grain, and broken grain.

Advantages of the Present Disclosure

The present disclosure provides a precise understanding of the rancidity mechanism (both biochemical and molecular mechanism), which is an underlying and essential trait for nutritional improvement in pearl millet flour. The identification of the candidate gene(s) for enhanced shelf life/reduced rancidity would provide knowledge to develop new genetic materials in pearl millet. The present disclosure creates and identifies the mutant genes in SEQ ID NO: 1 (PgTAGLip1) or SEQ ID NO: 3 (PgTAGLip2) that acts as suitable candidates with specific properties such as low rancidity, increased shelf life, and reduced lipase activity. These mutant genes that are created or identified in the present disclosure would be useful in developing pearl millet with enhanced flour shelf life, which will change the way this pearl millet (nutricereal) is viewed by processing industry and open up a large market under gluten-free flour category that is not existing as of now due to issues of rancidity. This is likely to open new opportunities for enhancing the scope of its utilization as low glycemic index (GI), gluten-free flour, bakery & confectionery items, weaning foods, and dietary formulations for children as well as geriatrics, etc. Further, present disclosure opens avenues for breeding that would provide the pearl millet breeders and biotechnologists with the ideal toolbox to develop elite germplasm that will enhance the processing quality of this pearl millet crop.

Moreover, the present disclosure also discloses the transgenic pearl millet plants or food products comprising mutant genes having reduced activity as compared to wild type genes, wherein the transgenic pearl millet plants or food products exhibits the following characteristic properties, such as, (a) increased shelf life; (b) reduced free fatty acid production; (c) reduced hexanal production; (d) increased oxidative stability; (e) increased hydrolytic stability; (f) reduced volatiles production; and (g) improved sensory characteristics (e.g., reduced rancidity). The food product is selected from the group consisting of flour, meal, whole grain, and broken grain. Increasing the shelf life of nutritious pearl millet grain would also offer opportunities for primary and secondary processing, creating markets and enhanced profits for smallholder farmers. Further, reducing rancidity in millet flour (food product) would reduce waste and create a value-added product for both rural and urban consumers.

We claim:

1. A method of modifying a millet plant, tissue, or cell thereof comprising:

a) providing a pearl millet plant tissue, or cell thereof comprising a genomic sequence that encodes a triacylglycerol (TAG) lipase polypeptide; and b) modifying the genomic sequence encoding the TAG lipase to encode a modified TAG lipase, wherein the modified TAG lipase has a substitution or is truncated at the amino acid position corresponding to (i) position 12, 18, 19, 20, 23, 26, 37, 38, 42, 43, 44, 96, 97, 98, 114, 131, 135, 144, 145, 146, 167, 168, 169, 172, 205, 206, 215, 221,222, 237, 246, 263, 289, 290, 298, 299, 330, 339, or 346 of SEQ ID NO:2 or (ii) position 220, 223, 265, 316, 317, 318, 319, 320, 321, 322, 323, 324, 325, 326, 327, 328, 329, 330, 331, or 332 of SEQ ID NO:4, or encodes a polypeptide comprising the amino acid sequence of SEQ ID NO:7, SEQ ID NO:13, SEQ ID NO:15, SEQ ID NO:17, SEQ ID NO:19, SEQ ID NO: 21, SEQ ID NO:25, SEQ ID NO:9, SEQ ID NO:11, SEQ ID NO:22, SEQ ID NO: 26, SEQ ID NO:28, or SEQ ID NO:30, to thereby produce a modified pearl millet plant tissue, or cell thereof.

2. The method of claim 1, wherein the modified TAG lipase encodes a polypeptide comprising the amino acid sequence of SEQ ID NO:7.

3. The method of claim 1, wherein the modified TAG lipase encodes a polypeptide comprising the amino acid sequence of SEQ ID NO:13, SEQ ID NO: 15, SEQ ID NO:17, SEQ ID NO:19, SEQ ID NO:21, SEQ ID NO:25, SEQ ID NO:9, or SEQ ID NO:11.

4. The method of claim 1, wherein the modified genomic sequence comprises SEQ ID NO:22, SEQ ID NO:26, SEQ ID NO:28, or SEQ ID NO:30.

* * * * *